United States Patent
Wong et al.

(10) Patent No.: US 12,233,419 B2
(45) Date of Patent: Feb. 25, 2025

(54) DEVICES, SYSTEMS, AND METHODS FOR SINGLE CELL BACTERIA ANALYSIS

(71) Applicant: The Penn State Research Foundation, University Park, PA (US)

(72) Inventors: Pak Kin Wong, University Park, PA (US); Hui Li, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 1086 days.

(21) Appl. No.: 17/259,136

(22) PCT Filed: Jul. 11, 2019

(86) PCT No.: PCT/US2019/041482
§ 371 (c)(1),
(2) Date: Jan. 8, 2021

(87) PCT Pub. No.: WO2020/014537
PCT Pub. Date: Jan. 16, 2020

(65) Prior Publication Data
US 2021/0322984 A1    Oct. 21, 2021

Related U.S. Application Data

(60) Provisional application No. 62/696,474, filed on Jul. 11, 2018.

(51) Int. Cl.
*B01L 3/00*      (2006.01)
*C12Q 1/04*    (2006.01)
*C12Q 1/18*    (2006.01)
*C12Q 1/689*  (2018.01)

(52) U.S. Cl.
CPC .......... *B01L 3/502761* (2013.01); *C12Q 1/04* (2013.01); *C12Q 1/18* (2013.01); *C12Q 1/689* (2013.01); *B01L 2200/0668* (2013.01); *B01L 2300/0809* (2013.01); *B01L 2400/0406* (2013.01)

(58) Field of Classification Search
CPC ....... B01L 3/502761; B01L 2200/0668; B01L 2300/0809; B01L 2400/0406; B01L 3/502707; B01L 2300/0681; B01L 2400/0481; B01L 3/502753; C12Q 1/04; C12Q 1/18; C12Q 1/689; G01N 2021/6432; G01N 2021/6439; G01N 33/487; C01B 32/158
See application file for complete search history.

(56) References Cited

U.S. PATENT DOCUMENTS

| | | |
|---|---|---|
| 5,811,124 A | 9/1998 | Fernandez et al. |
| 6,103,476 A * | 8/2000 | Tyagi ................... C12Q 1/6816 435/6.1 |
| 2002/0029814 A1 * | 3/2002 | Unger ....................... F15C 3/00 137/824 |
| 2006/0223080 A1 | 10/2006 | Pollner et al. |
| 2013/0108667 A1 * | 5/2013 | Soikum ................... C12N 13/00 977/773 |
| 2014/0227695 A1 * | 8/2014 | Reshatoff ................. C12Q 1/68 435/6.11 |
| 2016/0257997 A1 * | 9/2016 | Stender ................ C12Q 1/6841 |
| 2016/0327470 A1 * | 11/2016 | Lee ..................... G01N 15/1484 |

FOREIGN PATENT DOCUMENTS

WO     2008044129 A2    4/2008

OTHER PUBLICATIONS

Wu et al, Biosensors and Bioelectronics, vol. 26, pp. 491-496, published online Jul. 24, 2010.*
Baker, J. D. et al., Programmable, Pneumatically Actuated Microfluidic Device with an Integrated Nanochannel Array To Track Development of Individual Bacteria, Analytical Chemistry, Sep. 8, 2016, vol. 88, No. 17, pp. 1-18.
Bachir, G. et al., *Escherichia coli* and *Staphylococcus aureus* most common source of infection, The Battle Against Microbial Pathogens: Basic Science, Technological Advances and Educational Programs, Book Chapter, FORMATEX, 2015, pp. 637-648.
Baltekin, O. et al., Antibiotic susceptibility testing in less than 30 min using direct single-cell imaging, Proceedings of the National Academy of Sciences of the United Stated of America, Aug. 22, 2017, vol. 114, No. 34, pp. 9170-9175.
Cellasic, Dynamic Live Cell Imaging of Bacteria, CellASIC Corp., Feb. 24, 2011, pp. 1-4. https://www.imperial.ac.uk/media/imperial-college/medicine/facilities/film/B04A-02-App-Note-Dynamic-Live-Cell-Imaging-of-Bacteria.pdf.
Giersig, M. et al., Novel electroporation System for both Gram-negative and Gram-positive Bacteria Assisted by Multi-Walled Carbon Nanotubes, Material Research Society Symposium Proceedings, 2005, vol. 845, pp. 285-290.
Cai, D. et al., Interaction between carbon nanotubes and mammalian cells: charaterization by flow cytometry and application, Nanotechnology, Jul. 15, 2008, vol. 19, No. 34, pp. 1-10.

(Continued)

*Primary Examiner* — Narayan K Bhat
(74) *Attorney, Agent, or Firm* — Hodgson Russ LLP

(57) ABSTRACT

Provided are devices and methods for detecting the presence, absence, and/or characteristics of bacteria. A microfluidic device for characterizing bacteria is provided. The device contains one or more bacteria trapping channels, and one or more pneumatic channels in contact with the bacteria trapping channels, wherein the one or more pneumatic channels are configured to reduce the height of the one or more bacteria trapping channels to thereby trap bacteria in the one or more bacteria trapping channels if said bacteria are present in a liquid biological sample that is introduced into the microfluidic device. Also provided is a method for identifying bacteria that may be used with the microfluidic device.

6 Claims, 39 Drawing Sheets

Specification includes a Sequence Listing.

(56) References Cited

OTHER PUBLICATIONS

Ramon-Garcia, S. et al., Targeting *Mycobacterium tuberculosis* and Other Microbial Pathogens Using Improved Synthetic Antibacterial Peptides, Antimicrobial Agents and Chemotherapy, Mar. 11, 2013, vol. 57, No. 5, pp. 2295-2303.

Ramadoss, N. S. et al., Small molecule inhibitors of trans-translation have broad spectrum antibiotic activity, Proceedings of the National Academy of Sciences of the United States of America, Jun. 18, 2013, vol. 110, No. 25, pp. 10282-10287.

Zamani, M. et al., Advances in drug delivery via electrospun and electrosprayed nanomaterials, Interntional Journal of Nanomedicine, Aug. 8, 2013, vol. 8, pp. 2997-3017.

* cited by examiner

A

B

A

B

C

C

| Buffer | Nanotube | Efficiency (%) | Growth (%) |
|---|---|---|---|
| MHB | 100% | 4.35±2.50 | 89.32±16.20 |
| | 50% | 0 | 68.06±6.96 |
| DI water | 100% | 91.99±2.69 | 0 |
| | 50% | 85.55±3.85 | 0 |
| PBS, 1X | 100% | 0 | 5.44±4.25 |
| | 50% | 0 | 61.9±11.96 |
| PBS, 0.5X | 100% | 90.87±8.73 | 28.64±3.85 |
| | 50% | 81.58±3.48 | 49.48±5.49 |

SEQUENCE LISTING

<160> NUMBER OF SEQ ID NOS: 11

<210> SEQ ID NO 1
<211> LENGTH: 24
<212> TYPE: DNA
<213> ORGANISM: artificial sequence
<220> FEATURE:
<223> OTHER INFORMATION: DNA probe

<400> SEQUENCE: 1
ggtattaact ttactccctt cctc                                        24

<210> SEQ ID NO 2
<211> LENGTH: 12
<212> TYPE: DNA
<213> ORGANISM: artificial sequence
<220> FEATURE:

<223> OTHER INFORMATION: DNA probe

<400> SEQUENCE: 2
gaggaaggga gt                                                           12

<210> SEQ ID NO 3
<211> LENGTH: 24
<212> TYPE: DNA
<213> ORGANISM: artificial sequence
<220> FEATURE:
<223> OTHER INFORMATION: DNA probe

<400> SEQUENCE: 3
ggtattaact ttactccctt cctc                                              24

<210> SEQ ID NO 4
<211> LENGTH: 12
<212> TYPE: DNA
<213> ORGANISM: artificial sequence
<220> FEATURE:
<223> OTHER INFORMATION: DNA probe

<400> SEQUENCE: 4
gaggaaggga gt                                                           12

<210> SEQ ID NO 5
<211> LENGTH: 24
<212> TYPE: DNA
<213> ORGANISM: artificial sequence
<220> FEATURE:
<223> OTHER INFORMATION: EC DNA target

<400> SEQUENCE: 5
gaggaaggga gtaaagttaa tacc                                              24

<210> SEQ ID NO 6
<211> LENGTH: 23
<212> TYPE: DNA
<213> ORGANISM: artificial sequence
<220> FEATURE:
<223> OTHER INFORMATION: DNA probe

<400> SEQUENCE: 6
gctgaaccac ctacgcgcgc ttt                                               23

<210> SEQ ID NO 7
<211> LENGTH: 12
<212> TYPE: DNA
<213> ORGANISM: artificial sequence
<220> FEATURE:
<223> OTHER INFORMATION: DNA probe

<400> SEQUENCE: 7
aaagcgcgcg ta                                                           12

<210> SEQ ID NO 8
<211> LENGTH: 23
<212> TYPE: DNA
<213> ORGANISM: artificial sequence
<220> FEATURE:
<223> OTHER INFORMATION: DNA target

<400> SEQUENCE: 8
aaagcgcgcg taggtggttc agc                                               23

```
<210> SEQ ID NO 9
<211> LENGTH: 22
<212> TYPE: DNA
<213> ORGANISM: artificial sequence
<220> FEATURE:
<223> OTHER INFORMATION: DNA probe

<400> SEQUENCE: 9
gggtatctaa tcctgtttgc tc                                                  22

<210> SEQ ID NO 10
<211> LENGTH: 10
<212> TYPE: DNA
<213> ORGANISM: artificial sequence
<220> FEATURE:
<223> OTHER INFORMATION: DNA probe

<400> SEQUENCE: 10
gagcaaacag                                                                10

<210> SEQ ID NO 11
<211> LENGTH: 22
<212> TYPE: DNA
<213> ORGANISM: artificial sequence
<220> FEATURE:
<223> OTHER INFORMATION: DNA target

<400> SEQUENCE: 11
gagcaaacag gattagatac cc                                                  22
```

DEVICES, SYSTEMS, AND METHODS FOR SINGLE CELL BACTERIA ANALYSIS

CROSS REFERENCE TO RELATED APPLICATIONS

This application claims priority to U.S. provisional patent application No. 62/696,474, filed Jul. 11, 2018, the disclosure of which is incorporated herein by reference.

FEDERAL SUPPORT CLAUSE

This invention was made with government support under Grant No. AI117032 awarded by the National Institutes of Health and under Grant No. HDTRA1-16-C-0004 awarded by the Department of Defense/DTTR. The Government has certain rights in the invention.

FIELD

The present disclosure is related to devices, systems, and methods for characterization of prokaryotic cells.

BACKGROUND

There is an ongoing and unmet need for improved methods of bacteria detection, characterization of size and antimicrobial susceptibility, and identification. The present disclosure is pertinent to these needs.

BRIEF SUMMARY

This disclosure is divided into two parts (Part I and Part II), which are related to one another in terms of bacterial detection, characterization, and identification. Part I of this disclosure relates to an adaptable microfluidic system for rapid pathogen classification and antimicrobial susceptibility testing at the single cell level. By incorporating tunable microfluidic channels along with real-time optical detection, bacteria can be trapped and separated according to their physical shape and size for pathogen classification. By monitoring their growth at the single cell level in the presence of antibiotics, antimicrobial susceptibility of the bacteria can be determined in as little as 30 minutes compared to days required for standard procedures. The microfluidic system is able to detect bacterial pathogens in urine, blood cultures, and whole blood and can analyze polymicrobial samples.

Part II of this disclosure relates to a nanotube assisted microwave electroporation (NAME) technique for delivering molecular biosensors into viable bacteria for multiplex single cell pathogen identification. Due to the small volume of a bacterial cell, the intracellular concentration of the target molecule is high, which results in a strong signal for single cell detection without amplification. The NAME procedure can be completed in as little as 30 minutes and can achieve over 90% transformation efficiency. The disclosure demonstrates the NAME procedure by identifying clinical isolates of bloodborne and uropathogenic pathogens and detecting bacterial pathogens directly from patient samples. In conjunction with a microfluidic single cell trapping technique of Part I, NAME allows single cell pathogen identification and antimicrobial susceptibility testing (AST) concurrently. Using this approach, the time for microbiological analysis reduces from days to hours, which is expected to have a significant impact on the clinical management of bacterial infections.

BRIEF DESCRIPTION OF FIGURES

Part I Figure Descriptions

Part II Figure Descriptions

Figure 20:
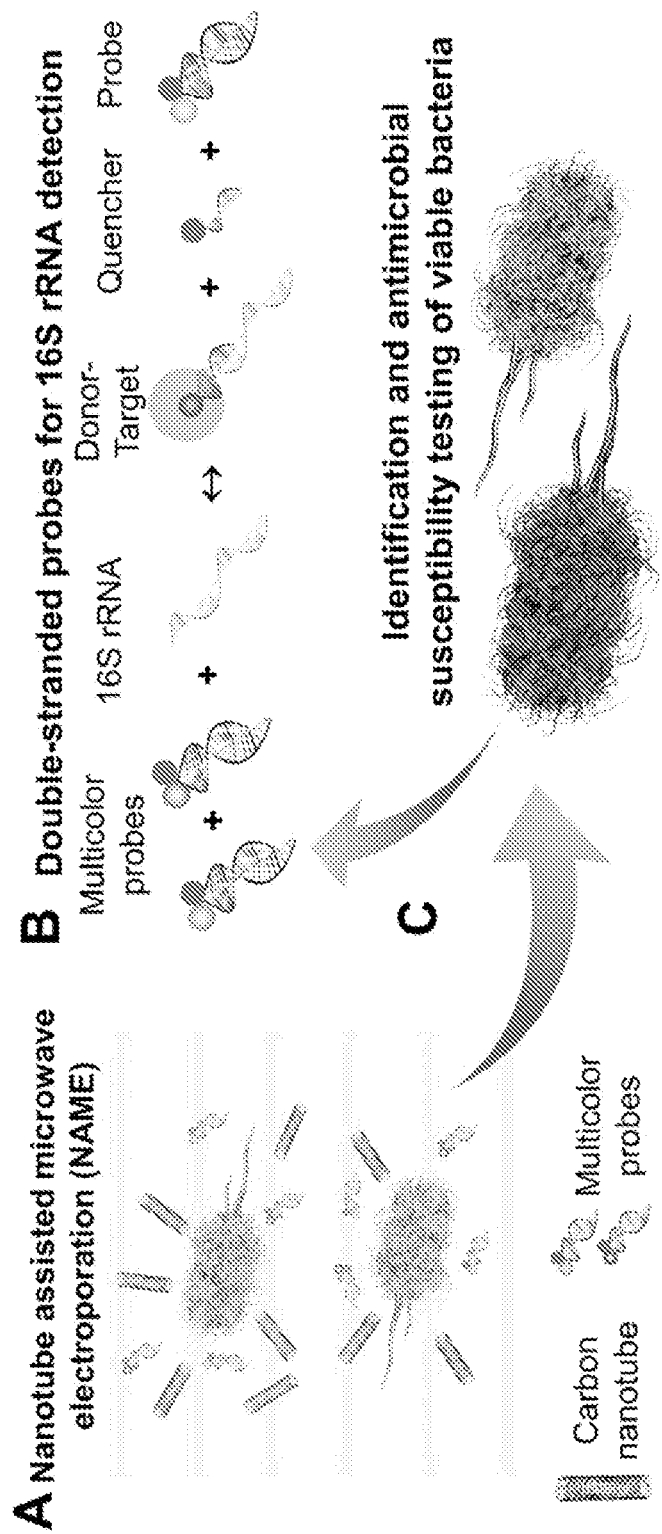
Figure 20:
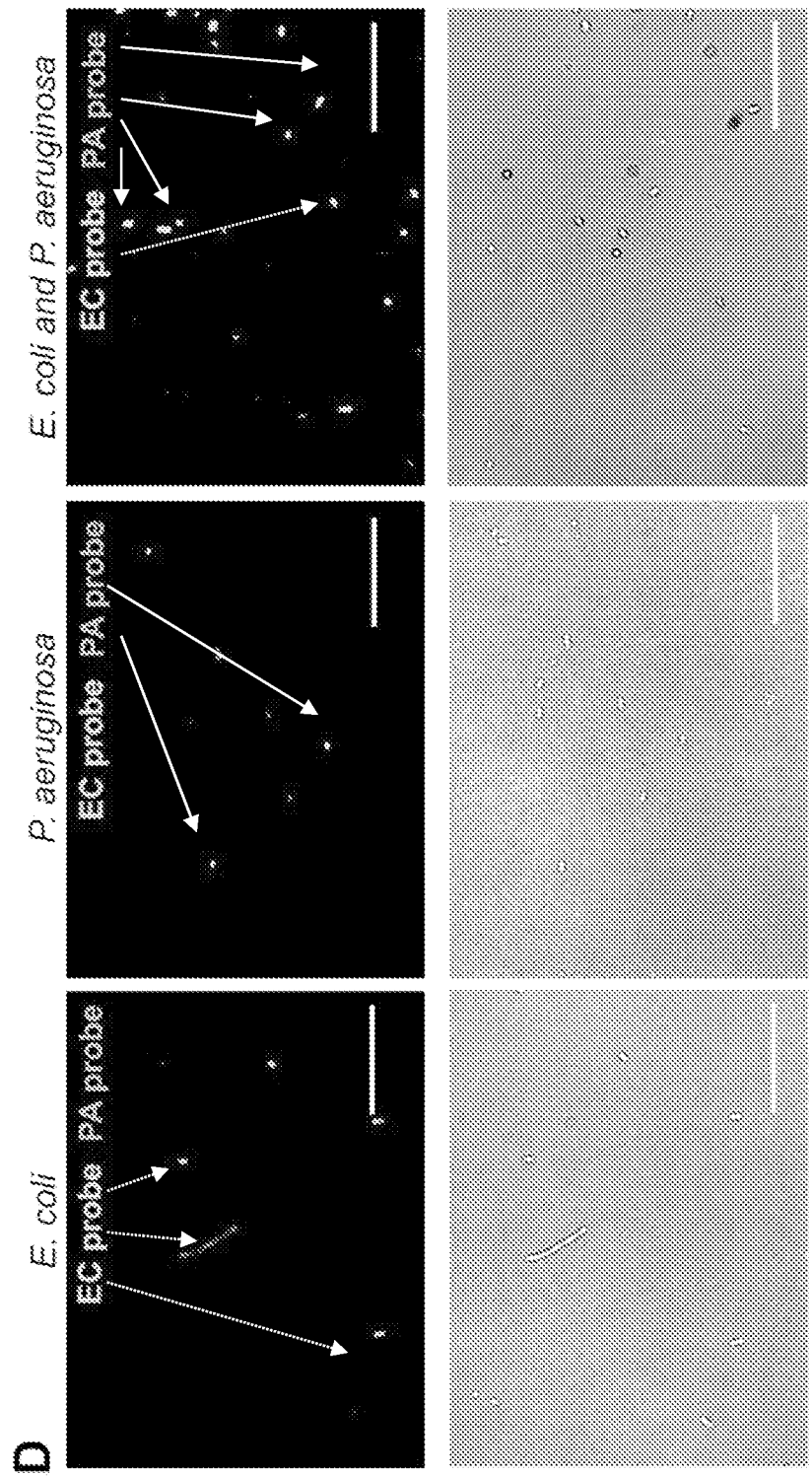

FIG. 20. Nanotube assisted microwave electroporation (NAME) for single cell pathogen identification. (a) Schematic of microwave electroporation enhanced by multiwall carbon nanotubes for delivering nucleic acid probes into viable bacteria. (b) Multicolor double-stranded probes for multiplex 16S rRNA detection. Hybridization of the target 16S rRNA with the donor probe displaces the quencher probe allowing the fluorophore to fluoresce. Fluorescence is detected only when a specific probe is transformed into the bacteria for pathogen identification. (c) Intracellular detection of bacterial 16S rRNA in viable cells enables pathogen identification and subsequent antimicrobial susceptibility testing at the single cell level. (d) Multiplex detection of *E. coli* and *P. aeruginosa* by NAME. Multicolor double-stranded probes targeting *E. coli* (EC probe, red) and *P. aeruginosa* (PA probe, green) were transformed into samples with *E. coli, P. aeruginosa*, or mixture of both bacteria at 1:1 ratio. Fluorescence images with merged red and green channels (top) and bright-field images (bottom) demonstrate pathogen identification at the single cell level. Images are representative of three tests. Scale bars, 25 μm.

Figure 21:
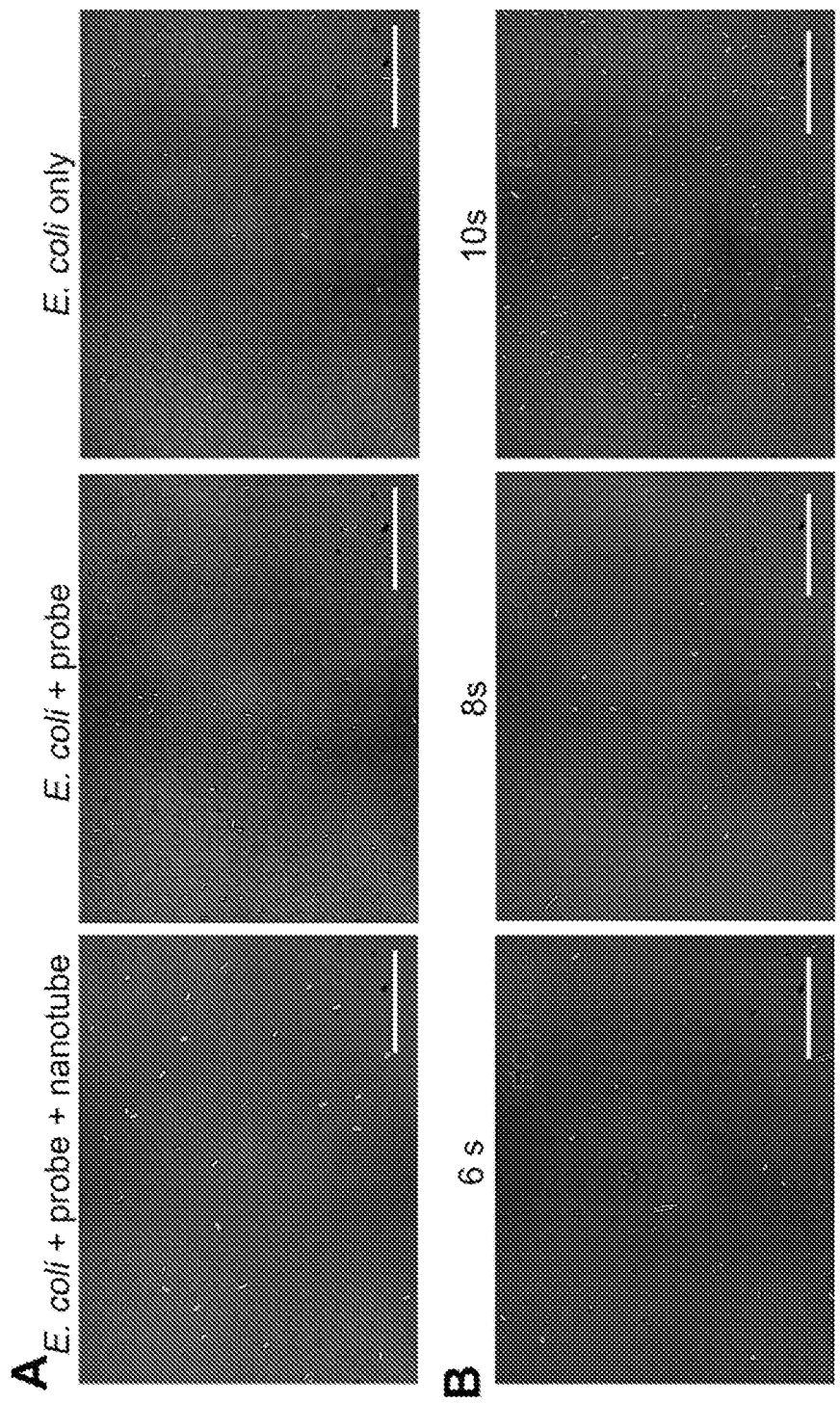
Figure 21:
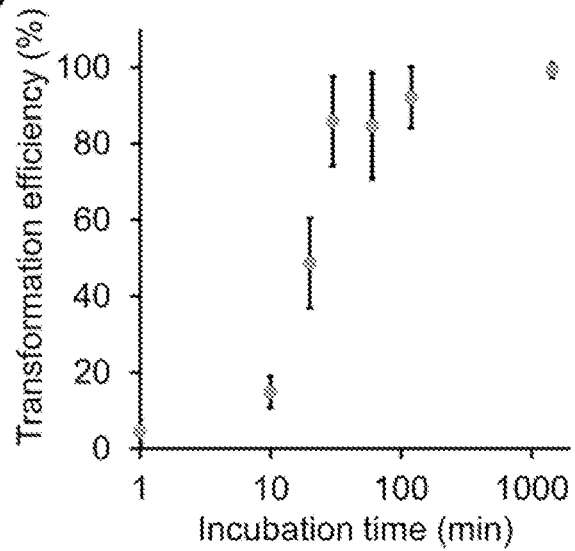

FIG. 21. Transformation of viable bacteria. (a) Overlay images of *E. coli* clinical isolates (EC137) transformed with or without carbon nanotubes. Fluorescence was observed only in samples with nanotubes. *E. coli* treated with the same microwave duration (i.e., no probe) was applied as control. Scale bars, 50 μm. (b) Overlay images illustrating the effect of the microwave time on the transformation efficiency. Scale bars, 50 μm. Images are representative of three tests. (c) Effects of the buffer solution on the transformation efficiency and ability of the bacteria to divide and grow. (d) The effect of the incubation time on the transformation efficiency (n=3).

Figure 22:
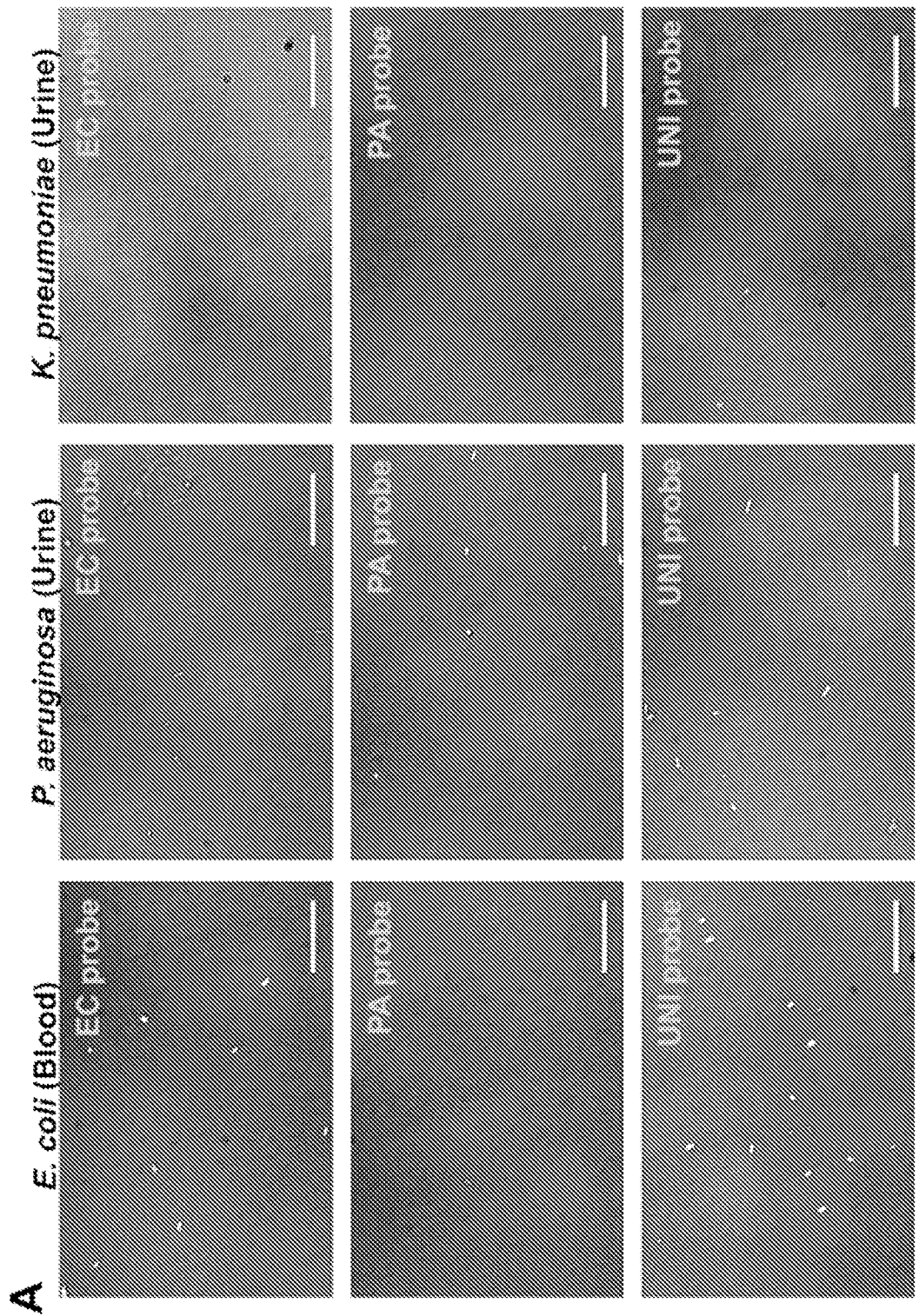
Figure 22:
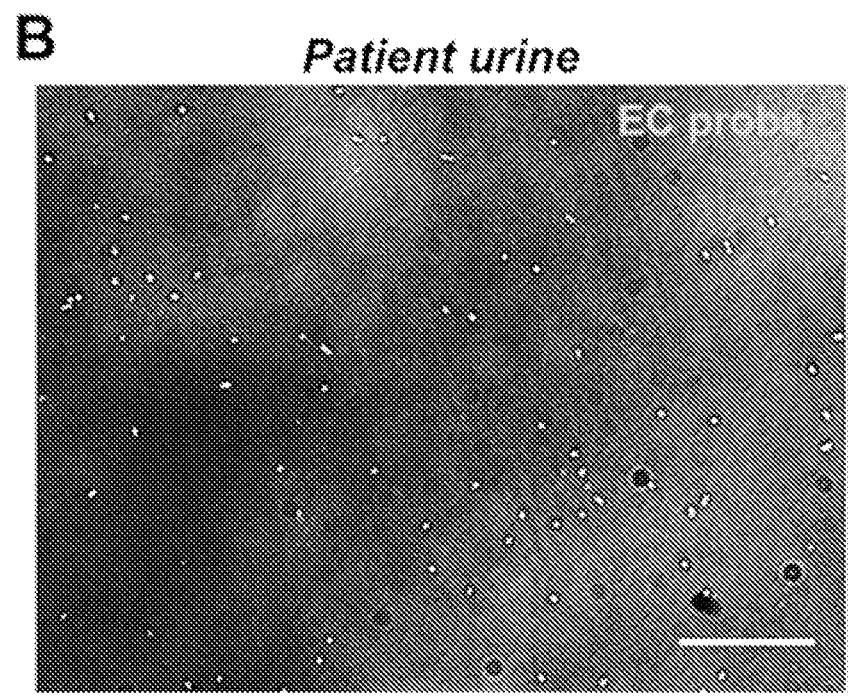
Figure 22:
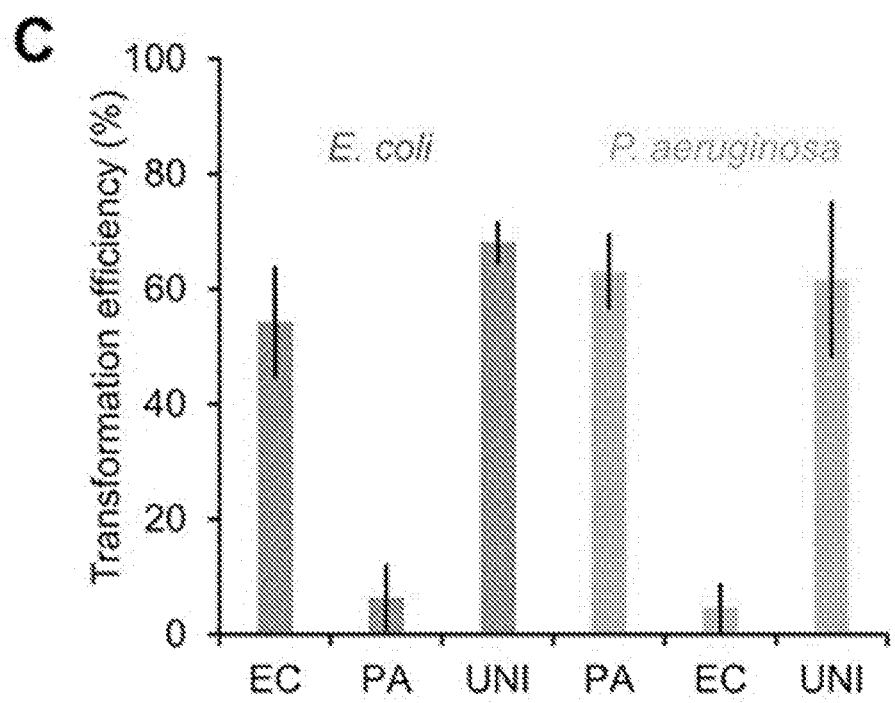

FIG. 22. Single cell pathogen identification of clinical specimens. (a) Overlay images demonstrating detection of *E. coli, P. aeruginosa* and *K. pneumoniae* clinical isolates from patient urine and blood samples. Scale bars, 25 μm. Top row of panels, EP probe. Middle row of panels, PA probe. Bottom (third) row of panels, UNI probe. (b) Culture-free pathogen identification of patient urine samples. Scale bar, 25 μm. (c) Multiplex detection of *E. coli* and *P. aeruginosa* with EC, PA, and UNI probes (n=3).

Figure 23:
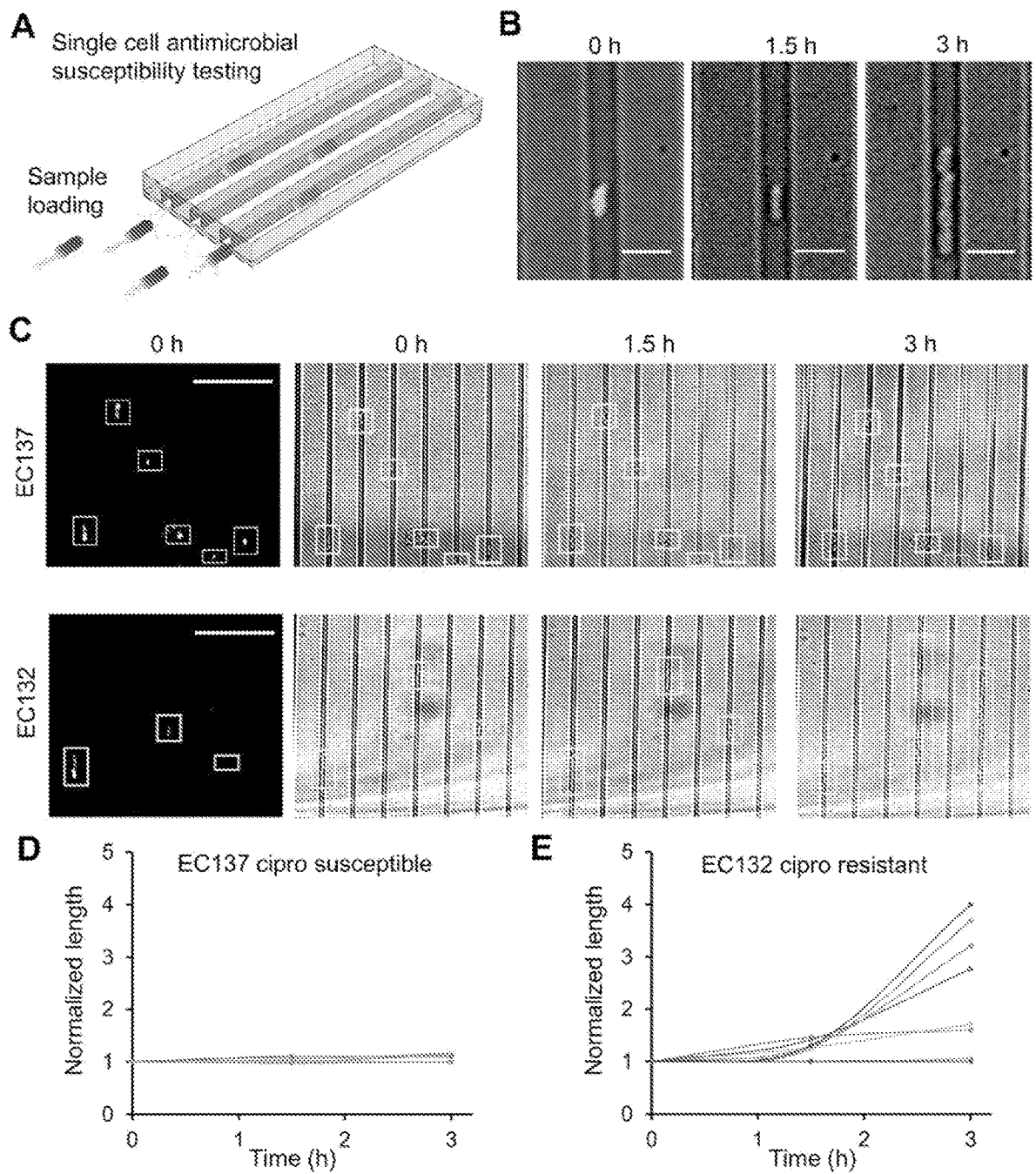

FIG. 23. Microfluidic single cell pathogen identification and antimicrobial susceptibility testing (AST). (A) Schematic of the microfluidic single cell AST device. Bacteria are loaded into the channels by capillary force. Physical trapping of the bacteria allows rapid phenotypic AST by monitoring the bacterial growth as the single cell level. (B) Overlay images showing pathogen identification and growth monitoring of a single bacterium (EC 137). Scale bars, 5 μm. (C) For single cell pathogen identification and AST, fluorescence detection was first performed at the beginning of the experiment. Time-lapse bright-field microscopy is performed to monitoring the growth kinetics of the bacteria in the microfluidic channel. Time-lapse images illustrate the growth of the two uropathogenic clinical isolates EC137 (ciprofloxacin susceptible) and EC132 (ciprofloxacin resistant). Boxes indicate bacteria trapped in the channel. Scale bars, 5 μm. (D-E) Representative growth curves of bacteria with and without antibiotics. Each curve represents the growth of a single bacterium.

Figure 24:
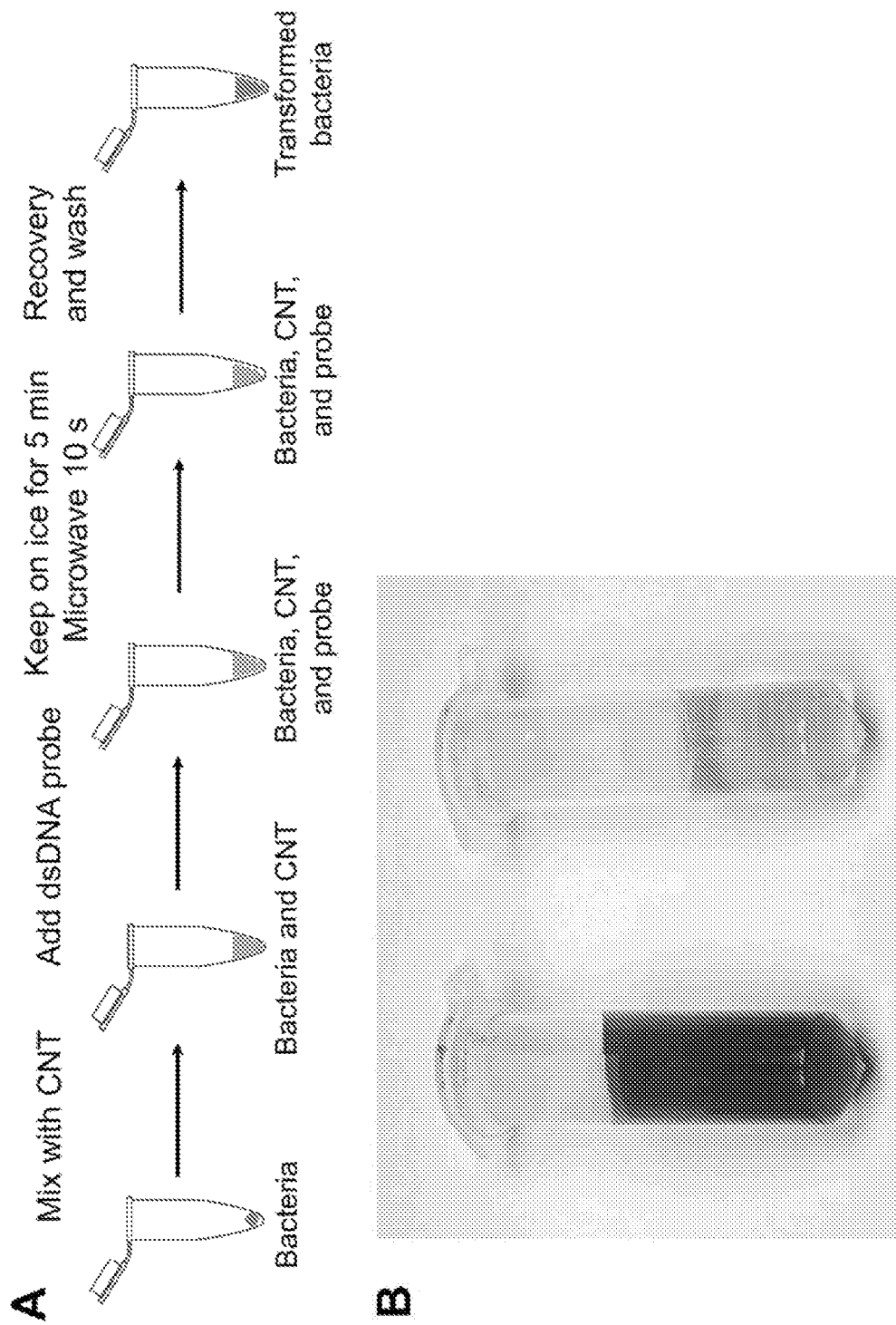

FIG. 24. Procedure of nanotube assisted microwave electroporation (NAME). (A) Multiwall carbon nanotube solution (30 mg/ml) was first filtered with a 1 μm microfilter. The bacterial pellet was mixed with 100 μl filtered carbon nanotube solution. Then 1 μl ($1.0 \times 10^5$ nM) of DNA probe was added and incubated for 10 minutes at room temperature. The solution was kept in ice for 5 minutes, and transformed in a microwave oven (700 W, 2.45 GHz) for 10 seconds. The sample was allowed to recover for 30 minutes and washed 3 times with PBS. (B) Image of multiwall carbon nanotubes before (left) and after (right) filtration.

Figure 25:
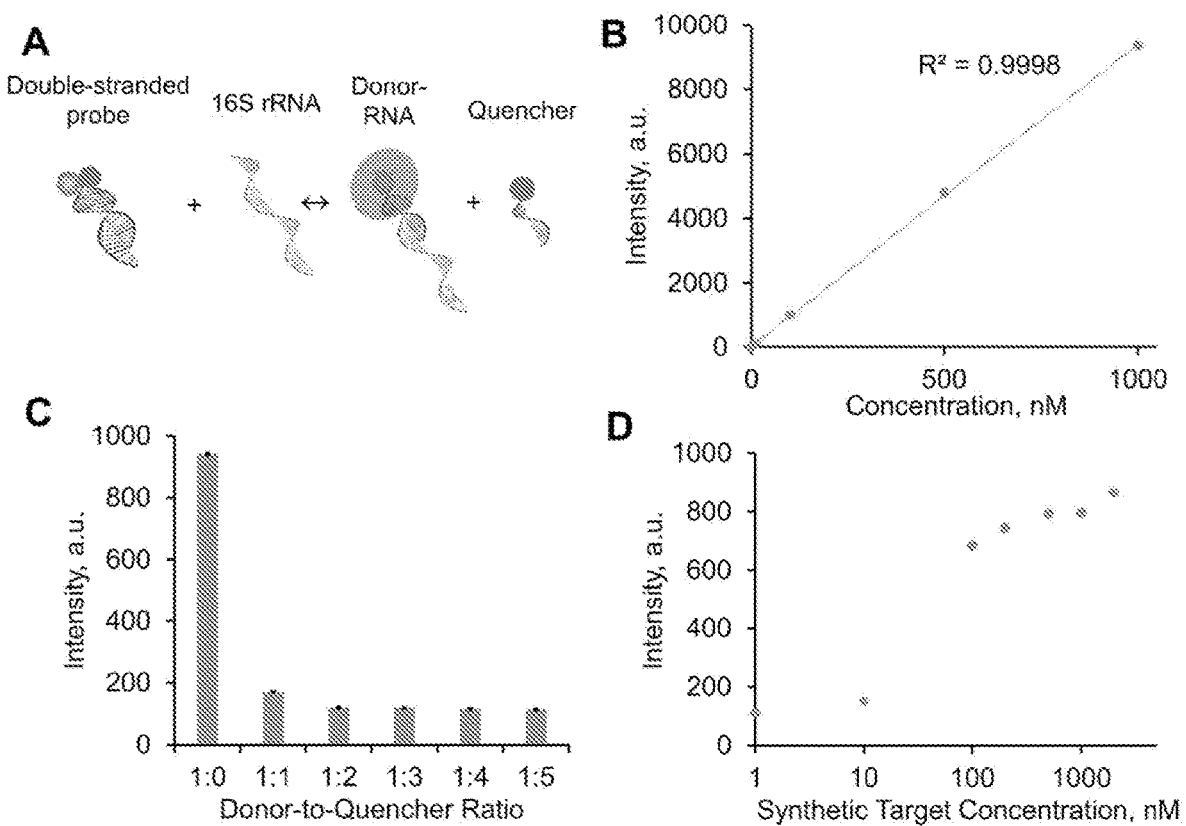

FIG. 25. Double-stranded DNA probe for detecting bacterial 16S rRNA. (A) Schematic of the double-stranded probe for intracellular sensing. The 16S rRNA displaces the quencher and hybridizes to the fluorophore labeled probe (donor probe), allowing pathogen identification. (B) Calibration of the donor strand. The error bars (SEM) are not visible in the graph due to the small values. (C) Optimization of the donor-to-quencher ratio. In the test, the concentration of the donor probe was 100 nM and the concentration of the quencher probe was adjusted to obtain different donor-to-quencher ratios. The probes were mixed in 1× TE buffer with 100 mM NaCl and heated in a water bath at 95° C. for 5 minutes. The solution was then allowed to cool down slowly to room temperature. A donor-to-quencher ratio of 1:3 was used in this disclosure. Data represent mean±standard error (n=5). (D) Dynamic range of the double-stranded probes for nucleic acid detection, which covers over 2 orders of magnitude. Data represent mean±standard error (n=5).

Figure 26:
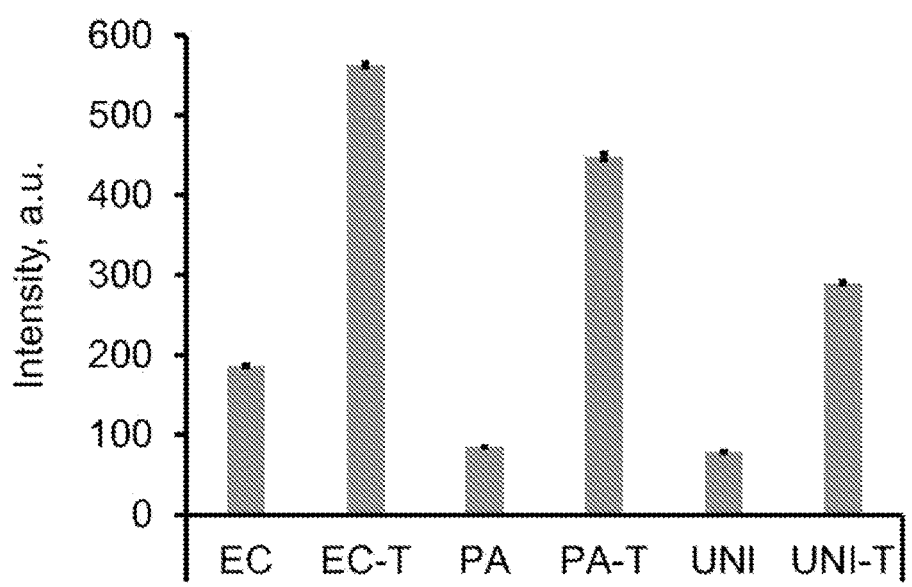

FIG. 26. Calibration of double-stranded DNA probes. Three probes (EC, PA, and UNI) were calibrated with the complementary synthetic targets (T). Concentrations of the probes and synthetic targets were 100 nM and 1000 nM, respectively.

Figure 27:
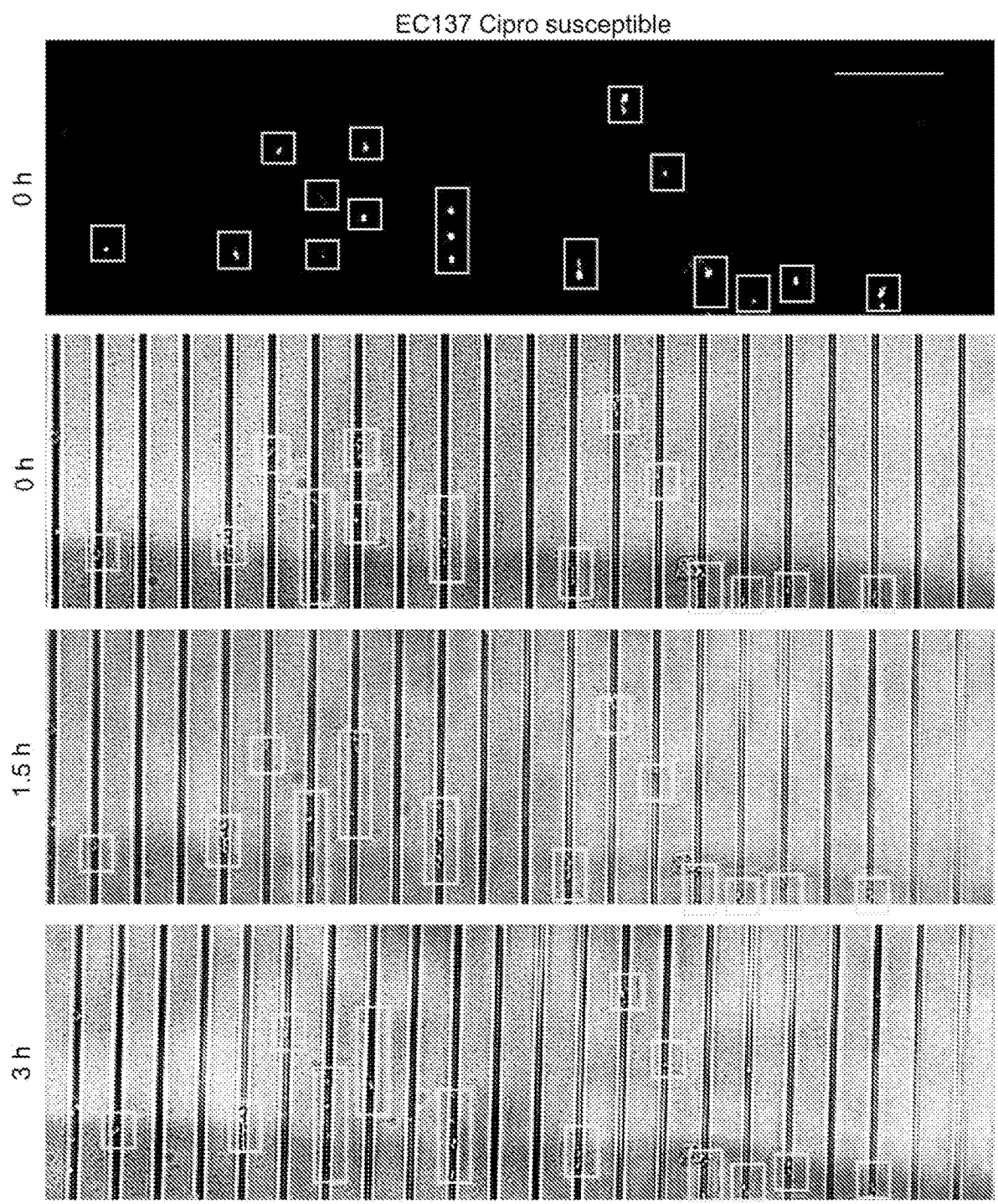

FIG. 27. Microfluidic single cell pathogen identification and antimicrobial susceptibility testing (AST). Single cell pathogen identification and AST of uropathogenic clinical isolates: Boxes highlighted selected bacteria trapped in the channels. Scale bars, 25 μm.

Figure 28:
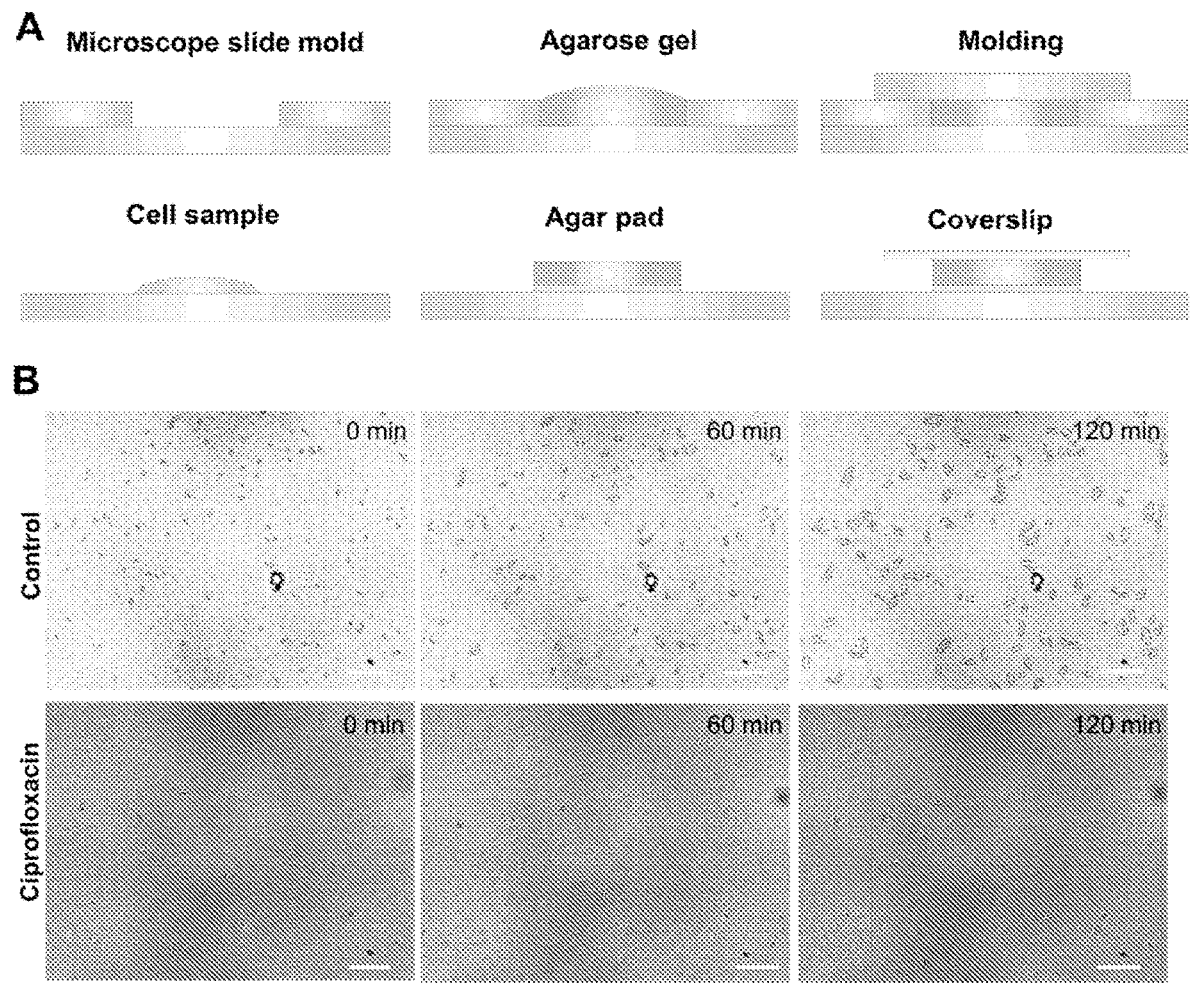

FIG. 28. Testing bacteria resistance with agar pads. (A) Schematics of the procedure for creating agar pads for single cell AST. Agar pad culture allows steady growth for long term observation. (B) EC137 growth with and without ciprofloxacin in agar pads. Ciprofloxacin inhibited the growth of the bacteria. Scale bars, 25 μm.

DETAILED DESCRIPTION

In a first aspect (Part I), this disclosure provides an adaptable microfluidic system that allows rapid classification of bacteria and antimicrobial susceptibility testing at the single cell level. The microfluidic system comprises bacteria trapping channels and pneumatic channels that can apply pressure to the bacteria trapping channels to, for example, decrease a size dimension of the bacteria trapping channels.

In a second aspect, (Part II) the disclosure provides an approach for single cell pathogen identification by transforming (i.e., delivering) molecular biosensors into viable bacteria using a nanotube assisted microwave electroporation (NAME) technique.

Part I and Part II of this disclosure are related to one another, and may be combined in certain implementations. All of description with respect to bacterial characterization from Part I and Part II apply equally to each of these Parts.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

Ranges of values are disclosed herein. Unless otherwise stated, the ranges include all values to the magnitude of the smallest value (either lower limit value or upper limit value) and ranges between the values of the stated range. These include but are not limited to all values for bacterial detection sensitivity and specificity, all time periods, temperatures, pressures, reagents, volumes, sizes (length, width, height, diameter, area), distributions, masses, concentrations, densities, ratios, such as aspect ratios, proportions, layers, methods of making the devices and systems described herein, and all methods of using the devices and system described herein. In embodiments, the disclosure comprises determining one or more physical attributes of bacteria, including but not necessarily limited to bacteria cell length, diameter, etc., and/or the presence of a polynucleotide within bacteria, such as ribosomal RNA. In embodiments, a physical characteristic of a single bacterial cell is determined. In embodiments, the length of any device, or component of the device, can be determined based at least in part on scale bars shown in the figures or this disclosure. In embodiments, movement of the bacteria is restricted due to pressure applied to the bacteria in a channel of a microfluidic device described herein. In embodiments, bacteria are distinguished from other bacteria based at least in part on bacterial cell length, or other size measurement(s). In embodiments, the existence of bacteria, and/or the size or shape of the bacteria, such as rod or spherical shape, and/or the presence of a polynucleotide sequence in the bacteria, is determined. In embodiments, distinct bacteria in a sample are identified. In embodiments, identification of bacteria is performed in a period of time, such period of time being shorter than previously available approaches.

The disclosure includes all devices and systems described herein during operation. For example, a microfluidic device described herein includes such a device with samples and/or bacteria present within one or more of its channels, as described further below, and includes all distributions of bacteria, and further may include any one or combination of antimicrobial agents, such as antibiotics, against which bacteria within the device can be tested for resistance.

The disclosure includes all polynucleotide and amino acid sequences described herein, and every polynucleotide sequence referred to herein includes its complementary DNA sequence, and also includes the RNA equivalents thereof to the extent an RNA sequence is not given. In embodiments, the disclosure includes bacteria which have a detectably labeled polynucleotide hybridized to a nucleic acid produced by the bacteria, such as a ribosomal RNA (rRNA), such as a 16S rRNA. In embodiments, the disclosure comprises one or more bacteria cells, wherein the bacteria are in physical contact with a carbon nanotube described herein, such as a multiwall carbon nanotube, and wherein the bacteria and/or the carbon nanotube is exposed to microwave energy, wherein a detectably labeled polynucleotide is introduced into the bacteria, such as in a double stranded probe, wherein the non-labeled probe is conjugated to a quenching compound, and wherein the introduction of the detectably labeled polynucleotide is enhanced by using the carbon nanotube and microwave energy.

All systems, devices, and methods as depicted herein, including all components of such systems and steps of the methods, alone and in all possible combinations, are included in this disclosure. Non-limiting examples of devices and device components are depicted in the figures of this disclosure. Variations on the devices and components will be understood by those skilled in the art, given the benefit of this disclosure.

Any result obtained using the devices, systems and methods of this disclosure can be compared to any suitable reference, such as a known value, or a control sample or control value, suitable examples of which will be apparent to those skilled in the art, given the benefit of this disclosure.

Part I

This Part of this disclosure relates to a microfluidic device that can be used to analyze bacteria. It is useful, as least because bacterial infection is a leading cause of morbidity and mortality and accounts for over $20 billion healthcare costs in the United States each year[1-3]. Previously available diagnostic methods of bacterial infection typically involve transport of patient samples to a clinical microbiology laboratory where a bacterial culture procedure, such as agar plate, blood tube, or sputum culture, is performed to test for the presence of bacterial pathogens. Morphological, biochemical, and molecular assays are used to identify the species and perform antimicrobial susceptibility testing (AST)[4-6]. These culture-based assays typically require 3-5 days. Without microbiological analysis, physicians often resort to prescribing broad-spectrum antibiotics based on the worst-case assumption of the most virulent bacteria[7, 8]. This practice results in improper and unnecessary treatment, disruption of the patients' microbial makeup, poor clinical outcomes, and the emergence of multidrug resistant pathogens[9]. Rapid microbiological analysis techniques are essential to properly manage infectious diseases and combat multidrug resistant pathogens[10-12].

Phenotypic culture is the current standard in clinical microbiology. Colony morphology (form, elevation, and appearance), Gram stain, and biochemical phenotyping are culture-based techniques to classify and identify the bacteria. Molecular approaches, such as multiplex PCR and mass spectroscopy, can be performed with isolated bacteria to identify strains[13-16]. To determine the antimicrobial resistance of the pathogen, the growth of the pathogen in the presence of antibiotics is interpreted and reported for therapeutic management of the patient[17-20]. Recently, biosensor platforms including optical, electrochemical, loop-mediated isothermal amplification, and biophysical biosensors, have been developed to detect bacterial growth for AST[21-32]. To improve sensitivity and accelerate AST, microfluidic approaches, such as digital microfluidics, agarose microchannels, electrokinetics, and microfluidic confinement, have been demonstrated for performing AST at the single cell level[33-40]. In particular, physical confinement of the pathogen allows rapid AST on a time scale comparable to the doubling time of the bacteria[39, 40]. Nevertheless, these techniques neither provide information about the bacterial species nor distinguish polymicrobial samples from one another[41]. Furthermore, prior to the present disclosure, most existing techniques require cultured isolates and have been optimized based on a small panel of pathogens, thereby limiting their general applicability for infectious disease diagnostics. Thus, Part I of this disclosure provides in non-limiting embodiments an adaptable microfluidic system that determines the presence of bacterial pathogens, classifies the species based on their physical features, and performs phenotypic AST at the single cell level. In particular, an adaptable microchannel with tunable pneumatic valves, such as the pneumatic channels described herein, physically traps bacteria and separates the bacterial species according to their physical size and shape in as little time as five minutes. By monitoring growth of individual bacteria in the presence of an antibiotic, antimicrobial resistance can be determined rapidly. The performance of the adaptable microfluidic system is evaluated using clinical isolates, blood cultures, urine, and whole blood samples. To evaluate the clinical feasibility of the microfluidic system for rapid pathogen classification and AST at the single cell level, 25 clinical samples with blinded pathogens were tested.

In certain aspects, Part I of this disclosure provides the following:

A microfluidic device for characterizing bacteria, the device comprising: i) one or more bacteria trapping channels, and ii) one or more control channels, such as pneumatic channels, proximal to the bacteria trapping channels, wherein each of the one or more control/pneumatic channels is capable of changing a size dimension, such as height, of a bacteria trapping channel. In embodiments, a control channel comprises a pneumatic channel that decreases the height of a trapping channel. In embodiments, a trapping channel is open, unless pressure is applied by a control chancel. In embodiments, one or more trapping channels are closed until negative pressure is applied by a control channel.

In embodiments the one or more channels comprise pneumatic channels, and can apply a pressure of greater than 0 kPa, up to 300 kPa, to the bacteria trapping channel. In embodiments, the height of the bacteria trapping channel can be adjusted to from about 0 µm to about 2.0 µm in width or height by applying pressure on the bacteria trapping channel using the pneumatic channel proximal to the bacteria trapping channel. In embodiments, for common bacterial pathogens, trapping can occur in a range of width from 1.5-2.0 µm. In embodiments, the microfluidic device comprises a plurality of the bacteria trapping channels, and/or comprises a plurality of the pneumatic channels. In embodiments, the microfluidic device may further comprise additional channels with greater dimensions, such as to trap eukaryotic cells, such as mammalian cells, or fungal cells. In embodiments, a channel comprises a plurality of sessions, such as a large session on the order of 10 um to trap mammalian cells (e.g., white blood cells) and a medium size session (~5 um) to trap fungal cells.

In embodiments, the device comprises from 1-5 pneumatic channels that are proximal to the one or more bacteria trapping channels. In embodiments, the microfluidic device is comprised in whole or part by a chip. In embodiments, a multiplex chip device comprises from 10-1000 bacteria trapping channels/cm. In embodiments, a chip comprises from 5000-10000 channels. In embodiments, one or more devices/chips of this disclosure are provided in a high throughput format, such as a 96 well plate, and thus may constitute a high throughput system or array comprising from 100,000 to 500,000 channels.

Representative examples and configurations of bacteria trapping channels and pneumatic channels are described below, and are illustrated in the figures of this disclosure. In embodiments, bacteria trapping channels are arranged in series, such as parallel to one another. In embodiments, pneumatic channels are disposed across the parallel trapping channels, i.e., the pneumatic channels may be of a contiguous form that is perpendicular to and across the parallel series of trapping channels, but other configurations are included.

In more detail, FIGS. 1F, 1G, 5C, 5D and 5E illustrate certain features of a microfluidic device of this disclosure, but are not intended to be limiting. In particular, FIG. 1(F), which is related to FIG. 1A and other figures and description herein, shows three different bacteria shapes and sizes shown in broken lines. FIG. 1F thus shows the microfluidic device 100, a microfluidic bacteria trapping channel 102 having representative bacteria within the channel, a right side 101c of a bacteria trapping channel 102 relative to an inlet 105, the inlet being configured to permit bacterial single cells of a variety of sizes and shapes to enter to microfluidic bacteria trapping channel 102, such as via capillary force, a bottom 101d, an outlet 101b, a first pneumatic control channel 103 positioned perpendicularly to the microfluidic bacteria trapping channel 102 and configured to controllably apply pressure to deform the microfluidic bacteria trapping channel 102, and a second pneumatic control channel 104, also positioned perpendicularly to the microfluidic bacteria trapping channel 102, the second pneumatic control channel 104 also configured to apply pressure to deform the microfluidic bacteria trapping channel 102. The first pneumatic control channel 103 and the second pneumatic control channel 104 may each be separately configured to apply the same or distinct pressures to the microfluidic channel 102, and may be configured to apply concurrent same or distinct pressures, and/or to apply the same or distinct pressure at different time points, processes that may be performed once or more than one time for any particular sample. The bottom 101d may be transparent, and may be comprised by, for example, a glass substrate, including but not limited to a microscope slide, or any other transparent material. The microfluidic device may also comprise a top (not shown) that covers at least the bacteria trapping channels 102. The top may also be transparent, and may be comprised, by example, of glass or any other transparent material. FIG. 1G, which is also related to FIG. 1A, shows a front view of microfluidic device 100. The first pneumatic control channel 103, and three microfluidic bacteria trapping channels 102 configured to trap bacteria are shown, along with a right side 101c of a bacteria trapping channel 102, a left side 101a of a bacteria trapping channel 102, and the bottom 101d. FIG. 1H, which is also related to FIG. 1A, provides a top view of the microfluidic device 100. Shown is the left side 101a of a bacteria trapping channel 102, the right side 101c of a bacteria trapping channel 102, three microfluidic channels configured to trap bacteria 102, the first pneumatic control channel 103, the second pneumatic control channel 104, the outlet 101b, and three inlets 105. As can be seen from the bacteria drawn in broken lines, which enter the microfluidic device 100 via the inlets 105, application of different pressures ($P_0$, $P_1$ and $P_2$, designated as such alphanumerically and by the arrows) allow different types of bacteria as indicated by distinct size and shapes to be trapped in the microfluidic channels 102 by application of distinct pressures to the microfluidic channels 102 by the first pneumatic channel 103 and second pneumatic channel 103. Likewise, FIG. 5D, which is related to FIG. 5A, shows the microfluidic device 100, the left side 101a of a bacteria trapping channel 102, the right side 101c of a bacteria trapping channel 102, three inlets 105, three microfluidic bacteria trapping channels configured to trap bacteria 102, a first pneumatic channel 103, and an outlet 101b. Single cell bacterium are individually shown schematically with broken lines. (E) Related to FIG. 5A. Shown is the microfluidic device 100, three microfluidic bacteria trapping channels 102, the left side 101a of a microfluidic bacteria trapping channel 102, the right side 101c of a microfluidic bacteria trapping channel 102, three inlets 105, a first pneumatic channel 103, and an outlet 101b. The inlets 105 and the outlets 101b allow for evaporation of liquid in the bacteria trapping channels. Single cells of bacteria that have been trapped in two of the microfluidic bacteria trapping channels 102 are shown schematically with broken lines, as is a single bacterium that was able to pass through the microfluidic bacteria trapping channel 102 despite the pressure applied by the first pneumatic channel 103 because of the smaller size of the single un-trapped bacterium.

The bacteria trapping channels and pneumatic channels can be formed of any suitable material, non-limiting examples of which are described herein. In general, the bacteria trapping and pneumatic channels are flexible across their entire length, or at least across a segment, such that the trapping channels can be compressed by the pneumatic channels. In embodiments, the trapping and/or pneumatic channels are formed of a flexible, optically clear composition, such as a silicone based composition. In embodiments, none of the pneumatic channels, and/or the bacteria trapping channels, are gas permeable. In embodiments, the channels are formed from one or more polymeric organosilicon compounds. In embodiments, the channels are formed from any suitable polymeric material, such as polydimethylsiloxane (PDMS), Polyimide, hydrogels, epoxies, or PMMA, or combinations thereof. In embodiments, the channels are formed using any suitable technique, including but not limited to photolithography, and/or reactive ion etching. In embodiments, a microfluidic device of this disclosure comprises a glass slide. In embodiments, a device of this disclosure comprises an optically transparent window. In embodiments, the disclosure provides for readout of a signal from a trapping chamber that is optically accessible (e.g. quartz on silicon or other transparent material, including the channel itself), such as with an imager located proximal to the trapping chamber. In embodiments, free-space optics may be used to detect a signal from a trapping chamber using any suitable signal detection device that is placed in proximity to the location where a detectable signal is generated, such as a CCD camera. In embodiments, a microfluidic device of this disclosure comprises an optical waveguide to transmit a signal to any suitable measuring device such that optical accessibility to the trapping chamber is not necessarily required to detect the signal. In embodiments, lens-less optics, and/or a cell phone based imaging approach is used. In embodiments, one or more segments of a bacteria trapping channel can be connected to or in communication with a digital processor and/or a computer running software to interpret the position, number, size, growth rate, density, or other bacterial characteristics. A processor may also be included as a component of the device or system comprising the device, wherein the processor runs software or implements an algorithm to interpret an optically detectable signal, and generates a machine and/or user readable output. In an embodiment, a microfluidic device described herein can be integrated or otherwise inserted into an adapter that comprises a detection device, such as a camera, or a microscope, including but not limited to a light microscope, or a scanning electron microscope, or a fluorescent microscope. In embodiments, a computer readable storage medium can be a component of a device of this disclosure, and can be used during or subsequent to performing any assay or one or more steps of any assay described herein. In embodiments the computer storage medium is a non-transitory medium, and thus can exclude signals, carrier waves, and other transitory signals.

In embodiments, a sample used in a microfluidic device (or in Part II of this disclosure) described herein comprises any suitable biological sample that can comprise bacteria. In embodiments, a liquid biological sample is used. In embodiments, the liquid biological sample comprises blood, urine, lacrimal secretions, seminal fluid, cerebrospinal fluid, or any other biological fluid. In embodiments, for Part I or Part II of this disclosure, the sample is used directly, or is subjected to a processing step prior to being analyzed using as described herein. In embodiments, the sample tested is from a human, or a non-human animal, and is thus suitable for human and veterinary diagnostic purposes. In embodiments, a sample tested using a device of this disclosure comprises a food sample. In embodiments, a sample comprises a swab, or liquid sample obtained from any environment, surface, or device, including but not limited to aqueous based samples, such as drinking water, and samples taken from any material. In embodiments, the device is configured to distinguish pathogens that can be adapted for use as biological weapons In embodiments, and as described further below and illustrated by the drawings of this disclosure, the sample is subjected to a mechanical pressure that causes a fluid component and/or bacteria to pass through a segment of a bacteria trapping channel described herein, subsequent to which the bacteria is trapped, i.e., its movement through the channel is restricted or stopped. In embodiments, movement of bacteria is stopped, or does not occur, due it the bacteria adhering to a substrate in the device. It will be recognized that the term "bacteria" is used to refer to more than one bacterium. The microfluidic device is configured to characterize single cells, and thus one or more individual bacterium are trapped and analyzed using the device. In embodiments, more than one bacterium may be present in a bacterial trapping channel, but in embodiments, only a single bacterium is trapped and/or analyzed.

In embodiments, mechanical pressure used to stop or restrict movement of bacteria (including an individual bacterium) comprises pneumatic pressure supplied by the pneumatic channels described herein. In embodiments, the sample migrates at least partially via capillary action. In embodiments a wicking material can be included. In embodiments, evaporation of a liquid component of the sample contributes to the movement of bacteria through at least a portion of a bacteria trapping channel. In embodiments, evaporation occurs at both ends (e.g., an inlet and an outlet) of a single bacteria trapping channel.

In embodiments, the disclosure comprises a method comprising introducing a liquid biological sample into a microfluidic device as described herein, and identifying one or more characteristics of one or more bacteria that are trapped in a bacteria trapping channel, or identifying an absence of bacteria. In embodiments, a trapped bacterium is accordingly analyzed. In embodiments, bacteria are trapped in a trapping channel on which no pressure is applied by the pneumatic channel. In embodiments, a bacterium is trapped in a bacteria trapping channel in an area on which from 50-200 kPa of pressure is applied. In embodiments, a spherical bacterium is trapped in a bacterial trapping channel using a pressure of ≤50 kPa. In embodiments, a single rod shaped bacterium is trapped in a bacterial trapping channel using a pressure of >50 kPa to 200 kPa. In embodiments, the disclosure provides for distinguishing rod-shaped bacteria types in the sample based on determining trapped bacteria using a pressure of about 90 kPa and about 150 kPa in a single, or in distinct channels.

In embodiments, identification and/or characterization of a bacterium and/or bacteria is complete within a period of from 2 minutes to 60 minutes, inclusive and including all ranges of time to the second between 2 and 60 minutes. In embodiments, antimicrobial sensitivity is determined in a period of from 15-60 minutes. In embodiments, antimicrobial sensitivity is determined in a period of no more than 30 minutes. In embodiments, the sample volume introduced into the device is from 1 μl to 100 μl. In embodiments, the volume is about 20 μl. In embodiments, from about $10^2$ to $10^8$ cfu/mL, inclusive, and include all numbers and ranges of numbers there between, of bacteria are introduced into the device. In embodiments, samples are introduced into the microfluidic device without use of a pump or a pressure source. Thus, in an embodiment, the bacteria are introduced into the device using a force that comprises or consists of capillary flow. In certain embodiments, the disclosure provides for determining the presence or absence of bacteria in one or more samples. In embodiments, use of a microfluidic device of this disclosure provides for correctly determining the presence of bacteria in from 80-100% of samples. In embodiments, the presence of one more bacteria and/or more than one type of bacteria in a sample is correctly determined for 90, 91, 92, 93, 94, 95, 96, 97, 98, 99 or 100% of samples. These percentages may be for any number of samples, such as from 10-10,000 samples, or more. In embodiments, correctly classifying bacteria using a microfluidic device of this disclosure is performed with from 80-100% sensitivity, and with 50-100% specificity, including all numbers and ranges of numbers to the second decimal point between 80-100% for sensitivity, and 50-100% for specificity. In embodiments, particular and non-limiting embodiments, sensitivity is at least 94%. In embodiments, specificity is at least 57%. In embodiments, the device facilitates a positive predictive value of about 85% and negative predictive value of about 80% over a series of samples. In embodiments, the disclosure provides for determining the presence or absence of pathogenic and/or antibiotic resistant bacteria and/or a single bacterium in a sample. In embodiments, the disclosure provides for discriminating between strains of the same bacteria, such as by determining the type of bacteria and/or whether or not antibiotic resistant and/or non-resistant bacteria are present. In embodiments, the disclosure provides for determining whether bacteria and/or a single bacterium in a sample are/is rod-shaped or spherical. In embodiments, the disclosure provides for determining a shape and/or type of trapped bacteria and/or a single bacterium based on an aspect ratio (length/width). In embodiments, the disclosure provides for classifying bacteria based on threshold values, such as a pre-set aspect ratio, and/or a threshold trapping pressure for any type of bacteria, such as a minimum trapping pressure defined as the lowest pressure that traps over 75% of bacteria of a particular type or characteristic. In embodiments, the disclosure provides for determining whether or not a sample contains multiple, distinct bacterial populations, such as based on size, shape, growth rate, antimicrobial resistance, or a combination thereof, to thereby identify the sample as polymicrobial. Such determination can be made on a cell by cell basis, e.g., by identifying a series of single bacterium from a sample. In embodiments, the disclosure provides a bacterial signature resulting from determining multiple characteristics of bacteria. In embodiments, one or more properties of bacteria that are analyzed using a microfluidic device of this disclosure are determined using a visual analysis, such as a visual analysis of bacteria that are trapped in a bacteria channel using any suitable microscope.

In embodiments, the bacteria (or a single bacterium, or a series of bacteria wherein each bacterium is separately analyzed) are characterized according to any device and/or method described herein being any of, or any combination of, *Streptococcus*, *Staphylococcus*, *Clostridium*, *Bacillus*, or *Salmonella*. In embodiments, the bacteria are *Escherichia coli* (*E. coli*), *Staphylococcus epidermidis* (*S. epidermidis*), and *Mycobacterium bacteremicum* (*M. bacteremicum*). In embodiments, bacteria are identified as members of a group. In non-limiting embodiments, *Staphylococcus*-like, *Enterococcus*-like, *Pseudomonas*-like, *Klebsiella*-like, and *E. coli*-like groups are identified. In embodiments, bacteria capable of forming a biofilm are determined. In embodiments, samples comprising any of the following bacteria are used, wherein such bacteria are identified and/or distinguished from other bacteria or bacteria types: *Pseudomonas*, *S. aureus*, Enterobacteriacea (*Klebsiella* spp., *E. coli*, *Enterobacter* spp., *Serratia* spp., *Citrobacter* spp.), *Streptococcus* spp., *Hemophilus* spp., *Acinetobacter* spp., *Neisseria* spp., *Stenotrophomonas maltophilia*, *Corynebacterium*, *Moraxella*, and *Enterococcus*, *Haemophilus ducreyi*, *Chlamydia trachomatis*, *Neisseria gonorrhoeae*, *Mycoplasma Genitalium*, and *Treponema pallidum*.

In embodiments, the disclosure provides for determining the presence, absence, amount, and/or antibiotic resistance for any type of antibiotic. In embodiments, the disclosure provides for determining antimicrobial susceptibility (AST) for one or more trapped bacteria. Thus, characterization of any property of a bacterium, including but not limited to AST, can be performed on a bacterium that is trapped in a bacteria trapping channel. AST analysis can be performed by, for example, providing bacteria in the trapping channels with an antibiotic, and determining whether or not the antibiotic is lethal to the bacteria, such as by lysis, and/or inhibits an increase in size of the bacteria, or inhibits division of the bacteria. Resistance and sensitivity to any antibiotic can be tested. In embodiments, the disclosure relates determining antibiotic resistance or sensitivity to any of narrow-spectrum beta-lactam antibiotics of the penicillin class of antibiotics. In embodiments, the antibiotic comprises ciprofloxacin. In embodiments, the antibiotic is methicillin (e.g., meticillin or oxacillin), or flucloxacillin, or dicloxacillin, or some or all of these antibiotics. In embodiments, the antibiotic is vancomycin. In embodiments, the antibiotic is linezolid (ZYVOX), daptomycin (CUBICIN), quinupristin/dalfopristin (SYNERCID). In embodiments, resistance (or susceptibility) to an antimicrobial peptide is used. In embodiments, resistance to any of the following types of antimicrobial agent is determined: Arsphenamine, Penicillin, Sulfonamide, Cephalosporin, Chlortetracycline, Polymyxin, Chloramphenicol, Nitrofurans, Bacitracin, Streptomycin, Metronidazole, Rifamycin, Novobiocin, Cycloserine, Streptogramin, Vancomycin, Isoniazid, Erythromycin, Pleuromutilin, Fosfomycin, Fusidic acid, Lincomycin, Trimethoprim, Nalidixic acid, Oxazolidinone, Carbapenem, Fidaxomicin, Mupirocin, Daptomycin, Monobactam, Bedaquiline, or Delamanid.

In embodiments, identification and/or characterization of bacteria is complete within a period of from 2 minutes to 60 minutes, inclusive and including all ranges of time to the second between 2 and 60 minutes. In embodiments, antimicrobial sensitivity is determined in a period of from 15-60 minutes. In embodiments, antimicrobial sensitivity is determined in a period of no more than 30 minutes. In embodiments, the sample volume introduced into the device is from 1 µl to 100 µl. In embodiments, the volume is about 20 µl. In embodiments, from about $10^2$ to $10^8$ cfu/mL of bacteria are introduced into the device.

In non-limiting embodiments, microfluidic channels provided with a device of this disclosure have any suitable dimensions. In embodiments, the width and/or height of microchannels used for trapping bacteria is about from 1.0 to 5.0 µm, including all numbers and ranges of numbers there between to the first decimal point. In an embodiment, the width of a microchannel is about 2.0 µm. In embodiments, the height of the microchannels is from 1.20-1.50 µm. In a non-limiting embodiment, the height is about 1.32 µm. In embodiments, the height of the microchannel is about 1.32 µm without pressure, and between 0.8 µm-0.3 µm under pressure. In non-limiting embodiments, the height of the microchannel that is used to trapped bacteria is about 0.64, or about 0.42 µm, under increased pressures.

In certain embodiments a result obtained from using a method and/or device and/or system of this disclosure can be compared to any suitable reference, examples of which include but are not limited control sample(s), a standardized curve(s), and/or experimentally designed controls such as a known input bacteria value used to normalize experimental data for qualitative or quantitative determination of the presence, absence, amount, or type of bacteria, or a cutoff value. A reference value may also be depicted as an area on a graph. In embodiments the disclosure provides for an internal control that can be used to normalize a result.

In certain embodiments a result based on a determination of the presence, absence, amount, type of bacteria, antibiotic resistance thereof, or a combination thereof, using an approach/device of this disclosure is obtained and is fixed in a tangible medium of expression, such as a digital file, and/or is saved on a portable memory device, or on a hard drive, or is communicated to a web-based or cloud-based storage system. The determination can be communicated to a health care provider for diagnosing or aiding in a diagnosis, such as of a bacterial infection, and/or for recommending or not recommending a particular antibiotic, or for monitoring or modifying a therapeutic or prophylactic approach for any bacterial infection.

In embodiments, the disclosure provides for monitoring treatment of an individual, such as by testing a first sample for the presence of bacteria, treating the individual with an antimicrobial agent, and testing a second sample to determine if the antimicrobial treatment is effective by determining less of, or the absence of the bacteria.

In embodiments, efficacy of candidate antimicrobial agents can be used by, for example, exposing a population of bacteria to the candidate antimicrobial agent, and testing the population using any method and/or device described herein to determine if the test agent is capable of inhibiting the growth and/or killing the bacteria. In embodiments, the bacteria comprise persister cells and/or dormant viable but non-culturable (VBNC) cells.

In certain examples the disclosure comprises an article of manufacture, which in embodiments can also be considered kits. The article of manufacture comprises at least one component for use in the bacterial analysis described herein, and packaging. The packaging can contain any device described herein. In various embodiments, the article of manufacture includes printed material. The printed material can be part of the packaging, or it can be provided on a label, or as paper insert or other written material included with the packaging. The printed material provides information on the contents of the package, and instructs user how to use the package contents for bacteria analysis.

The following description provides Part I examples, which are not intended to be limiting.

Design of the Adaptable Microfluidic System of Part I

Figure 7:
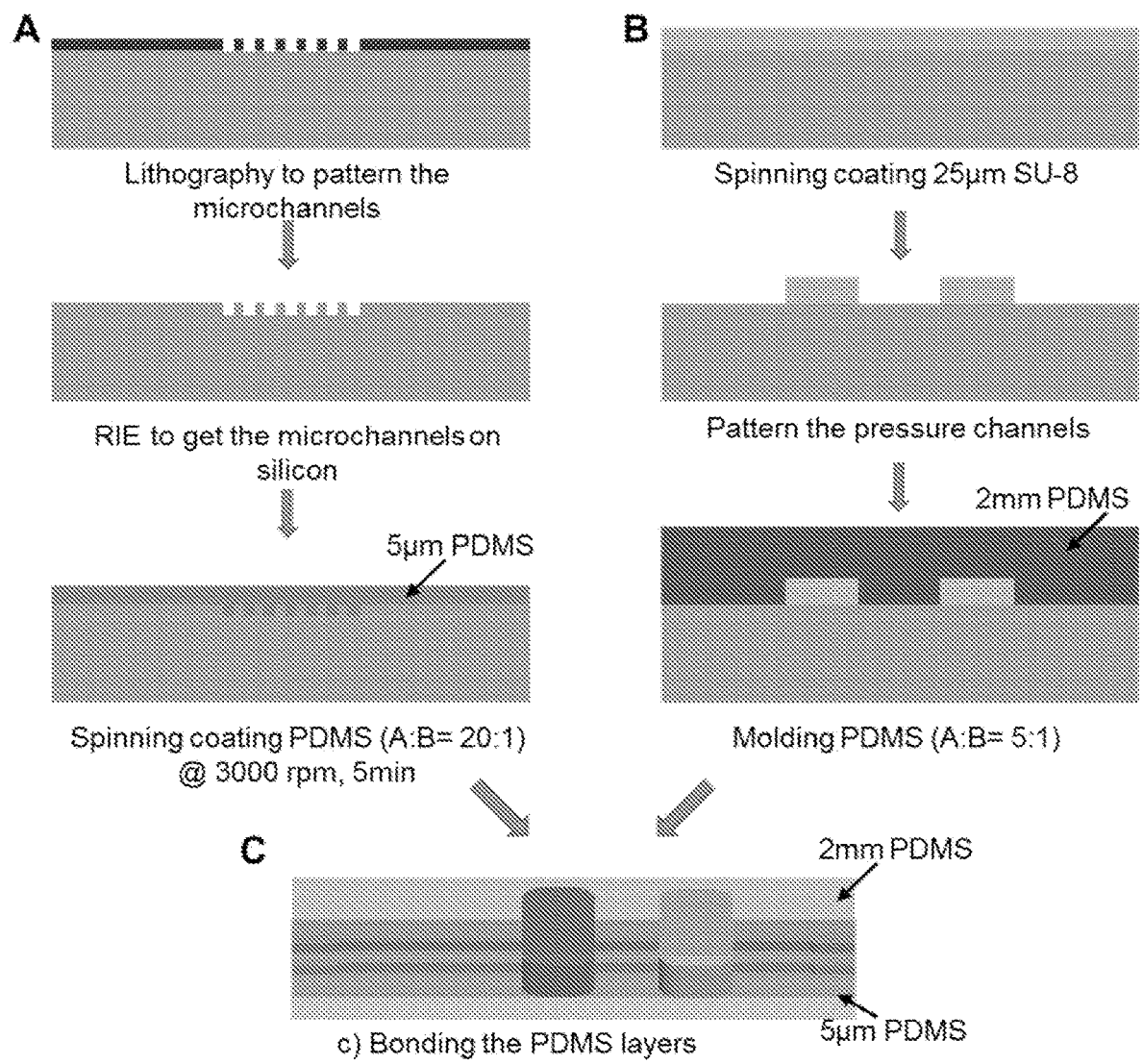
FIG. 7. Fabrication of adaptable microfluidic devices for single pathogen classification and AST. (A) Silicon masters were fabricated by photolithography and reactive ion etching (ME). PDMS molding was performed on the master to create the bacteria trapping channels. (B) Pneumatic control layers were fabricated by PDMS molding on SU8 molds. (C) The pneumatic control layer was bonded on top of the bacteria trapping layer by air plasma treatment. The bacteria trapping layer was sealed with a glass slide by a second air plasma treatment step.
Figure 8:
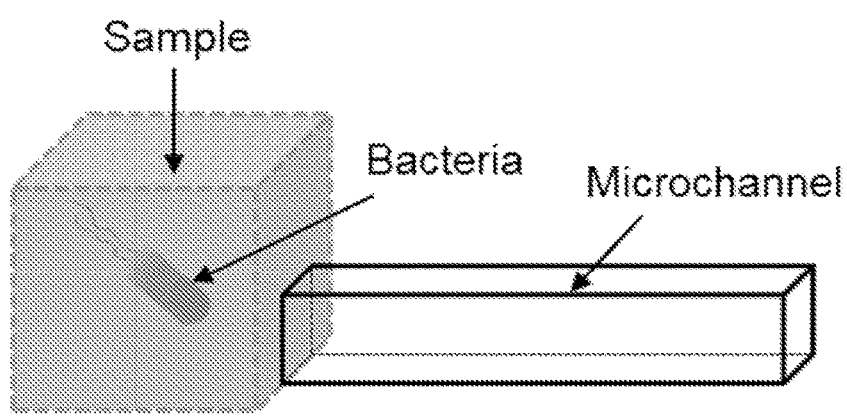
FIG. 8. The sample loading process. (A) To perform single cell AST, samples are loaded in the inlet of the microfluidic system. Evaporation gradually concentrates the sample and drives the bacteria into the channel by capillary force. (B) The microfluidic channels also serve as a physical filter to eliminate larger cells and impurities in the sample from the bacteria to facilitate the observation of single cell growth.
Figure 8:
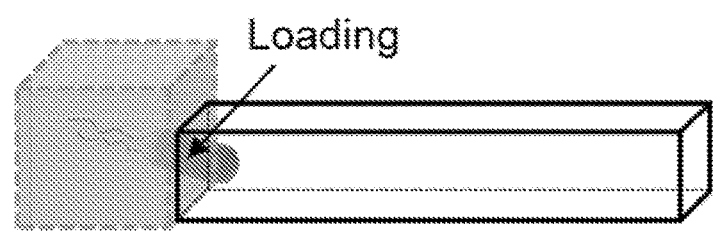
Figure 8:
Figure 8:
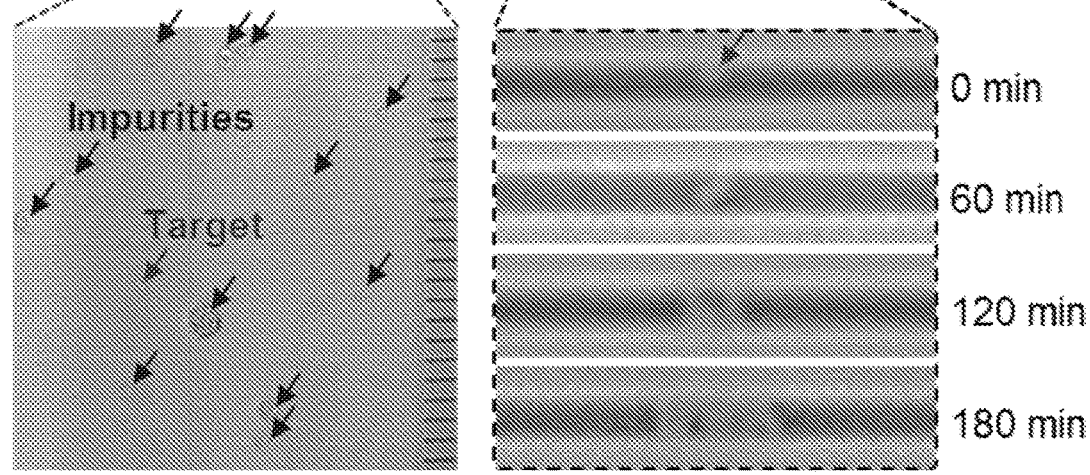

In one embodiment, an adaptable microfluidic design of this disclosure comprises parallel trapping channels under a second layer of pneumatic control channels, which regulate the height of the trapping channel for adapting to various bacteria (FIG. 7). The loading process is based on real-time monitoring of bacteria trapped in the channel (FIG. 1A and FIG. 8). In this example, a sample of 20 μl was loaded in the inlet of the microfluidic system and filled the channel by capillary force. As evaporation occurred at the outlet, the bacteria were continuously driven into the channels. Evaporation also occurred at the inlet, which gradually concentrated the sample. With a large pressure (e.g., 200 kPa), bacteria were trapped at the entrance of the observation window, which determined the presence of bacteria. To estimate the size of the bacteria, the pressure was released and the bacteria moved inward into the trapping region with a velocity on the order of 10 μm/s. Pressure was then applied and adjusted to trap the bacteria within the channels. After bacteria loading, culture medium was applied on both sides of the channels to balance the hydrodynamic force and prevented further loading of bacteria.

In Part I of this disclosure, at least five bacteria types, and/or a plurality of bacterial strains, such as at least 50 bacterial strains, are considered for pathogen classification and AST. For a given sample, the trapping time is increased to capture a sufficient number of bacteria. Using this protocol, we have demonstrated trapping of samples with bacteria from $5\times10^3$ to $10^8$ cfu/ml. For instance, less than 3 minutes were required to trap a sample with $10^7$ cfu/ml. Tens of bacteria could be trapped in approximately 10 minutes for samples with a concentration of $5\times10^5$ cfu/mL (as suggested in the CLSI guideline) (42). The loading time was increased to 30 min for handling samples with $5\times10^3$ cfu/mL. The trapping channels also serve as a physical filter to eliminate large cells and debris in physiological samples. This loading process selectively loads target pathogens into the channels and minimizes clogging issues resulting from the sample matrix (FIG. 8). This loading process examines the predominating species in the sample and inherently avoids false positive results due to flora, which typically has a low concentration.

Figure 9:
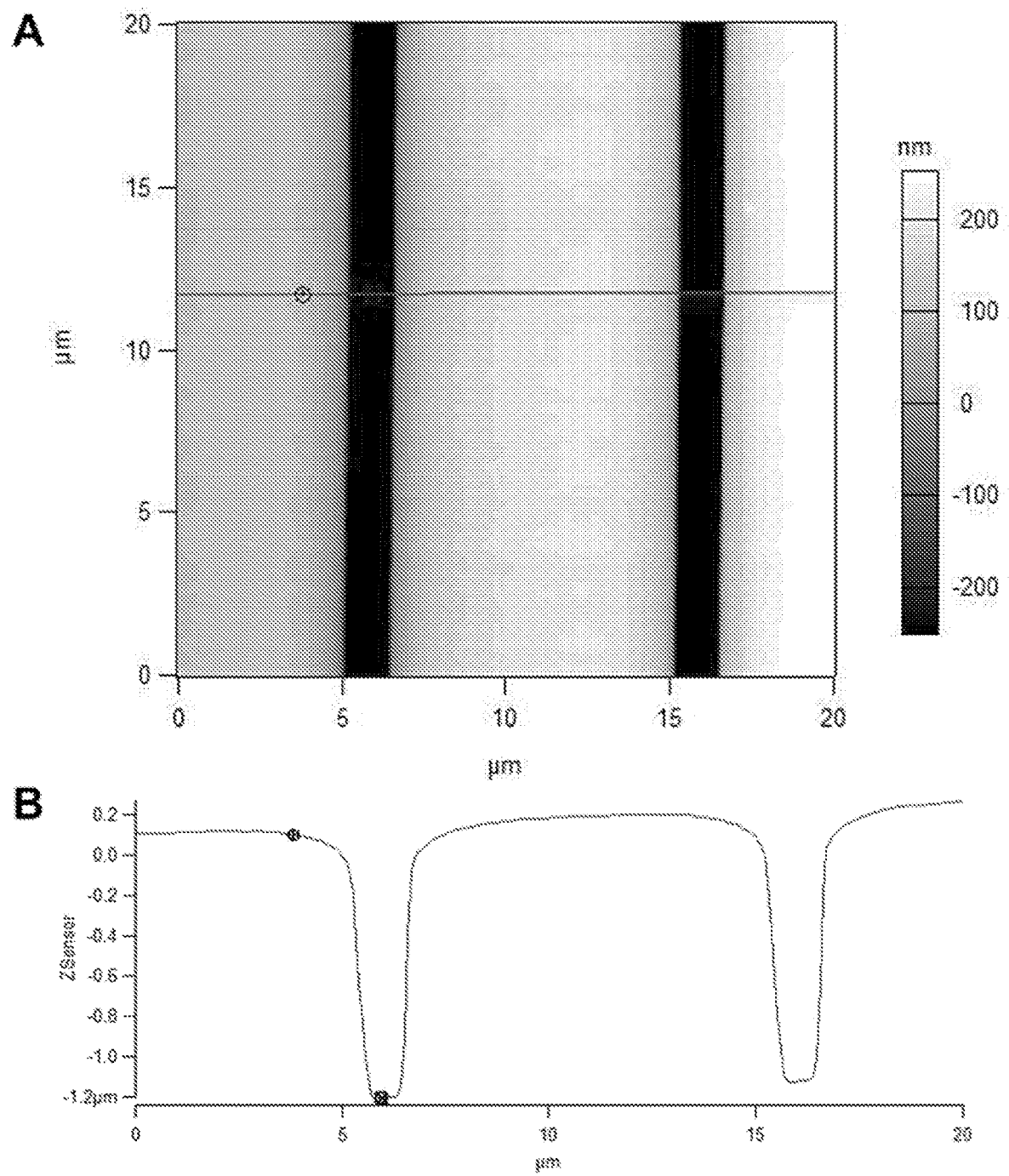
FIG. 9. Characterization of the dimension of the bacteria trapping channel by atomic force microscopy. (A) AFM image of the bacteria trapping layer. Red line indicates the position of the surface profile in B. (B) Surface profile along the measuring line. The depth of the microchannel was estimated by the height difference between the blue dots.
Figure 10:
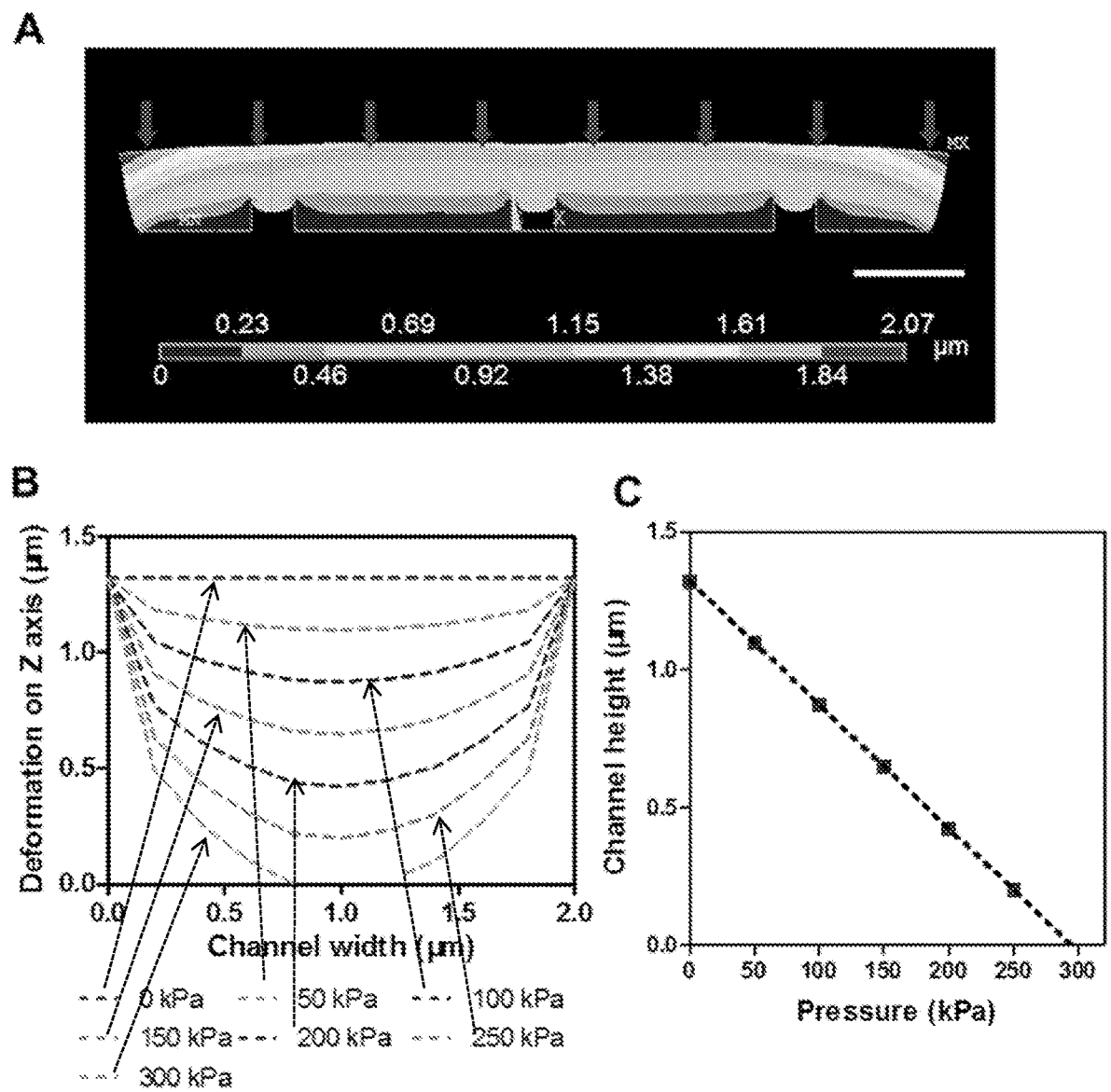
FIG. 10. Pneumatic control of the height of the bacteria trapping channel. (A) Finite element analysis (ANSYS) of the bacteria trapping channel under 150 kPa pressure. (B) The cross-sectional profiles of the bacteria trapping channel with different applied pressures in the pneumatic control layer. (c) The height of the bacterial trapping channel decreases linearly with the pressure.

Confinement and classification of bacteria were performed by manually pneumatically adjusting the dimensions of the trapping channels (FIG. 1B), which comprise built-in pressure sensors. Alternatives to manually applying pressure can be used, such as by automation with a computerized and/or electronic pressure regulator with feedback control, and other features that will be apparent to those skilled in the art, given the benefit of the present disclosure. The channel dimensions and cross-section profile were studied with atomic force microscopy and finite element analysis (FIGS. 9-10). The height of the trapping channel could be adjusted from 0 to 1.3 μm with a pressure between 300 and 0 kPa. Bacteria are trapped when the channel dimensions match the dimension of the pathogen. This feature enables pathogen classification for species with different physical size. Trapping bacteria in the pneumatic control channel region also facilitates follow-up time-lapse imaging of the bacteria.

Taking advantage of microfluidic confinement, single cell AST can be performed phenotypically in the presence of antibiotics in the channel. Resistant strains can grow in the presence of the antibiotic while the antibiotic would inhibit the growth of susceptible strains (FIG. 1C). As the cross-section of the channels is compatible with the size of the pathogen, the bacterial growth is confined along the microchannel. The change in length of the bacteria in the channel over time is used to quantitatively measure the growth of the bacteria. This approach dramatically reduces the AST time to a time scale comparable to the doubling time of the bacteria.

Single Cell Pathogen Classification and AST

Figure 11:
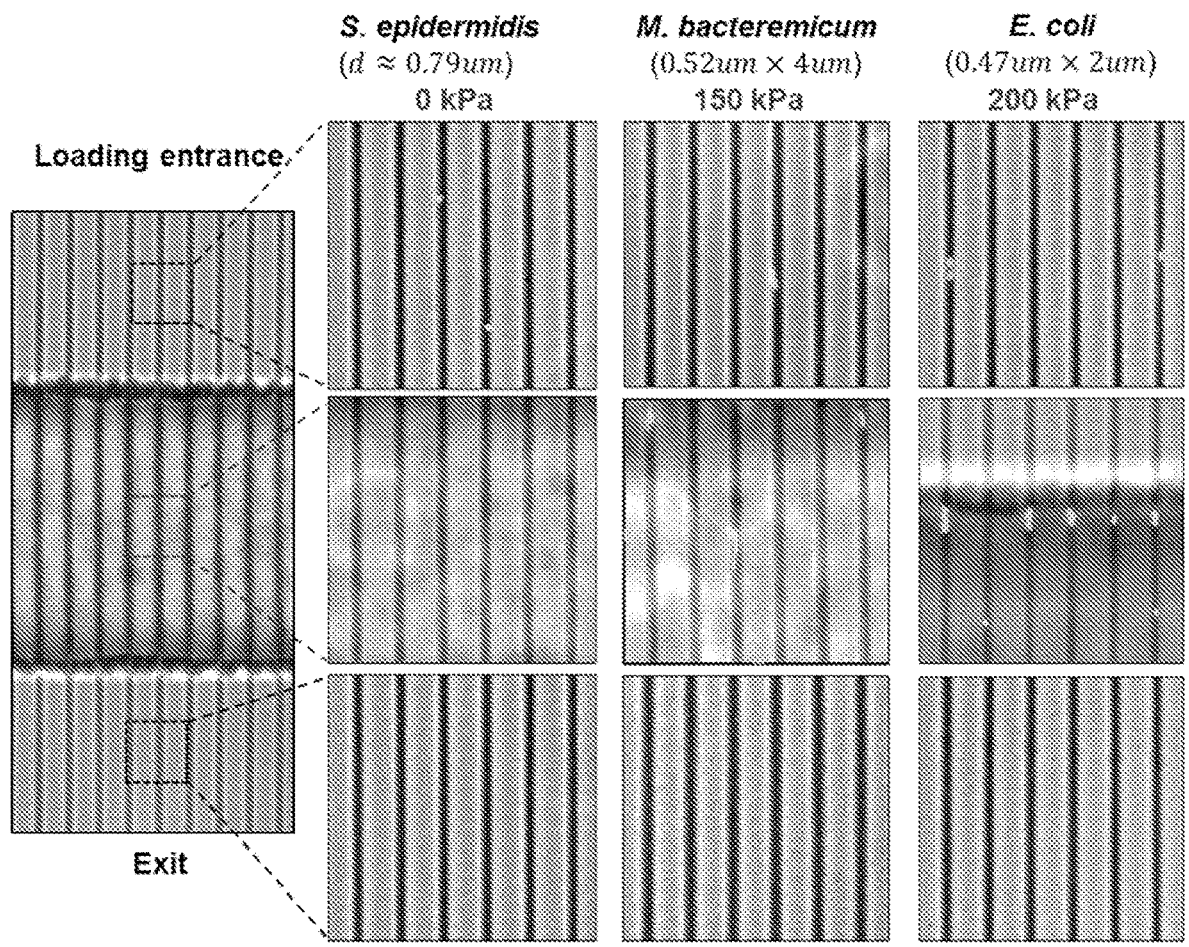
FIG. 11. Different bacterial species are trapped in the microchannels with different applied pressure. *S. epidermidis* was trapped at the entrance of the microchannels with 0 kPa applied pressure. *M. bacteremicum* was trapped in the microchannels with 150 kPa applied pressure. *E. coli* was trapped in the microchannels with 200 kPa applied pressure.

Pathogen classification by the adaptable microfluidic system was initially demonstrated using cultured *Escherichia coli* (*E. coli*), *Staphylococcus epidermidis* (*S. epidermidis*), and *Mycobacterium bacteremicum* (*M. bacteremicum*) (FIG. 1D and FIG. 11). These species could be physically separated with different pressure values (i.e., different regions of the microchannel). The distribution of the bacteria provided an indication on the size of the species. A calibration experiment was performed to estimate the pressure values. In the test, the majority of *S. epidermidis* (66%), *M. bacteremicum* (83%), and *E. coli* (83%) were trapped in the regions with 0 kPa, 150 kPa, and 200 kPa pneumatic pressure respectively. The overlap, such as between *M. bacteremicum* and *E. coli*, was due to the natural variation of the pathogen (FIG. 1E).

Figure 2:
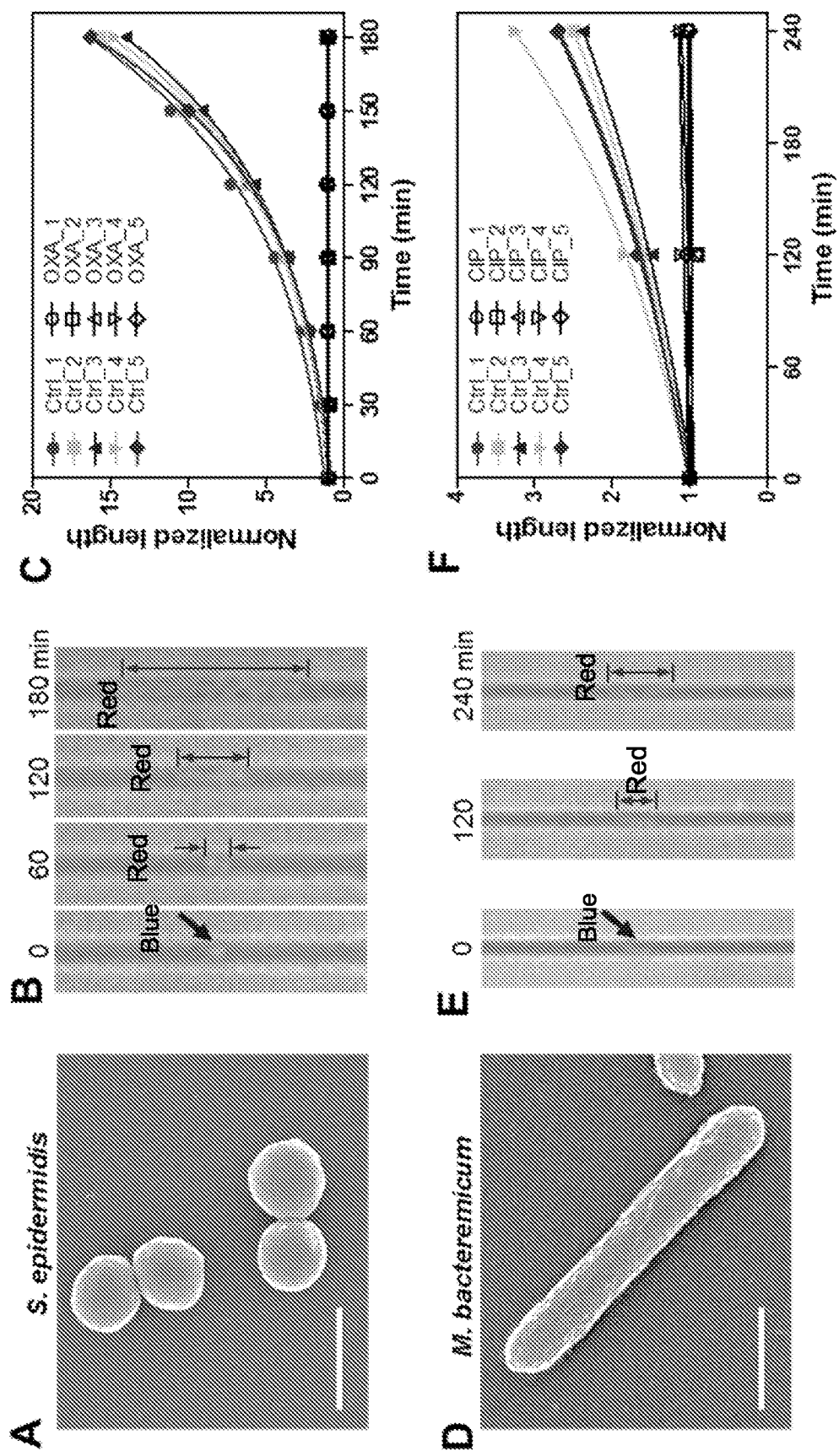
FIG. 2. Single cell AST of different bacterial species. (A, D, G) Scanning electron microscopy characterization of S. epidermidis (diameter=0.79±0.06 μm, n=10), M. bacteremicum (width=0.52±0.02 μm, n=10) and E. coli (width=0.47±0.04 μm, n=10). Scale bars, 1 μm. (B, E, H) Monitoring growth of single bacteria in the device. Blue arrows indicate the initial positions of the bacteria. Red arrows indicate the length of the bacteria. Scale bar, 5 μm. (C, F, I) Representative growth curves for control (color) and antibiotic (black) groups. Each curve represents growth of a single bacterium. Antimicrobial susceptibility is determined by monitoring phenotypic growth of the bacteria with and without antibiotics. All three bacteria are susceptible to the corresponding antibiotics. Images are representative of five independent tests.
Figure 2:
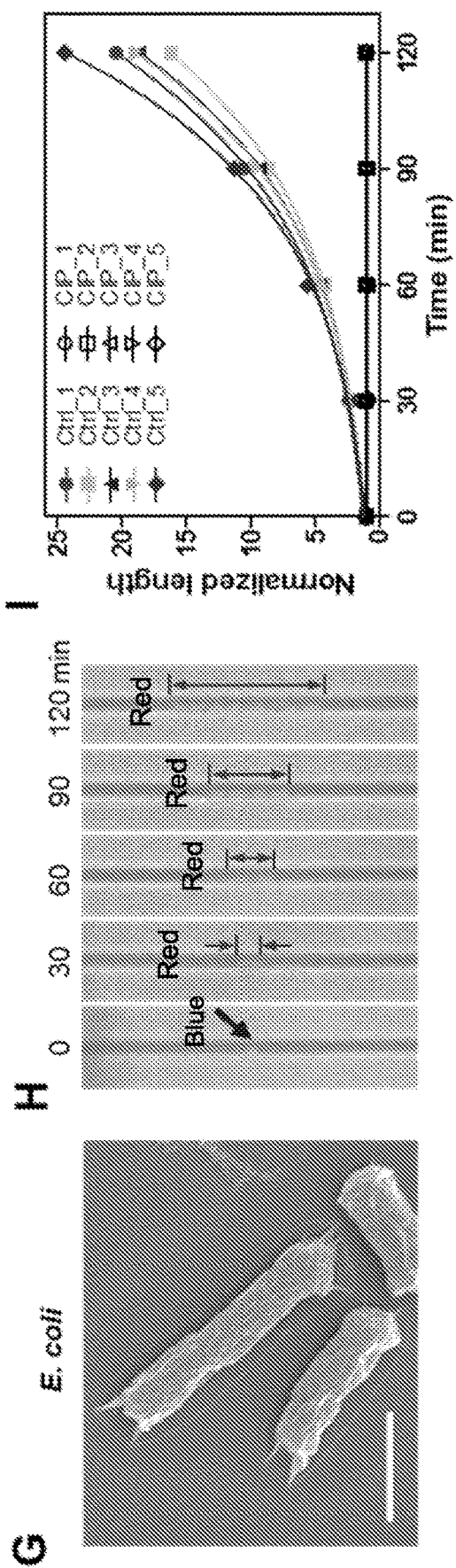

To analyze the trapping process, the physical dimensions of the bacteria were evaluated using scanning electron microscopy (SEM) (FIG. 2A, D, G). Since the bacteria were trapped along the channel, we measured the characteristic lengths by the width of rod shaped cells (bacilli) and diameter for spherical cells (cocci). The characteristic lengths of *S. epidermidis*, *M. bacteremicum*, and *E. coli* were 0.79±0.06, 0.52±0.02 and 0.47±0.04 μm, respectively. The size difference between *M. bacteremicum* and *E. coli* was only 50 nm. Nevertheless, the different in size of the bacteria was successfully captured based on the spatial distribution with multiple pressure regions. Based on our calibration, the heights of the microchannel were 1.32, 0.64, and 0.42 μm at the corresponding pressures suggesting an inverse correlation between the applied pressure and the size of bacteria trapped. In addition to the characteristic length, other properties of the bacteria were observed to influence the trapping pressure as well. For instance, *S. epidermidis* displayed strong adhesion with the PDMS surface and was often trapped at the entrance region of the channel with 0 kPa pressure. *M. bacteremicum*, in contrast, exhibited a high motility (43) and required a slightly higher trapping pressure. The distribution of the bacteria in the microfluidic system at a given pressure therefore represents a signature resulting from multiple characteristics of the species.

In embodiments, bacterial trapping channels of this disclosure are also capable of single cell AST by monitoring the phenotypic growth of the trapped bacteria in the channel. In control groups without antibiotics, the bacteria grew exponentially along the microchannels (FIG. 2B, E, H). In contrast, the bacterial growth was inhibited in the presence of antibiotics at the standard breakpoint concentration suggested by the Clinical and Laboratory Standards Institute (CLSI) guidelines to determine the antimicrobial susceptibility (44). Growth was measured by an increase in the length of the bacteria occupying the microchannel. The length was normalized according to the initial length for estimating the growth rate, to account for variation of the initial length. Comparison of the growth rate between the control group and the antibiotic group determined the susceptibility of the bacteria. Growth/Non-growth was defined quantitatively by a 50% reduction in the growth rate, which resulted in robust results in our calibration experiments (FIG. 2C, F, I). Unless otherwise specified, this definition is applied throughout Part I of this disclosure. For instance, ciprofloxacin (CIP) was effective for *E. coli* (EC137) and *M. bacteremicum*, while oxacillin (OXA) completely inhibited the growth of *S. epidermidis*. These results are consistent with broth dilution data, supporting pathogen classification and AST at the single cell level with the adaptable microfluidic system.

Identifying Polymicrobial Samples

Figure 12:
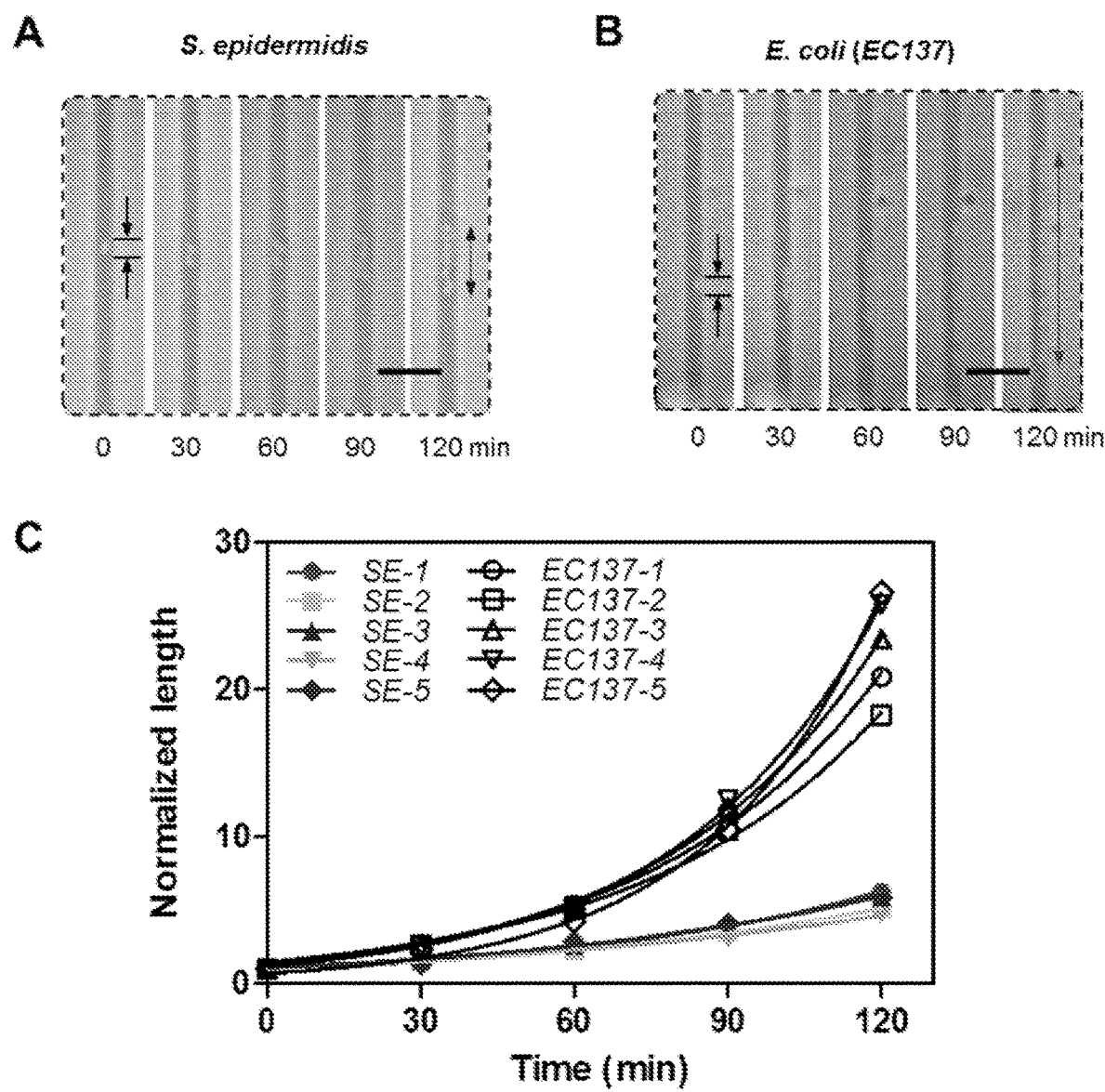
FIG. 12. Growth kinetics of polymicrobial samples with the tunable microfluidic device. (A) *S. epidermidis* was trapped in the entrance region and grew without antibiotics. (B) *E. coli* (EC137) was trapped in the region with 180 kPa applied pressure and grew without antibiotics. Scale bars, 10 μm. (C) Representative growth kinetics of the two species in the adaptable microfluidic system.

The adaptable microfluidic system of this disclosure, along with single cell analysis, opens the possibility of identifying polymicrobial infections, which exhibit enhanced disease severity and morbidity. In a non-limiting demonstration, the number of bacteria trapped is counted quantitatively. This capability is important for identifying polymicrobial samples. We illustrate this capability by testing a sample containing both *E. coli* and *S. epidermidis*. In agreement with our calibration, the majority (80%) of *E. coli* were physically trapped in the region with 180 kPa while the majority (85%) of *S. epidermidis* were trapped in the entrance region with 0 kPa pressure (FIG. 3A, D). The separation of these species can be verified with the shape. *E. coli* has a rod shape while *S. epidermidis* has a spherical shape (FIG. 3B-C). The two species were also discriminated by their antibiotic susceptibility profiles (FIG. 3E). In the ampicillin groups, the *S. epidermidis* strain, which was resistant to ampicillin, grew exponentially in the microchannels. In contrast, the *E. coli* strain, which was susceptible to ampicillin, was lysed under the same condition. Moreover, bacterial growth rates provided an additional indication of the polymicrobial nature of the sample. In the control experiment without antibiotics, both bacteria grew exponentially in different regions of the microchannels (FIG. 12). Examination of the data revealed that the growth rates were different between the two species. These results support the use of single cell analysis for identifying samples with multiple species.

We further evaluated the capability of the microfluidic system for identifying samples with multiple strains of the same species, which is challenging for genotypic diagnosis. Two strains of *E. coli* (EC137 and EC136 at a 10:1 ratio) with different antibiotic resistance profiles were tested. EC137 is susceptible to ampicillin while EC136 is resistant to ampicillin. Both strains were trapped in the microchannels at 180 kPa pressure with no spatial separation in the microchannel (FIG. 3F). The bacteria strains displayed similar growth rates and were indistinguishable in the control group. Nevertheless, examining the antibiotic responses revealed distinct behaviors between the bacteria (FIG. 3G-I). In the antibiotic group, EC136 grew exponentially with ampicillin in the medium, whereas EC137 was lysed by ampicillin. FIG. 3J illustrates the growth curves of EC136 and EC137 in the same test. Since EC137 had a higher initial concentration (10-fold over EC136), this result demonstrated detecting a resistant strain that outgrows a dominating strain over time in the presence of antibiotics (FIG. 3I, J).

Direct AST with Clinical Samples

Figure 4:
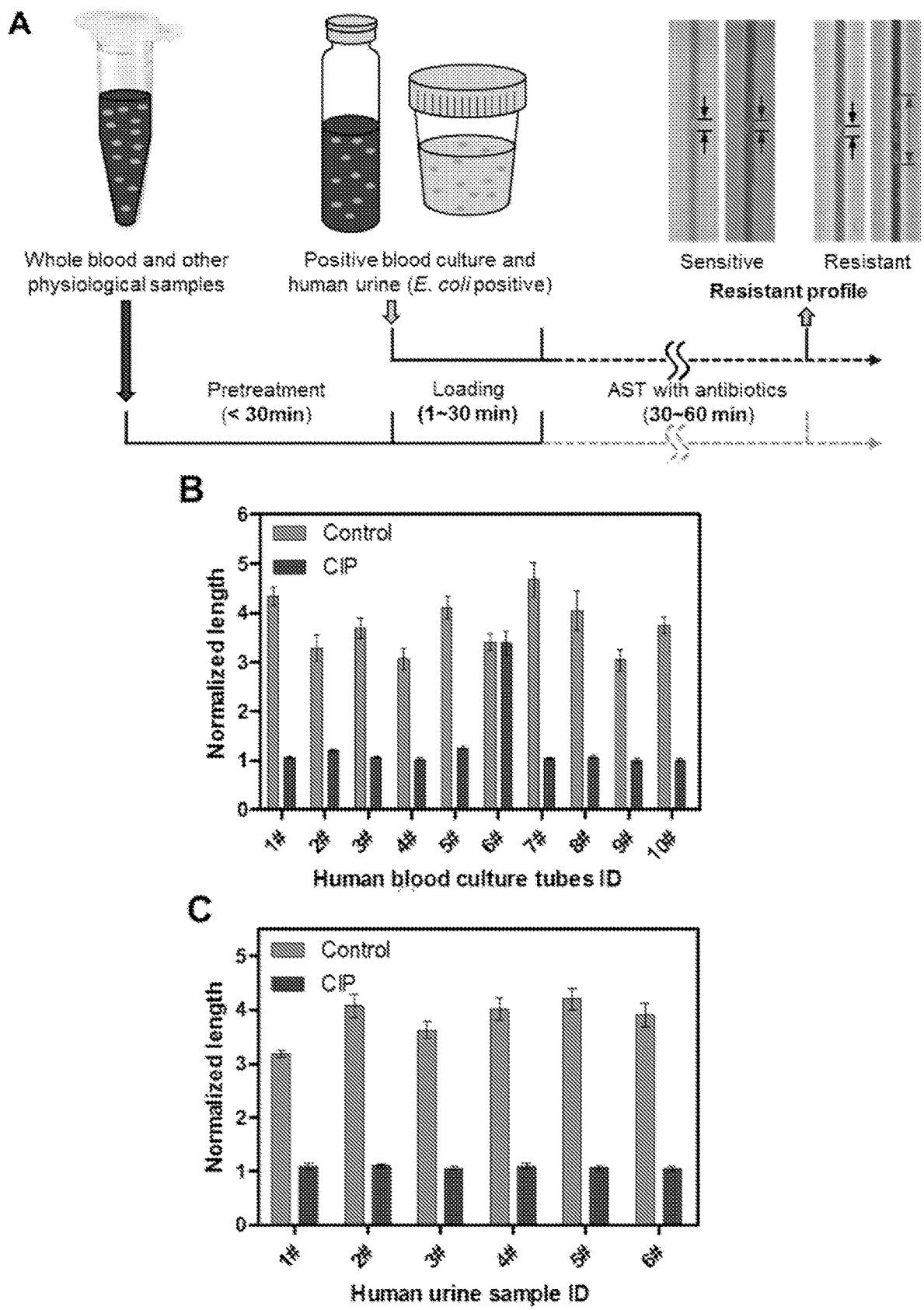
FIG. 4. Single cell AST of clinical samples with the adaptable microfluidic device. (A) Single cell AST procedure for clinical samples. Blood cultures and urine can be mixed with culture medium at a 1:10 ratio with and without antibiotic and loaded directly into the adaptable microfluidic device for single cell AST. The loading time lies between 1 to 30 min depending on the bacteria concentration. For whole blood and other physiological samples with complex matrices, sample pretreatment is performed prior to microchannel loading (as described in materials and methods). (B) Direct AST of 10 positive human blood cultures. Only sample #6 is resistant to ciprofloxacin as confirmed by the clinical microbiology results. (C) Direct AST of human urine samples at 60 min. All six samples are susceptible to ciprofloxacin as confirmed by broth dilution.
Figure 13:
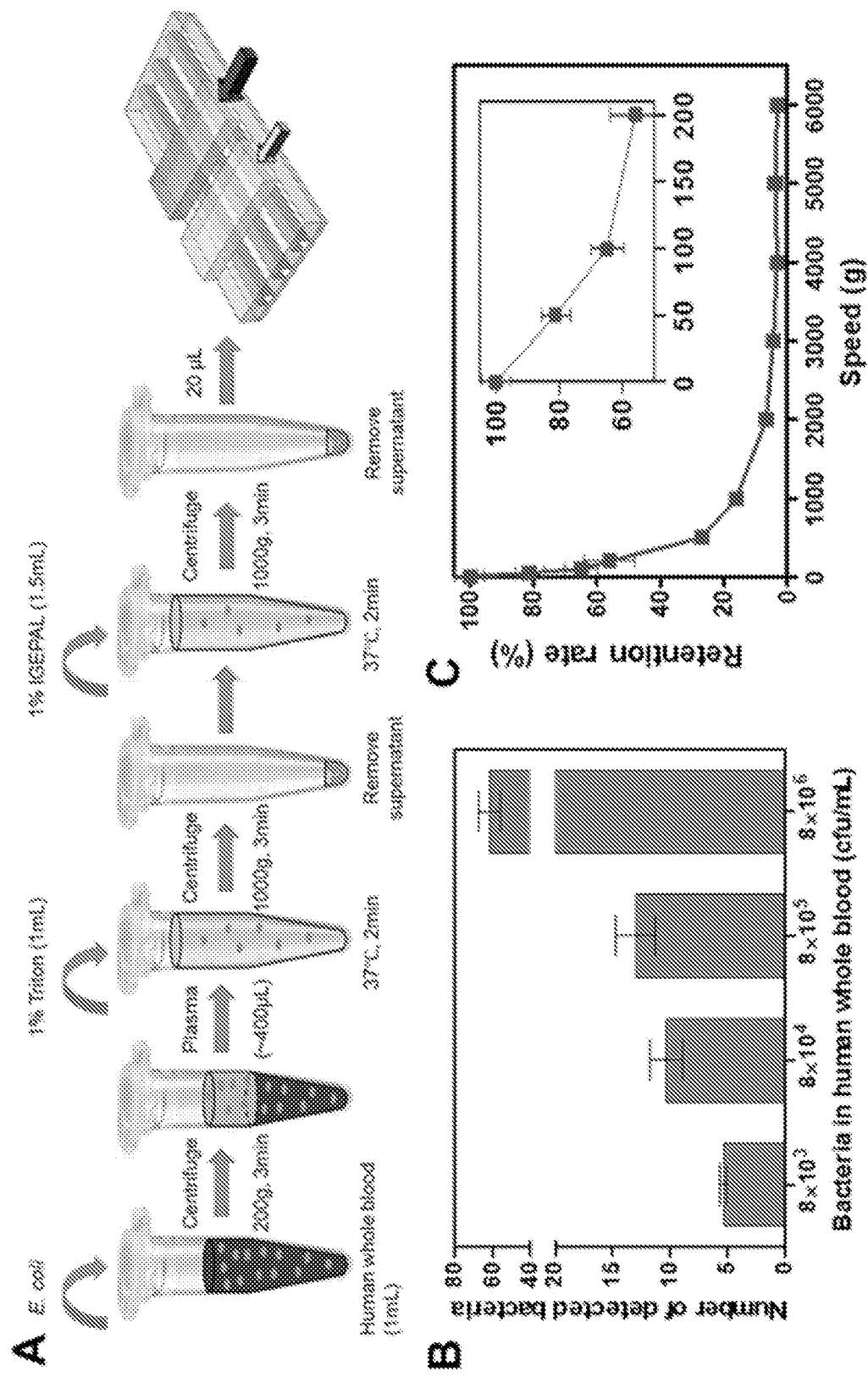
FIG. 13. Pre-treatment procedure of whole blood samples for single cell pathogen classification and AST. (A) Whole blood was first centrifuged to remove the majority of blood cells. The plasma was then mixed with 1% triton to remove remaining blood cells and small particles. The sample was centrifuged again and the supernatant was removed. The impurities were further dissolved in 1% IGEPAL. The sample was centrifuged again and the supernatant was removed. Then, the sample was loaded to the microfluidic device for single cell pathogen classification and AST. (B) Trapping of bacterial pathogens in the adaptable microfluidic system with whole blood samples spiked with *E. coli* (n=3). (C) Optimization of the centrifuge speed for bacteria retention in whole blood. Insert indicates the bacteria retention rate at low speed. (D) Images of bacterial samples after centrifugation. (E) Plasma separation in human whole blood samples by centrifugation. (F) Surfactants for reducing blood cell and debris in plasma samples. Plasma was separated from whole blood after centrifugation at 200 g for 3 minutes. The plasma was incubated with MH broth, triton, and IGEPAL. The samples were centrifuged at 1000 g for 3 min. (G) Microscopic inspection of control group, 1% Triton-100, and 5% Triton-100. Scale bars, 50 μm. Inserts represent magnified views. Scale bars, 10 μm.
Figure 13:
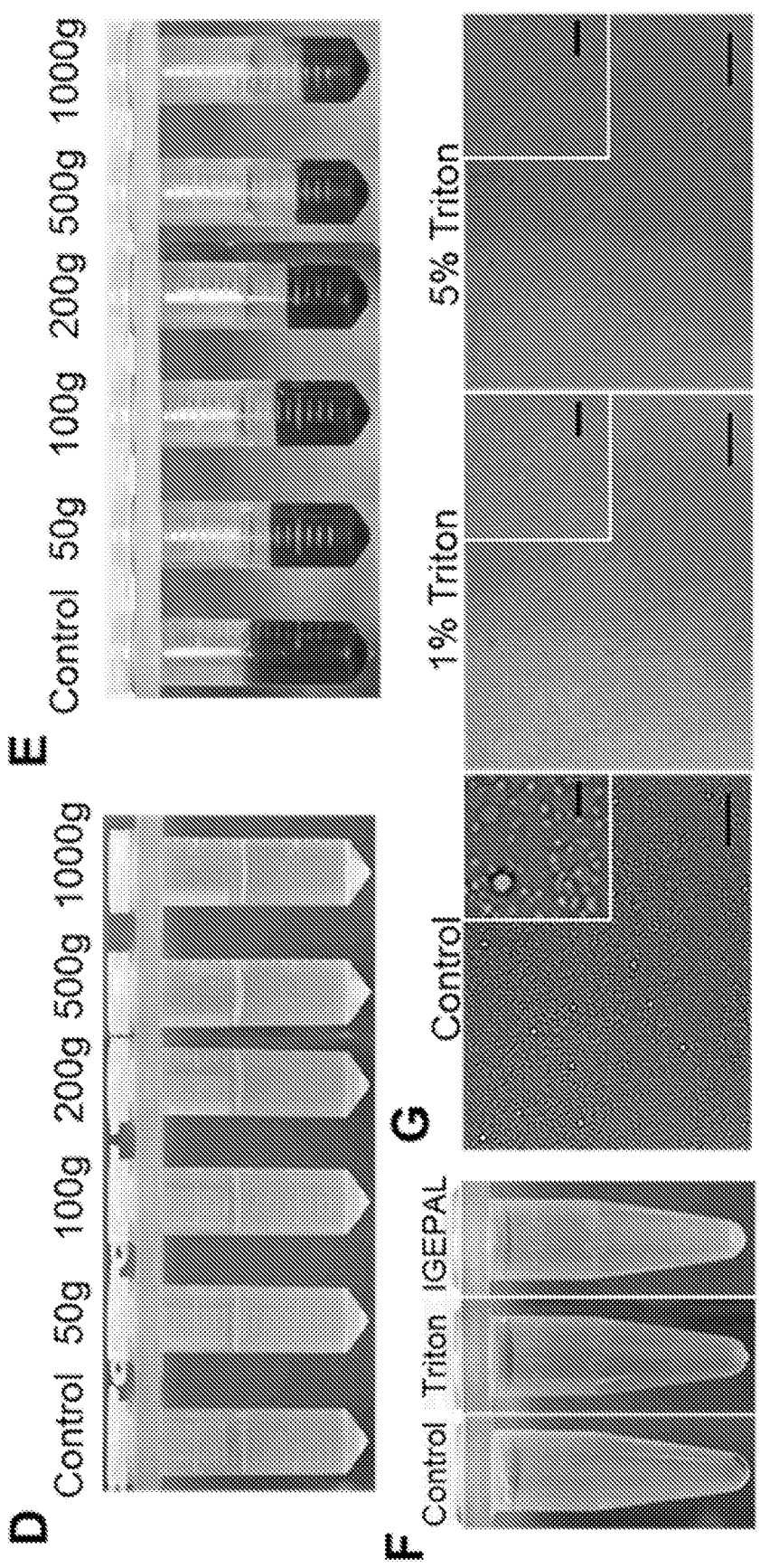
Figure 14:
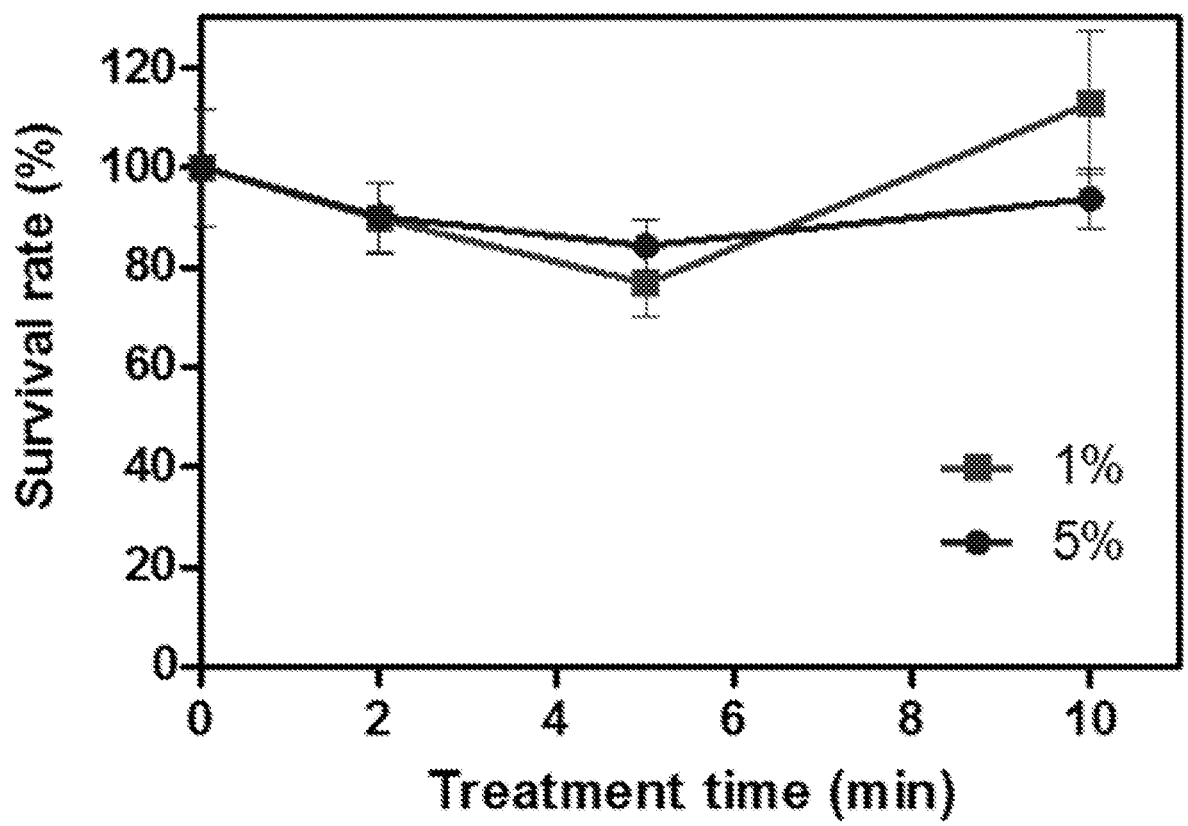
FIG. 14. Effect of triton on bacterial survival rate. The tests were performed with 1% and 5% triton.
Figure 15:
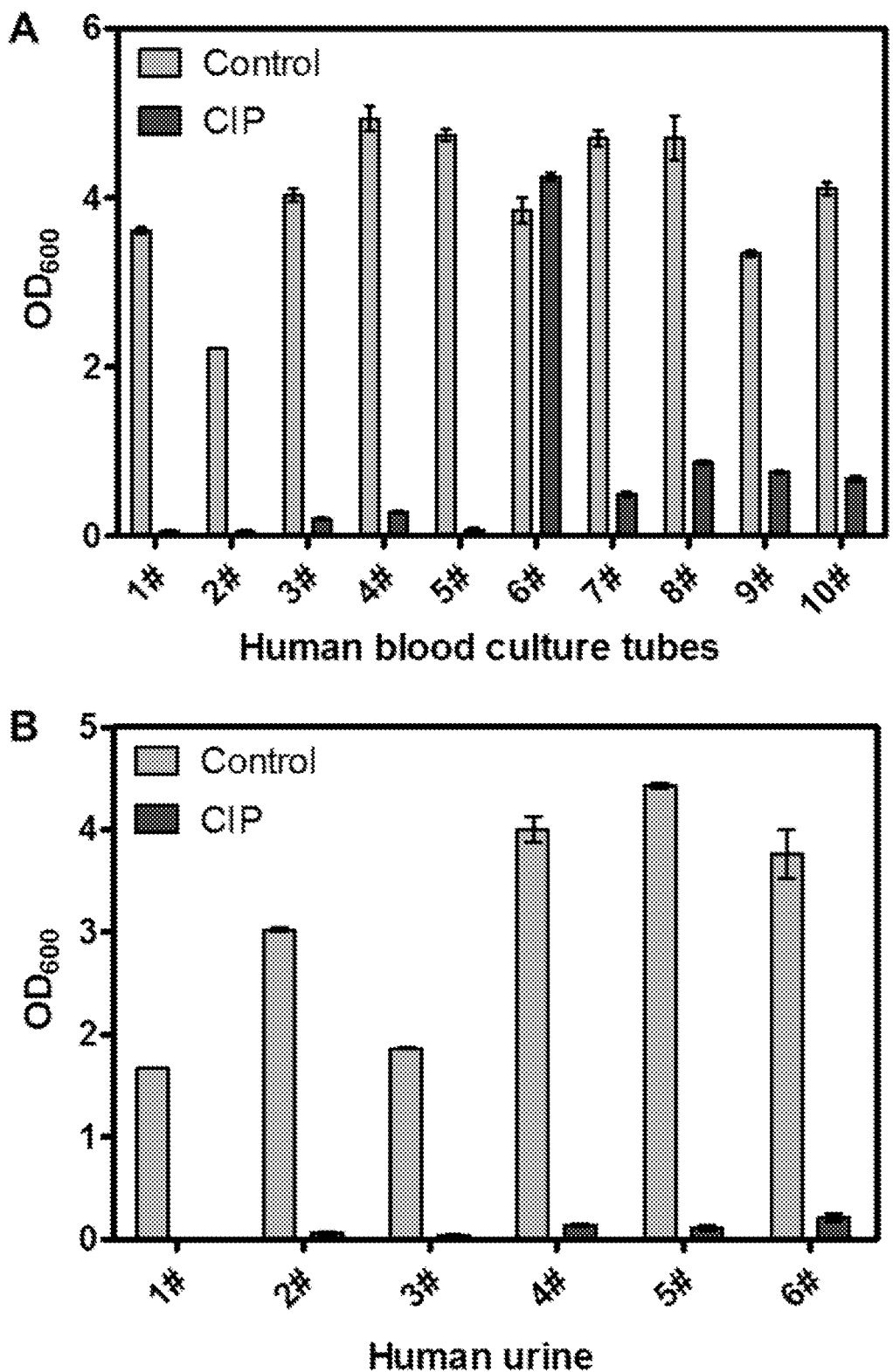
FIG. 15. AST of clinical samples by overnight culture. (A) AST of clinical blood tube samples by overnight culture. Sample #6 is resistant to ciprofloxacin. (B) AST of clinical human urine samples by overnight culture. All six samples are susceptible to ciprofloxacin. All clinical samples are positive for *E. coli*.

We evaluated the ability of a device of this disclosure for testing clinical samples, including blood culture (bottle), urine, and whole blood. Single cell AST was implemented for ten blood cultures and six urine samples that were cultured positive for the presence of *E. coli*. Blood cultures and urine samples were mixed with Muller Hinton (MH) broth at a 1:10 ratio and directly loaded in the microfluidic system. Additionally, clinical isolates of *E. coli* were spiked into human whole blood and a pretreatment step was performed to isolate bacteria in the sample before the loading process (FIG. 13-14). AST results were determined within 60 minutes by directly observing the growth of the bacteria in the microfluidic system (FIG. 4A). The detailed growth for bacteria in blood cultures was monitored and analyzed at the single cell level. Among the 10 blood cultures, one (#6) was resistant to ciprofloxacin and the others were susceptible (FIG. 4B). The growth rate of the resistant bacteria under antibiotic treatment was indistinguishable from the control (i.e., no antibiotic). Similarly, the bacteria in all six urine samples were ciprofloxacin sensitive (FIG. 4C). The results were verified by broth dilution with overnight culture (FIG. 15).

Figure 16:
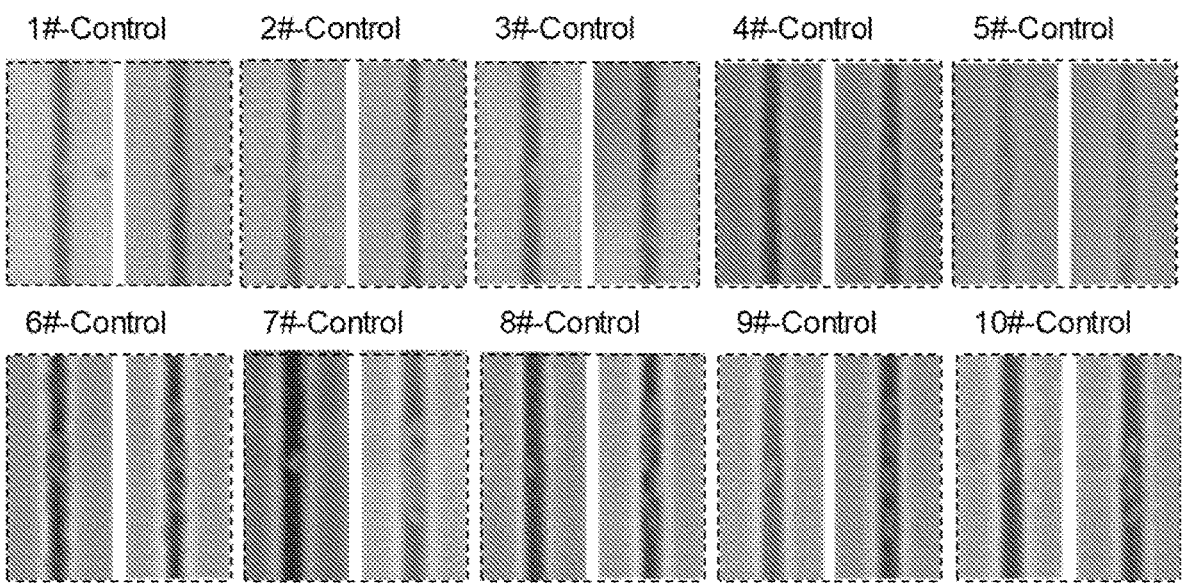
FIG. 16. Pathogen classification and AST for *E. coli*-positive blood cultures and urine samples. Bacteria in blood cultures (A) and urine samples (B) were trapped and grew in channels at the single cell level. Each group represents the time-lapse images at 0 min and 60 min after the loading process. The scale bar is 10 μm for all images. (C) The minimum trapping pressure to trap *E. coli* in different matrix, including MH broth, blood cultures, and urine. The p value is 0.5701 among these three groups using ANOVA test.
Figure 16:
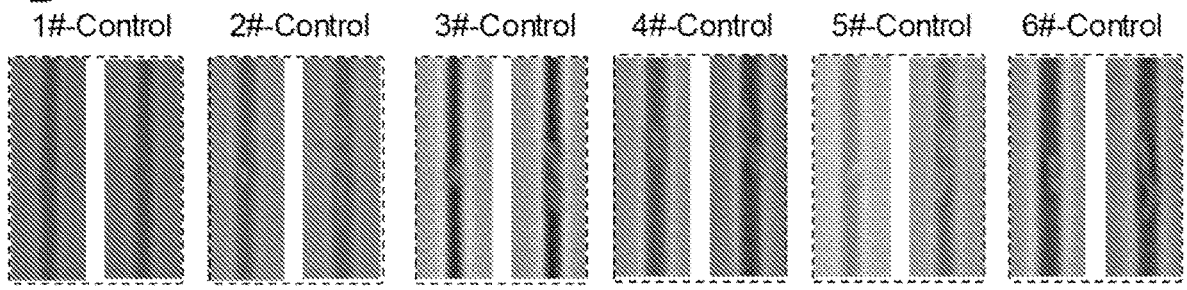
Figure 16:
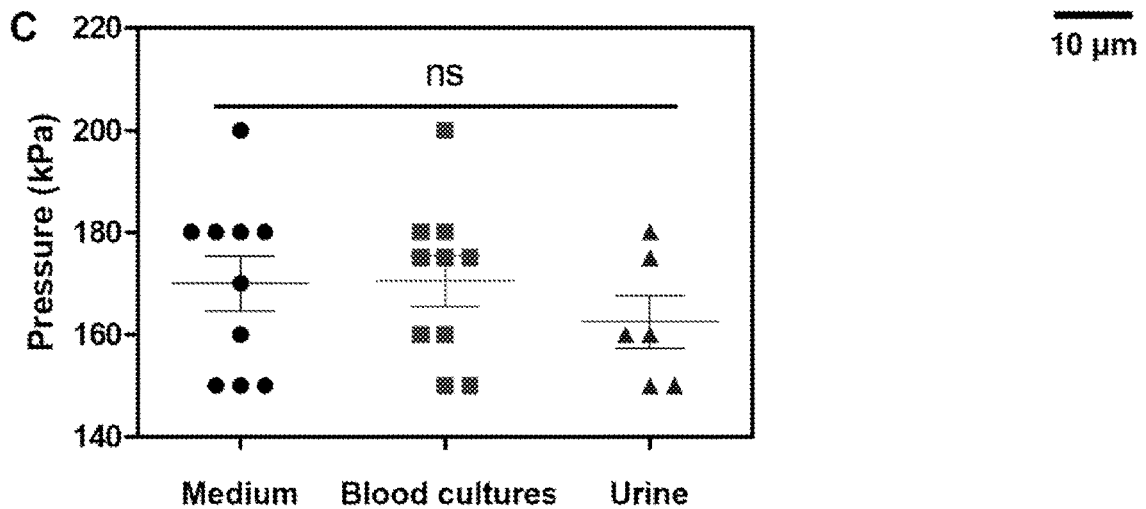

The *E. coli*-positive samples allow us to evaluate the influence of the sample variability on the robustness of the system. We studied the effect of the bacterial characteristic length on the trapping process. In our SEM characterization, the width of the *E. coli* strains has a standard deviation of approximately 40 nm. The pneumatic pressure to trap these *E. coli* strains was 170±17 kPa (mean±SD, n=10 independent experiments) (FIG. 16A-B). This result indicates that the trapping pressure is consistent for the same strain. We also examined the effect of the source of *E. coli* (i.e., blood or urine) and culture conditions (medium, blood and urine). Comparison of the results from blood, urine and MH broth suggests the culture condition does not have a significant effect on the trapping pressure for the bacteria (FIG. 16C). These results collectively support direct AST of clinical samples with the adaptable microfluidic system.

Pathogen Classification and AST of Clinical Samples

We designed an approach using clinical urine samples, including negative samples. To classify samples with blinded pathogens (i.e., unknown size), we developed a dynamic protocol to identify the presence and size of bacteria in the samples (FIG. 5A). In this protocol, clinical samples were mixed with MH broth and loaded into the microfluidic system. A large pressure (200 kPa) was first applied to trap any bacteria in the samples. For negative samples, the test was repeated three times to verify the result. If a pathogen was identified, the pressure was released and then gradually increased to determine the minimum trapping pressure for pathogen classification. The protocol was repeated to identify bacteria with smaller characteristic lengths in the polymicrobial samples, which could pass through the trapping window with a smaller pneumatic pressure (e.g., the strain in FIG. 5A that has gone past the Ptrap region). In Part I of this disclosure, at least five bacteria were trapped and classified based on the size (minimum trapping pressure) and shape (*bacillus* and *coccus*).

Figure 6:
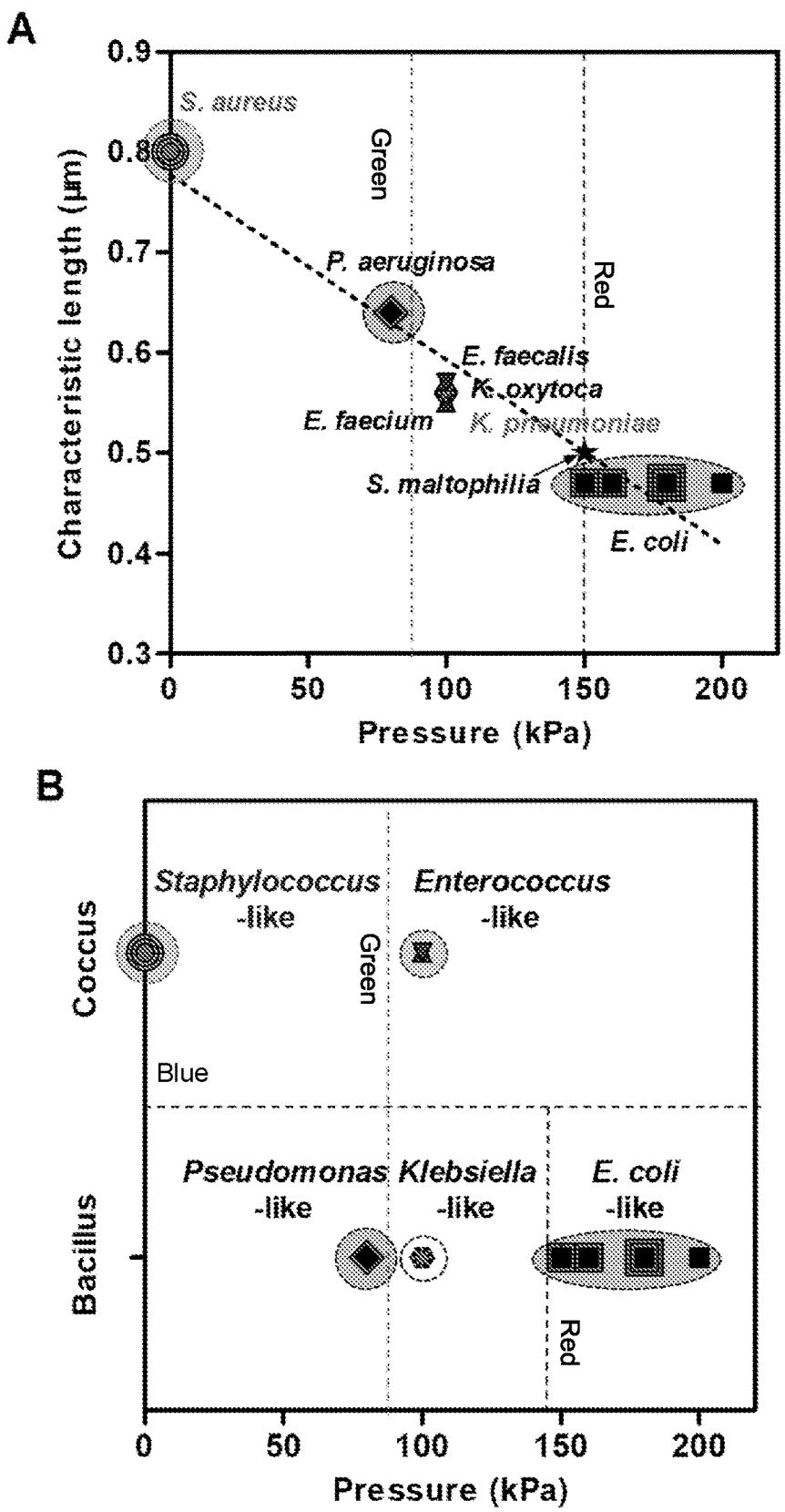
FIG. 6. Single cell AST of clinical urine samples. (A) Pathogen identification and AST were performed for 25 clinical urine samples with blinded pathogens. The minimum trapping pressure was compared with the bacterial size of all positive samples retrospectively. (B) The bacteria were classified based on the shape (blue dotted lines) and the minimum trapping pressure (green and red dotted lines). (C) The susceptibility was determined for all positive samples at 120 min. Sample #7, #8, #10, #20, and #24 were culture negative. Samples #6, #9, #12, #15, #18, #22, and #25 were ciprofloxacin resistant, as confirmed by broth dilution. (D-F) Representative growth curves for control groups (color) and antibiotic groups (black) in ciprofloxacin susceptible sample (D, sample #4), ciprofloxacin resistant sample (E, sample #15), and polymicrobial infection sample (F, sample #3). In this polymicrobial infection sample, both bacteria (S. aureus and S. maltophilia) were susceptible to ciprofloxacin. All curves were fitted with exponential growth equation in GraphPad Prism.
Figure 6:
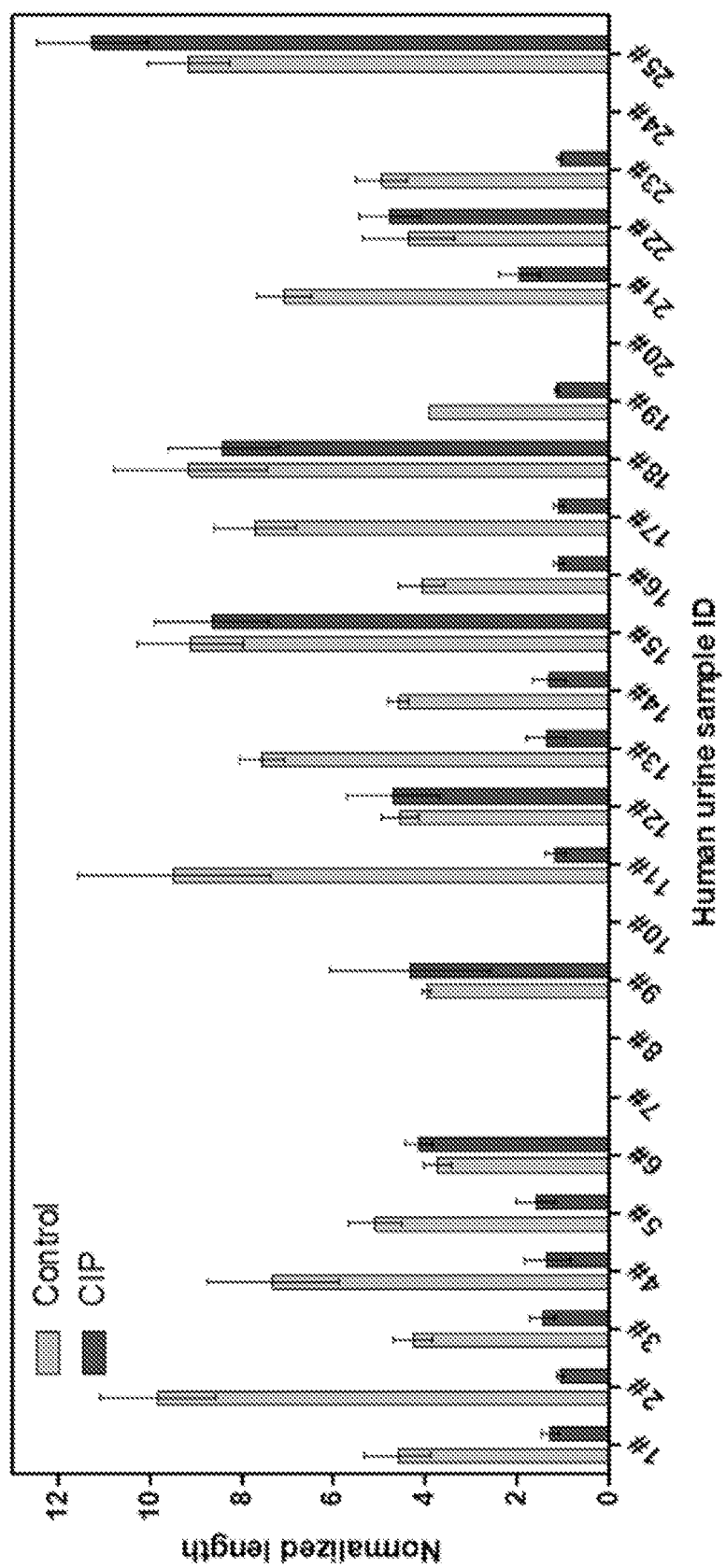
Figure 6:
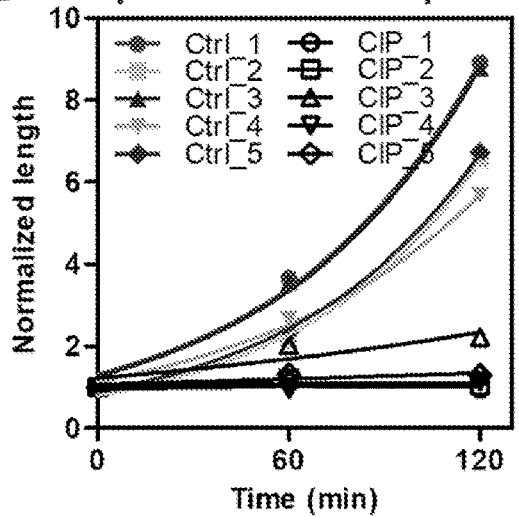
Figure 6:
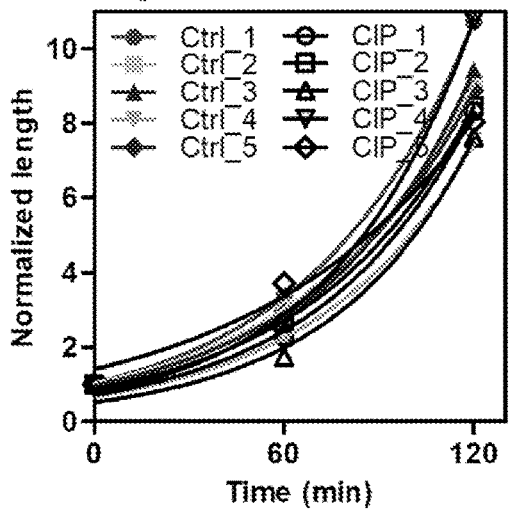
Figure 6:
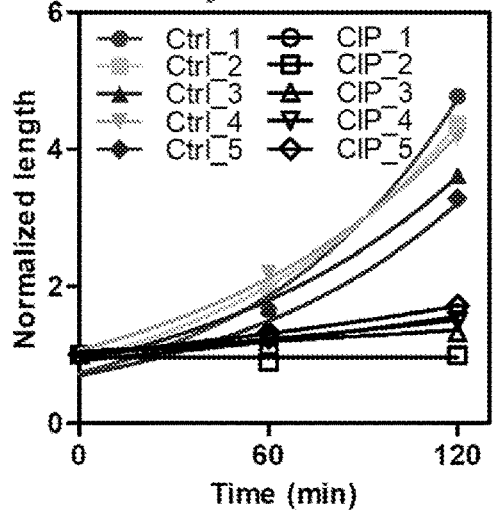
Figure 17:
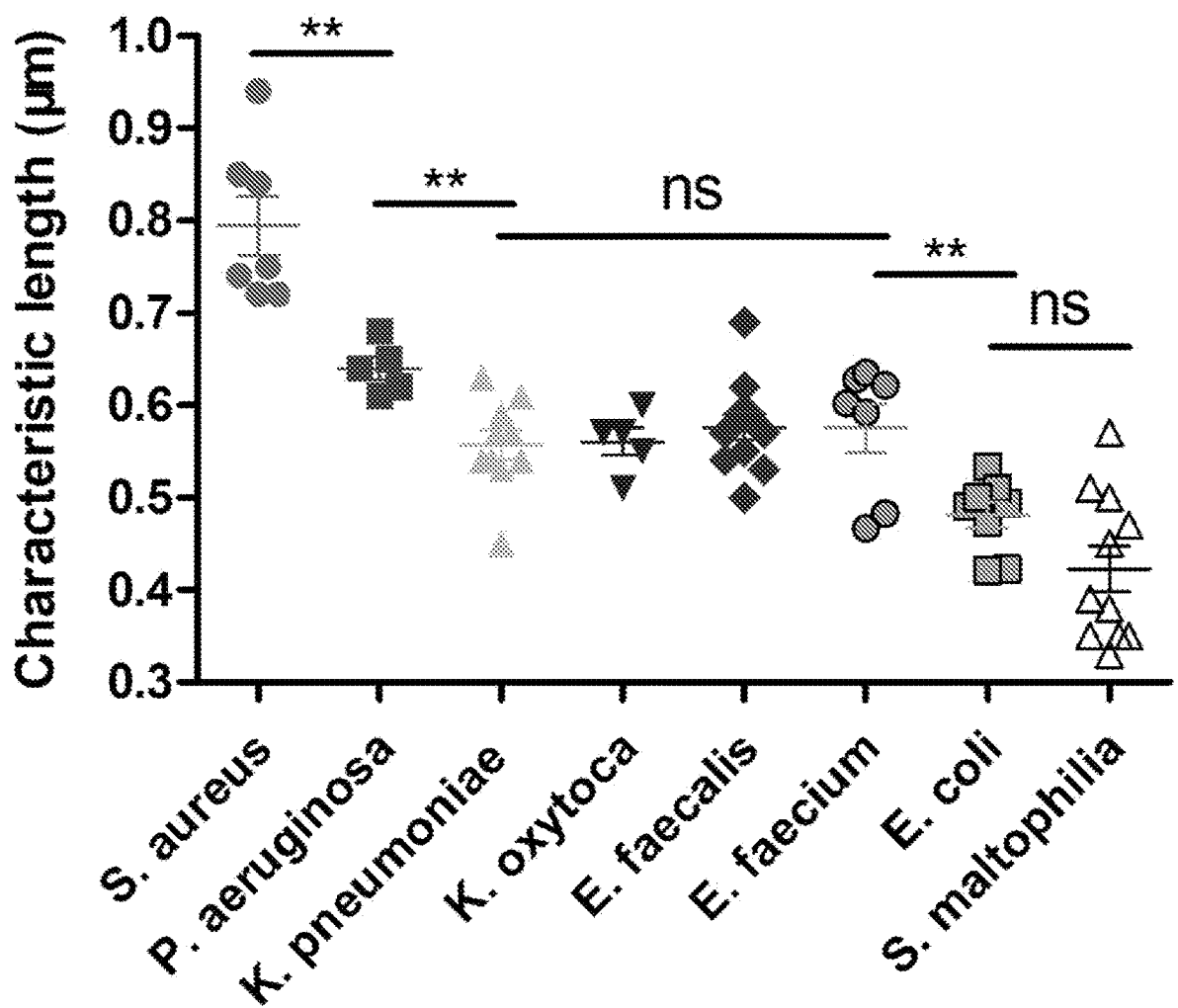
FIG. 17. Characteristic length of typical bacterial species in urine tract infections. The characteristic length of *E. coli* was measured by scanning electron microscopy. The characteristic lengths of *S. aureus* (45, 46), *P. aeruginosa* (47), *K. pneumonia* (47, 48), *K. oxytoca* (48), *E. faecalis* (49, 50), *E. faecium* (51, 52), and *S. maltophilia* (53, 54) were estimated based on scanning electron microscopy and transmission electron microscopy images from the literatures.
Figure 18:
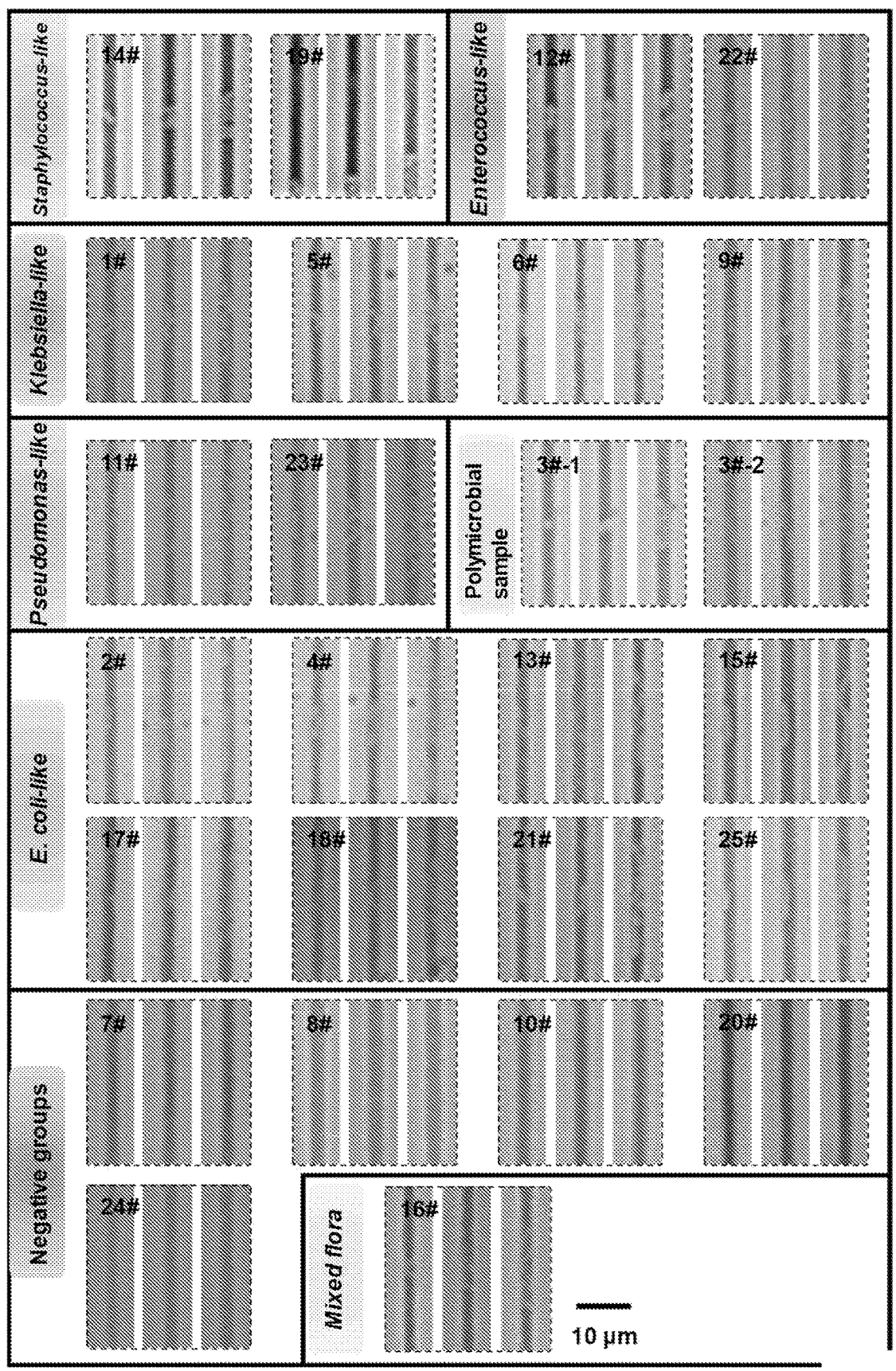
FIG. 18. Pathogen classification and AST for urine with blinded bacteria. The urine samples were classified into *Staphylococcus*-like, *Enterococcus*-like, *Pseudomonas*-like, *Klebsiella*-like, *E. coli*-like, polymicrobial samples, mixed flora, and negative samples. The classification depends upon the morphology (i.e., rod-shape or spherical) and trapping pressure (e.g., *E. coli* were trapped with a pressure ranging from 150 to 200 kPa while *Pseudomonas* spp. were trapped at 80 kPa). Each set of time-lapse images represents the growth of a single bacterium in the control group without antibiotics. The time scale is 120 min with an interval of 60 min. Scale bar, 10 μm.
Figure 19:
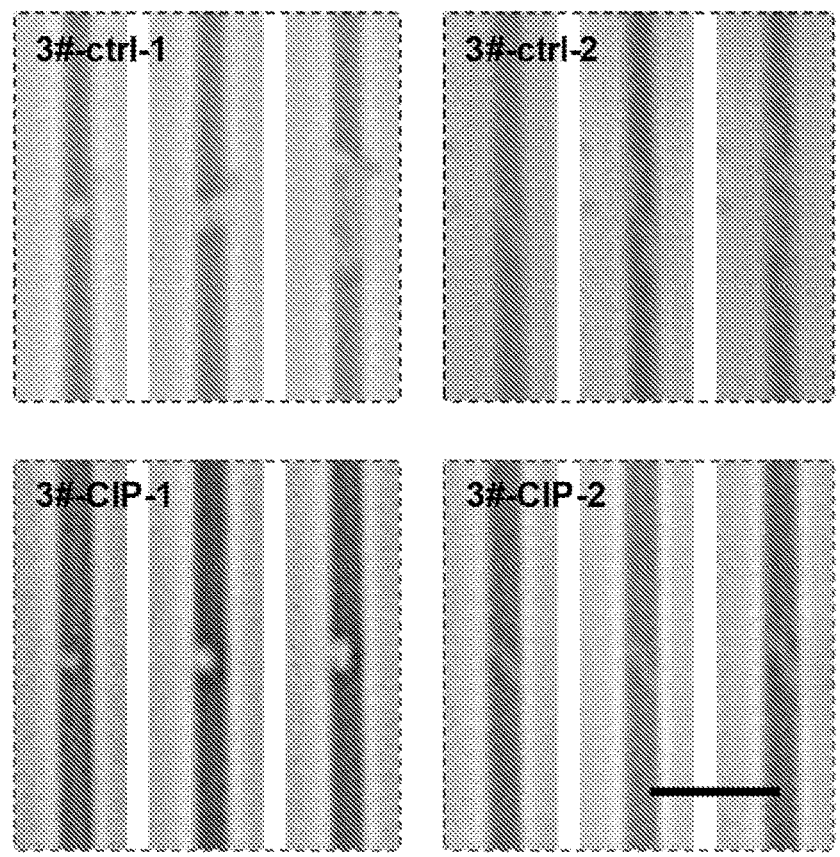
FIG. 19. Diagnosis of polymicrobial sample (#3) by the adaptable microchannel system. (A) Two bacteria species were identified based on the morphology (one is spherical and the other is rod-shape). The resistant profiles for both species were determined by the time-lapse images representing the single bacterial growth in the control and antibiotic groups. The time scale is 120 min with an interval of 60 min. Scale bar, 10 The species were identified to be *S. aureus* and *S. maltophilia* by clinical microbiology. (B) Distribution of the bacteria in the entrance region (0 kPa) and trapping region (150 kPa). The bacteria were classified based on the shape of the bacteria. The bacteria were trapped in different regions of the microchannel device due to the difference in their characteristic lengths. (C) The percentage of each species in the clinical sample trapped by the adaptable microfluidic system.
Figure 19:
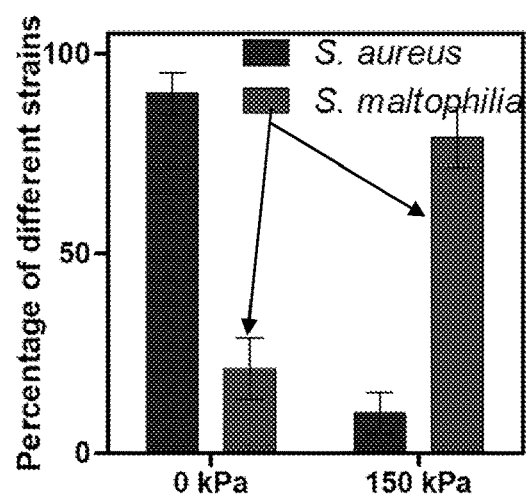
Figure 19:
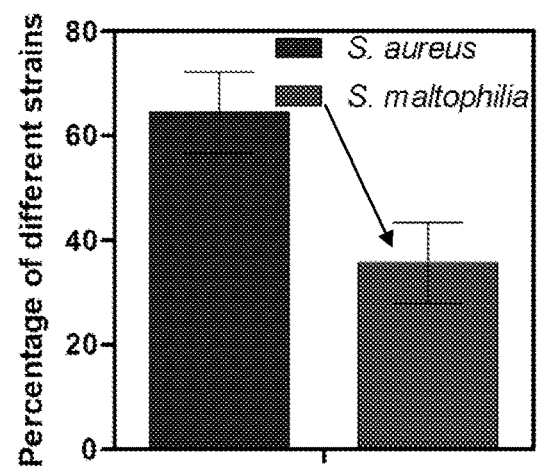

The bacteria were classified into *Staphylococcus*-like, *Enterococcus*-like, *Pseudomonas*-like, *Klebsiella*-like, and E. coli-like groups. The correlation between the trapping pressure and the characteristic length of common uropathogens was validated based on electron microscopy from our experiment and the literature (FIG. 17). For pathogen classification, the microfluidic device correctly identified 24 out of 25 samples (FIG. 18), including the polymicrobial sample. The bacteria were correctly classified based on their morphology and the trapping pressure (FIG. 6B). In particular, the pathogens in the polymicrobial sample (#3) displayed different shapes (bacillus vs coccus) and were trapped at different pressure values (FIG. 19). Sample #16 was reported as mixed flora. Samples #1 and #6 were misclassified as Klebsiella-like in the microfluidic systems. Nevertheless, CHROMagar results suggested that these samples contained only Klebsiella spp. Sample #10 reported as E. cloacae in the clinical microbiology lab appeared negative in the microfluidic system. Plating counting and MH broth culture also showed the sample was negative. These results suggest these errors may be associated with sample handling and transportation.

Figure 3:
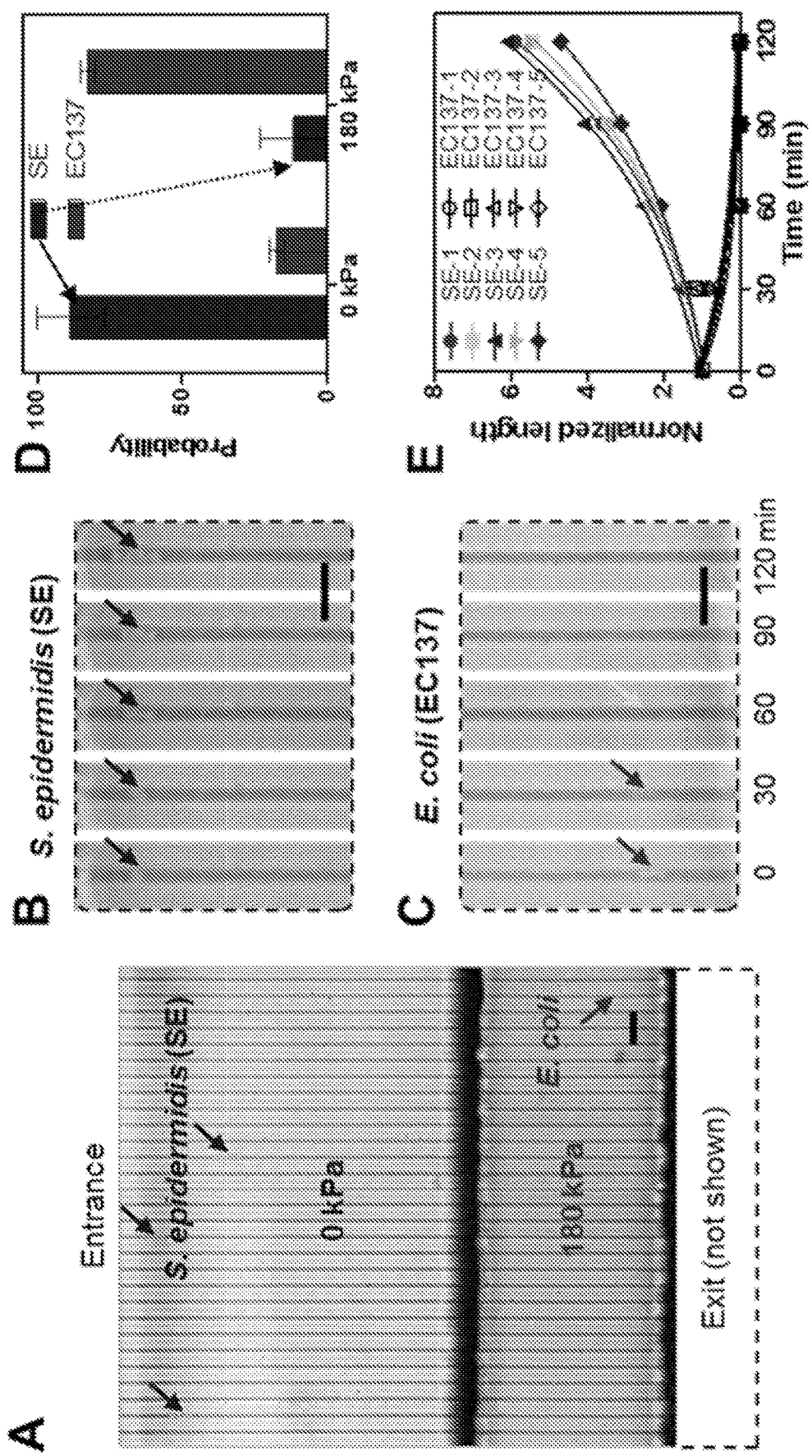
FIG. 3. Single cell AST of polymicrobial samples with the adaptable microfluidic device. (A) Identification of polymicrobial samples based on spatial distribution of pathogens. Two bacterial species (S. epidermidis at 5×10⁵ cfu/mL and E. coli at 5×10⁵ cfu/mL) were trapped in different regions of the channels. (B-C) Monitoring of bacterial growth in different regions of the channel. Ampicillin (8 µg/ml) displays no effect on S. epidermidis and bactericidal effect on the uropathogenic E. coli (EC137). (D-E) Distribution of the bacteria in the channel determined by the antibiotic response of the bacteria. Representative growth kinetics of the two species in the presence of ampicillin in the single cell AST device. Color symbols represent S. epidermidis and black symbols represent E. coli 137. (F) Identification of polymicrobial samples based on antimicrobial susceptibility. Two strains of E. coli (EC137, 5×10⁶ cfu/mL and EC136, 5×10⁵ cfu/mL) were trapped in the same region of the microchannel. (G-H) EC136 is resistant to ampicillin and grew in the channel. EC137 is susceptible to ampicillin. (I-J) Distribution of the bacteria in the channel determined by the antibiotic response of the bacteria. Representative growth kinetics of the two strains in the single cell AST device. Images are representative of three independent tests. Scale bars in A and F, 20 µm. Scale bars in B, C, G, H, 10 µm.
Figure 3:
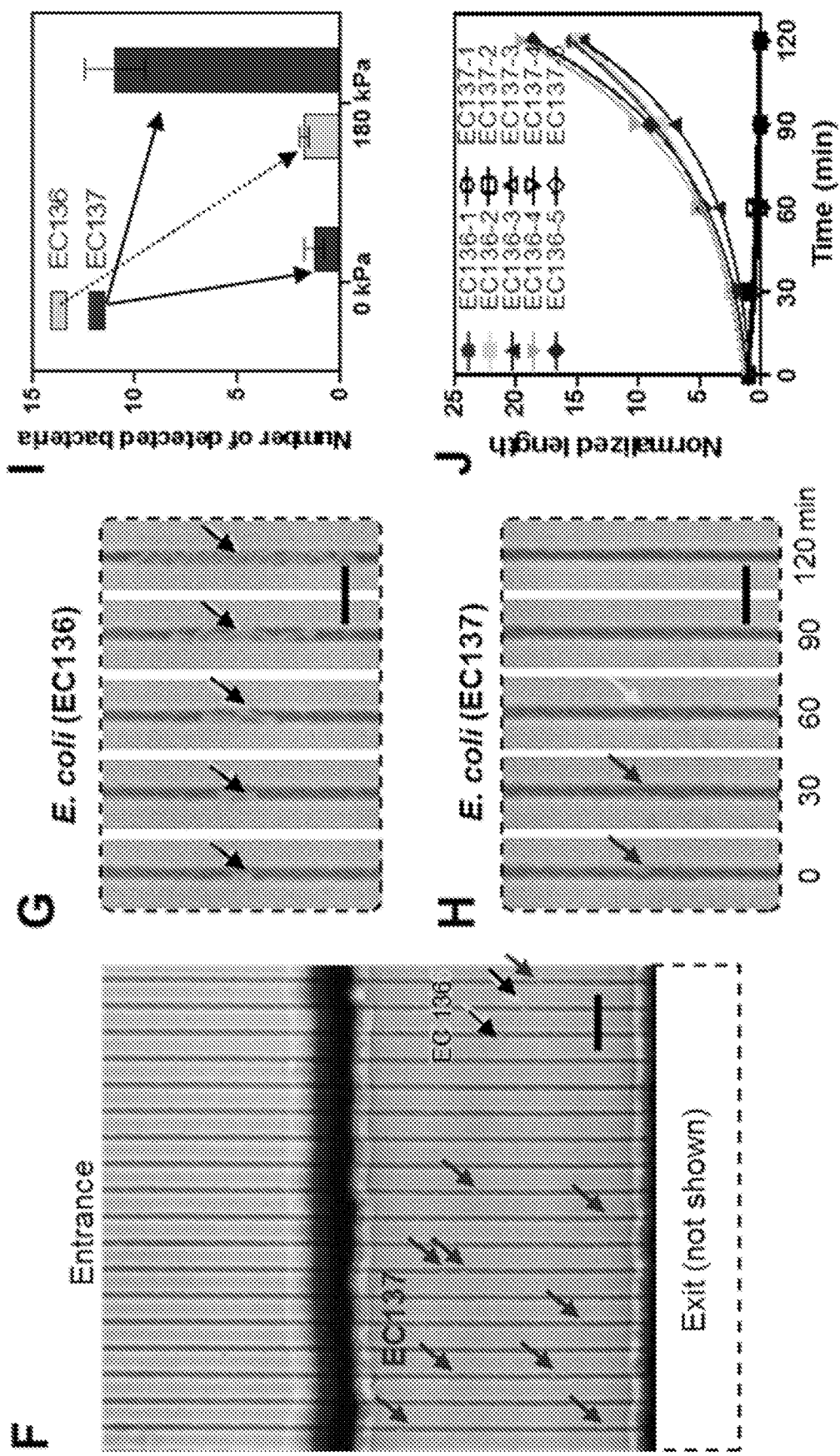

In this non-limiting example of a protocol, the sample was reported as polymicrobial if multiple bacterial populations were identified. The adaptable microfluidic system determines polymicrobial samples by size, shape, growth rate, and antimicrobial susceptibility (FIG. 3). If the bacteria have similar size, shape, growth rate, and antimicrobial susceptibility, the microfluidic system will not be able to separate them. Flora and contamination were not considered if the species had a low concentration. For positive samples, the pathogens were cultured with and without ciprofloxacin. To avoid false negative due to pathogens with a long doubling time, the bacteria were cultured for up to two hours and the growth rates were compared between samples with and without antibiotic. The pathogen was classified as susceptible when the growth rate was significantly inhibited (i.e., less than half of the control groups) or resistant when the growth rate was similar to the no antibiotic control (i.e., more than half of the control).

In this approach, 25 clinical urine samples were tested using the adaptable microfluidic system. The presence of bacteria and the minimum trapping pressure were recorded for each sample (Table 1). Using the adaptable microfluidic system, 19 samples were identified with a single species of bacteria and 1 sample (#3) was polymicrobial. Five samples (#7, #8, #10, #20, #24) were negative. The samples were independently tested and identified in the clinical microbiology laboratory at Penn State Milton S. Hershey Medical Center. Based on the clinical report, there were 4 negative samples (#7, #8, #20, #24), 19 monomicrobial samples, 1 polymicrobial sample (#3), and 1 sample with mixed flora (Table 1). The minimum trapping pressure was compared with the characteristic length of the bacteria (FIG. 6A). In agreement with our calibration, the results revealed an inverse relationship and demonstrated a separation resolution below 100 nm. For instance, Klebsiella strains (0.56 μm) could be separated from E. coli (0.47 μm) despite the small difference in size (<100 nm).

TABLE 1

Trapping of bacteria in the entrance region (region 1, 0 kPa) and trapping region (region 2, variable pressure) of the adaptable microfluidic system.

| Sample # | Region 1 | | | Region 2 | | |
| --- | --- | --- | --- | --- | --- | --- |
| | Pressure (kPa) | Bacteria # | Ratio | Pressure (kPa) | Bacteria # | Ratio |
| 1 | 0 | 7 | 19% | 100 | 29 | 81% |
| 2 | 0 | 14 | 19% | 180 | 60 | 81% |
| 3-spherical | 0 | 51 | 89% | 150 | 6 | 11% |
| 3-rod | 0 | 21 | 18% | 150 | 98 | 82% |
| 4 | 0 | 8 | 21% | 200 | 30 | 79% |
| 5 | 0 | 0 | 0% | 100 | 20 | 100% |
| 6 | 0 | 4 | 7% | 100 | 53 | 93% |
| 7 | 0 | 0 | NA | 200 | 0 | NA |
| 8 | 0 | 0 | NA | 200 | 0 | NA |
| 9 | 0 | 5 | 19% | 100 | 21 | 81% |
| 10 | 0 | 0 | NA | 200 | 0 | NA |
| 11 | 0 | 4 | 7% | 80 | 53 | 93% |
| 12 | 0 | 9 | 12% | 100 | 65 | 88% |
| 13 | 0 | 3 | 13% | 150 | 20 | 87% |
| 14 | 0 | 14 | 93% | 100 | 1 | 7% |
| 15 | 0 | 2 | 7% | 160 | 25 | 93% |
| 16 | 0 | 4 | 12% | 175 | 30 | 88% |
| 17 | 0 | 5 | 21% | 180 | 19 | 79% |
| 18 | 0 | 10 | 24% | 180 | 32 | 76% |
| 19 | 0 | 11 | 85% | 100 | 2 | 15% |
| 20 | 0 | 0 | NA | 200 | 0 | NA |
| 21 | 0 | 4 | 15% | 160 | 22 | 85% |
| 22 | 0 | 14 | 23% | 100 | 46 | 77% |
| 23 | 0 | 11 | 23% | 80 | 36 | 77% |
| 24 | 0 | 0 | NA | 200 | 0 | NA |
| 25 | 0 | 3 | 11% | 150 | 24 | 89% |

For pathogen classification, most of the samples, including the polymicrobial sample, were correctly classified based on their morphology and the trapping pressure (FIG. 6B and Table 2). In particular, the pathogens in the polymicrobial sample (#3) displayed different shapes (bacillus vs coccus) and were trapped at different pressure values (FIG. 19). Sample #16 was reported as mixed flora. Samples #1 and #6 were misclassified as Klebsiella-like in the microfluidic systems. Nevertheless, CHROMagar results suggested that these samples contained only Klebsiella spp. Sample #10 reported as E. cloacae in the clinical microbiology lab appeared negative in the microfluidic system. Plating counting and MH broth culture also showed the sample was negative.

TABLE 2

Comparison of pathogen classification by the adaptable microfluidic system and clinical microbiology.

| Sample # | Adaptable microfluidic platform | | | | Microbiology | |
| --- | --- | --- | --- | --- | --- | --- |
| | Bacteria | Shape | Pressure (kPa) | Classification | CHROMagar Microorganism | lab Strain |
| 1 | Yes | Bacilli | 100 | Klebsiella-like | Klebsiella | E. coli |
| 2 | Yes | Bacilli | 180 | E. coli-like | E. coli | E. coli |
| 3 | Yes | Coccus & Bacilli | 0 & 150 | Staphylococcus-like & E. coli-like | Staphylococcus aureus | S. aureus & S. maltophilia |
| 4 | Yes | Bacilli | 200 | E. coli-like | E. coli | E. coli |
| 5 | Yes | Bacilli | 100 | Klebsiella-like | Klebsiella | K. oxytoca |

TABLE 2-continued

Comparison of pathogen classification by the adaptable microfluidic system and clinical microbiology.

| | Adaptable microfluidic platform | | | | Microbiology |
|---|---|---|---|---|---|
| Sample # | Bacteria | Shape | Pressure (kPa) | Classification | CHROMagar Microorganism | lab Strain |
| 6 | Yes | Bacilli | 100 | Klebsiella-like | Klebsiella | S. aureus |
| 7 | No | — | — | Negative | Negative | Negative |
| 8 | No | — | — | Negative | Negative | Negative |
| 9 | Yes | Bacilli | 100 | Klebsiella-like | Klebsiella | K. pneumoniae |
| 10 | No | — | — | Negative | Negative | E. cloacae |
| 11 | Yes | Bacilli | 80 | Pseudomonas-like | Pseudomonas | P. aeruginosa |
| 12 | Yes | Coccus | 100 | Enterococcus-like | Enterococcus | E. faecalis |
| 13 | Yes | Bacilli | 150 | E. coli-like | E. coli | E. coli |
| 14 | Yes | Coccus | 0 | Staphylococcus-like | Staphylococcus aureus | S. aureus |
| 15 | Yes | Bacilli | 160 | E. coli-like | E. coli | E. coli |
| 16 | Yes | Bacilli | 175 | E. coli-like | E. coli & Klebsiella | Mixed flora |
| 17 | Yes | Bacilli | 180 | E. coli-like | E. coli | E. coli |
| 18 | Yes | Bacilli | 180 | E. coli-like | E. coli | E. coli |
| 19 | Yes | Coccus | 0 | Staphylococcus-like | Staphylococcus aureus | S. aureus |
| 20 | No | — | — | Negative | Negative | Negative |
| 21 | Yes | Bacilli | 160 | E. coli-like | E. coli | E. coli |
| 22 | Yes | Coccus | 100 | Enterococcus-like | Enterococcus | E. faecium |
| 23 | Yes | Bacilli | 80 | Pseudomonas-like | Pseudomonas | P. aeruginosa |
| 24 | No | — | — | Negative | Negative | Negative |
| 25 | Yes | Bacilli | 150 | E. coli-like | E. coli | E. coli |

Compared with the results from the clinical microbiology lab, the microfluidic system correctly predicted the existence of bacteria for 96% of the samples. The classification approach yields sensitivity of 94.44%, specificity of 57.14%, positive predictive value of 85%, and negative predictive value of 80% (Table 3). Compared with the CHROMagar results obtained at the same site, which avoids transportation and handling errors, the microfluidic system correctly predicted the existence of bacteria for all samples. The classification approach yields sensitivity of 100%, specificity of 83.33%, positive predictive value of 95%, and negative predictive value of 100% (Table 3). AST was performed in the positive samples. In the control groups, all trapped bacteria grew exponentially over time. The susceptibility profiles were determined by the normalized growth of control groups and antibiotic groups at 2 hr (FIG. 6C). For samples with a single species, 7 samples were resistant (#6, #9, #12, #15, #18, #22, and #25), and 12 samples were sensitive. Similar growth behaviors were observed in the clinical urine analysis, where the growth rates of resistant samples were similar with and without antibiotic. For the polymicrobial sample (#3), both bacteria were susceptible to ciprofloxacin. Representative growth curves for susceptible, resistant, and polymicrobial samples are shown in FIG. 6C-F. These results were in 100% agreement with AST by broth dilution.

TABLE 3

Performance of the adaptable microfluidic system compared with CHROMagar and clinical microbiology.

| Pathogen classification | Adaptable microfluidic platform vs. CHROMagar ™ Orientation (%) | Adaptable microfluidic platform vs. Microbiology lab (%) |
|---|---|---|
| Existence of bacteria | 100 | 96 |
| Sensitivity | 100 | 94.44 |
| Specificity | 83.33 | 57.14 |
| Positive predictive value | 95 | 85 |
| Negative predictive value | 100 | 80 |

Figure 1:
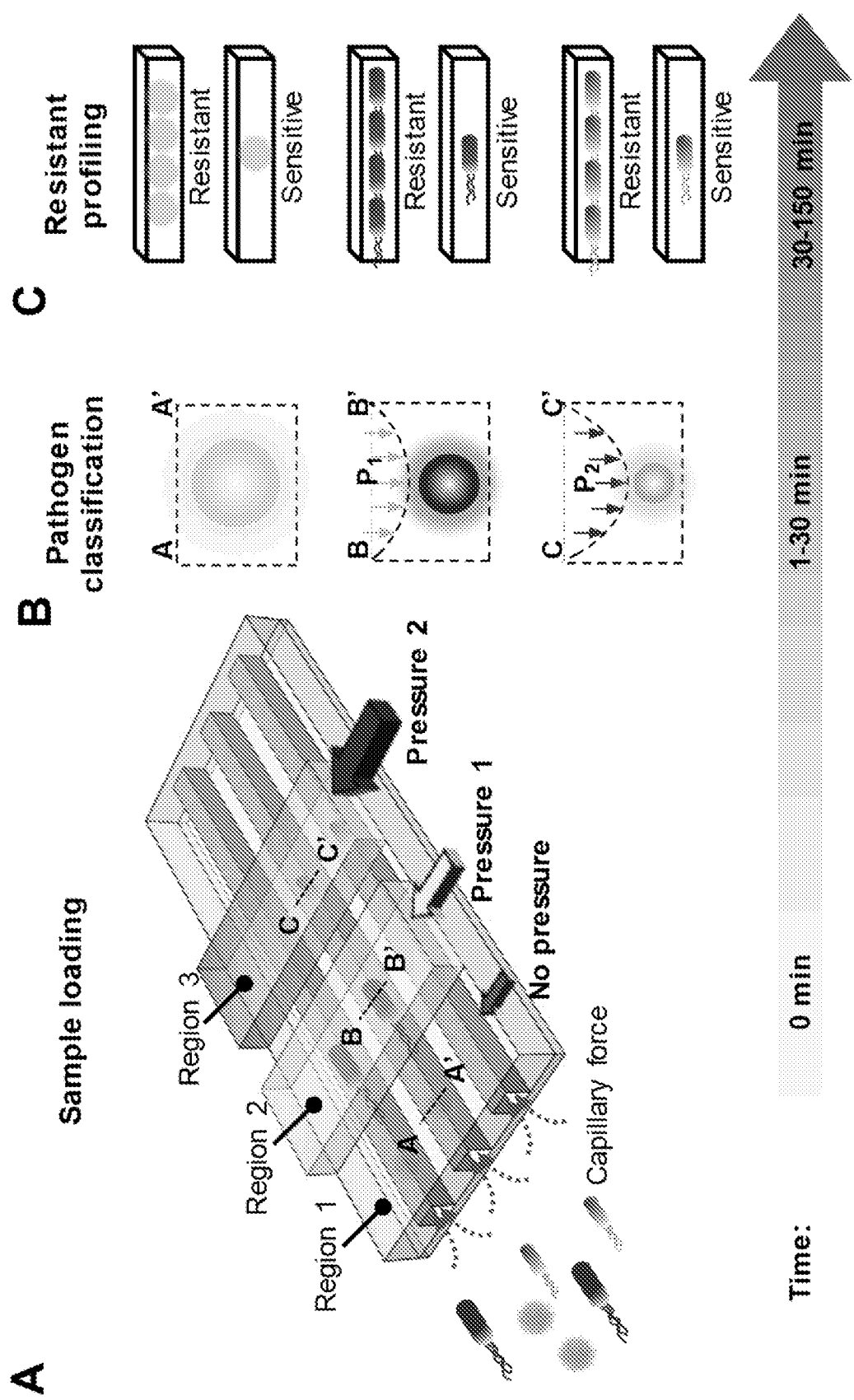
FIG. 1. Single cell pathogen classification and antimicrobial susceptibility testing (AST). (A) Schematic of the adaptable microfluidic device for pathogen classification and AST at the single cell level. Bacterial pathogens are loaded into the channels automatically by capillary force. (B) Cross-section profiles of the channel under different pneumatic pressures. Bacteria are trapped in different regions of the channels and classified according to the applied pressure, which dynamically adjusts the height of the channel. (C) Antimicrobial susceptibility is determined by monitoring phenotypic growth of the bacteria in the presence of antibiotics. (D) Microfluidic separation of three bacterial species by the tunable microfluidic device. S. epidermidis, M. bacteremicum, and E. coli were fluorescently stained, mixed, and loaded to the microfluidic system to demonstrate the pathogen separation. Images are representative of three independent tests. Scale bar, 10 μm. (E) Distributions of the bacteria in regions with 0, 150, and 200 kPa applied pressure in the microchannels. Data represent mean±SEM (n=3). (F). Related to FIG. 1A, with three different bacteria shapes and sizes shown schematically in broken lines. The figure shows the microfluidic device 100, a microfluidic bacteria trapping channel 102, a right side 101c of a bacteria trapping channel, an inlet 105, a bottom 101d, an outlet 101b, a first pneumatic control channel 103 configured perpendicularly to the microfluidic channel 102, and a second pneumatic control channel 104, also configured perpendicularly to the microfluidic channel 102. As explained below, evaporation of liquid that contains liquid biological samples introduced into the microfluidic device 100 may occur at the inlet 105 and at the outlet 101b. (G). Related to FIG. 1A. Front view of microfluidic device depicted in FIG. 1A. Shown is the microfluidic device 100, the first pneumatic control channel 103, three bacteria trapping microfluidic channels 102, a right side 101c of the bacteria trapping channel 102, the left side 101a of a bacteria trapping channel 102, and the bottom 101d. (H). Related to FIG. 1A. Top view of microfluidic device depicted in FIG. 1A. Shown is the microfluidic device 100, three microfluidic bacteria trapping channels 102 configured to trap bacteria, a left side 101a of a bacteria trapping channel 102, the right side 101c of a bacteria trapping channel 102, the first pneumatic control channel 103, the second pneumatic control channel 104, the outlet 101b, and three inlets 105.
Figure 1:
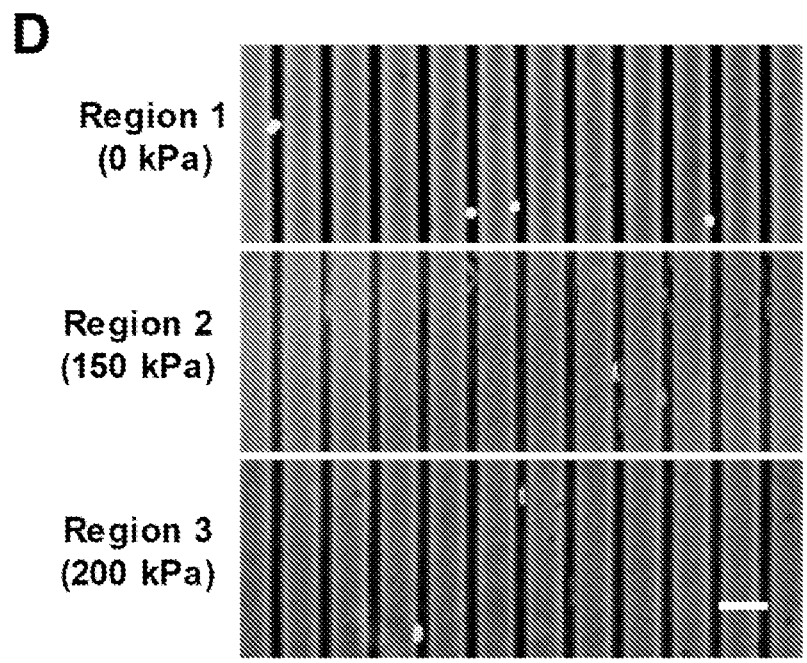
Figure 1:
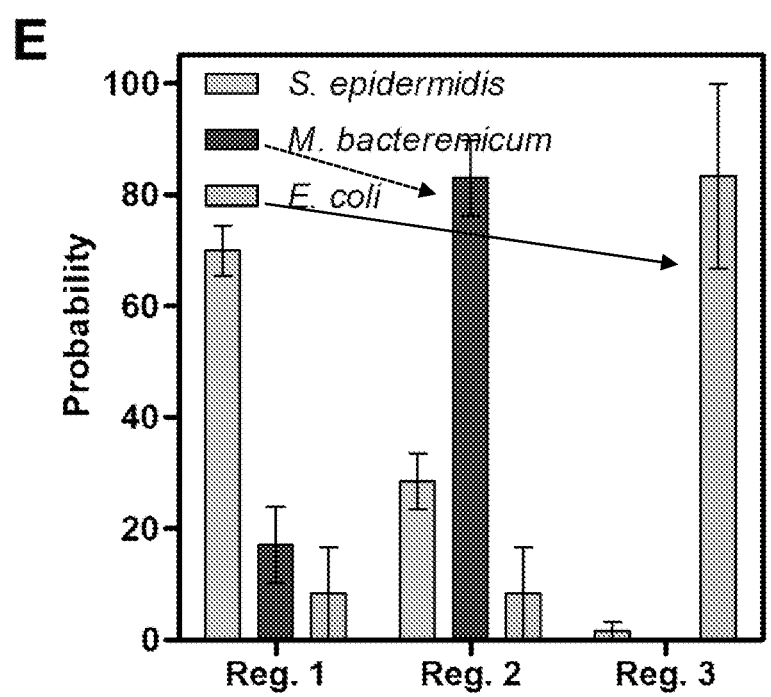
Figure 1:
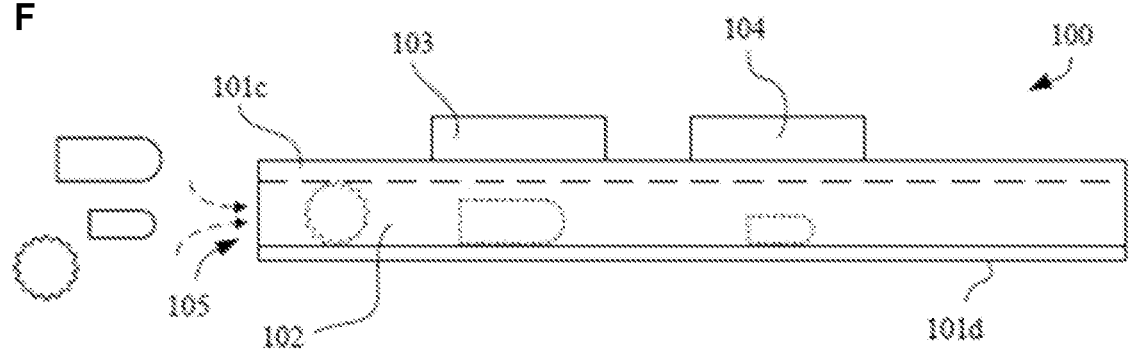
Figure 1:
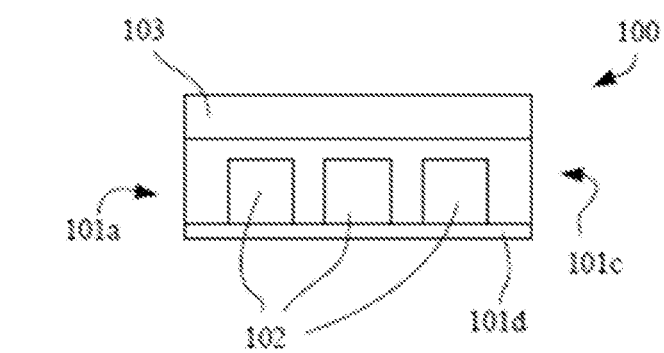
Figure 1:
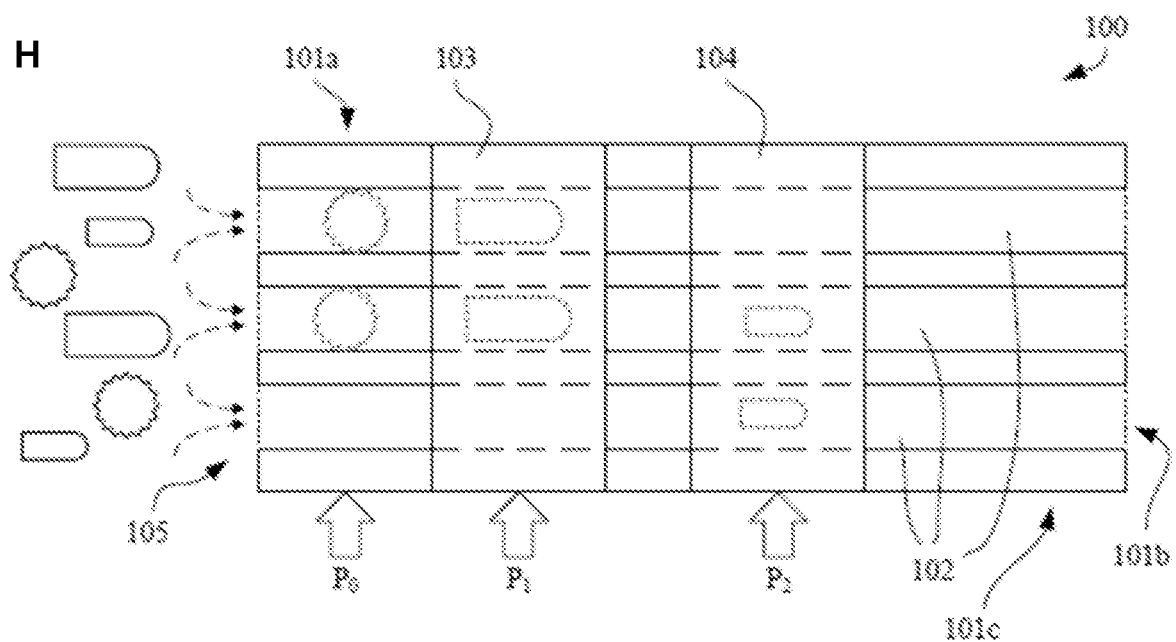
Figure 5:
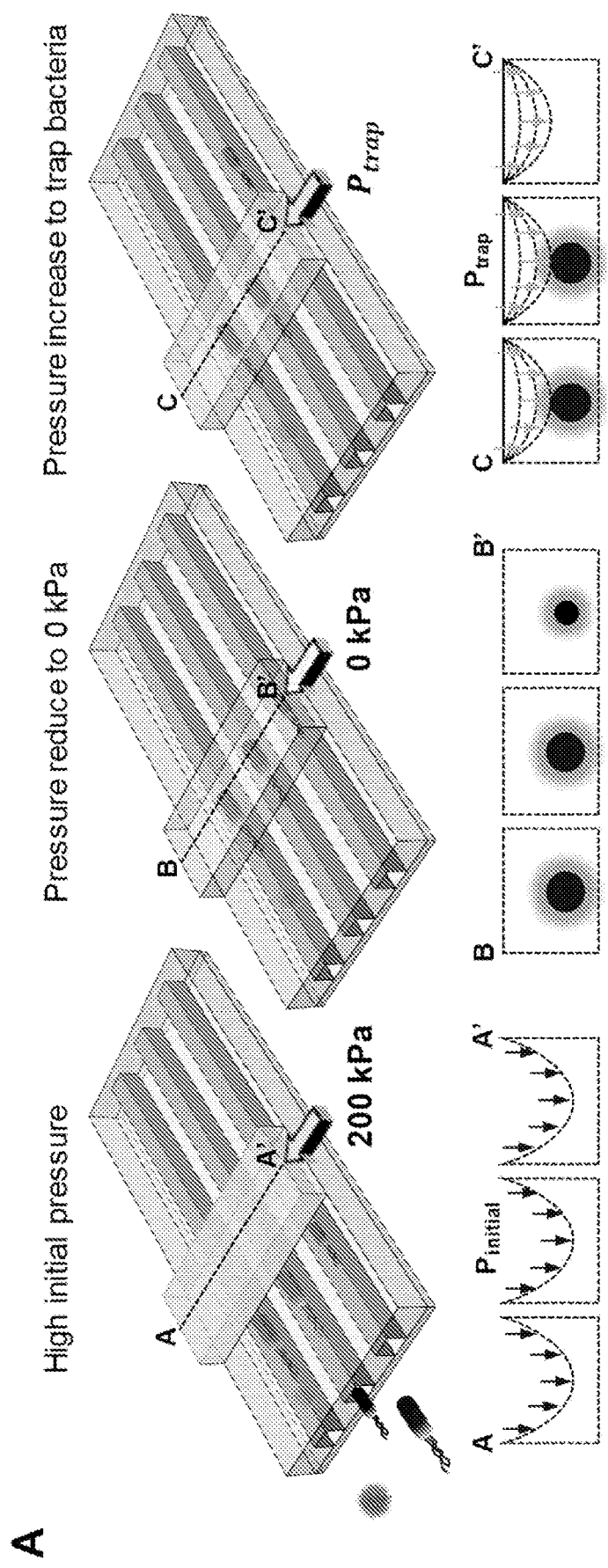
FIG. 5. Procedure for single cell AST of clinical samples with unknown bacteria. (A) The schematic view of the single cell AST procedure for clinical samples with blinded bacteria and the corresponding cross-section profiles of the bottom channels. A high pressure (200 kPa) is first applied to confirm the existence of bacteria in the sample. Then, the applied pressure is released and gradually increased from zero to identify the minimum trapping pressure for pathogen classification. (B) Procedure to identify bacteria species in clinical samples with blinded pathogens. Samples are first confirmed for the presence of bacteria. Positive samples are characterized based on the shape (rod or spherical) and size (minimum trapping pressure) for pathogen classification. Five groups, Staphylococcus-like, Enterococcus-like, Pseudomonas-like, Klebsiella-like and E. coli-like, are classified. AST is performed in the same microfluidic device. Polymicrobial samples are identified based on pathogen classification and antimicrobial susceptibility. (C) Related to FIG. 5A. Shown is the microfluidic device 100, three microfluidic bacteria trapping channels 102, the left side 101a of a microfluidic bacteria trapping channel 102, the right side 101c of a microfluidic bacteria trapping channel 102, three inlets 105, a first pneumatic channel 103, and the outlet 101b. Bacteria that have been introduced into the microfluidic bacteria trapping channels 102 via capillary action of a sample through inlets 105 are depicted schematically with broken lines. Pressure ($P_{high}$) is applied to the first pneumatic channel 103. (D) Related to FIG. 5A. Shown is the microfluidic device 100, three microfluidic bacteria trapping channels configured to trap bacteria 102, the left side 101a of a microfluidic bacteria trapping channel 102, the right side 101c of a microfluidic bacteria trapping channel 102, three inlets 105, a first pneumatic channel 103, and three outlets 101b. Bacteria are shown schematically with broken lines. No pressure is applied ($P_0$). (E) Related to FIG. 5A. Shown is the microfluidic device 100, three microfluidic bacteria trapping channels 102, the left side 101a of a microfluidic bacteria trapping channel 102, the right side 101c of a microfluidic bacteria trapping channel 102, inlets 105, a first pneumatic channel 103, and an outlet 101b. Bacteria that have been trapped in two of the microfluidic bacteria trapping channels 102 are shown schematically with broken lines under trapping pressure ($P_{trap}$), as is a single bacterium that was able to pass through the trapping pressure.
Figure 5:
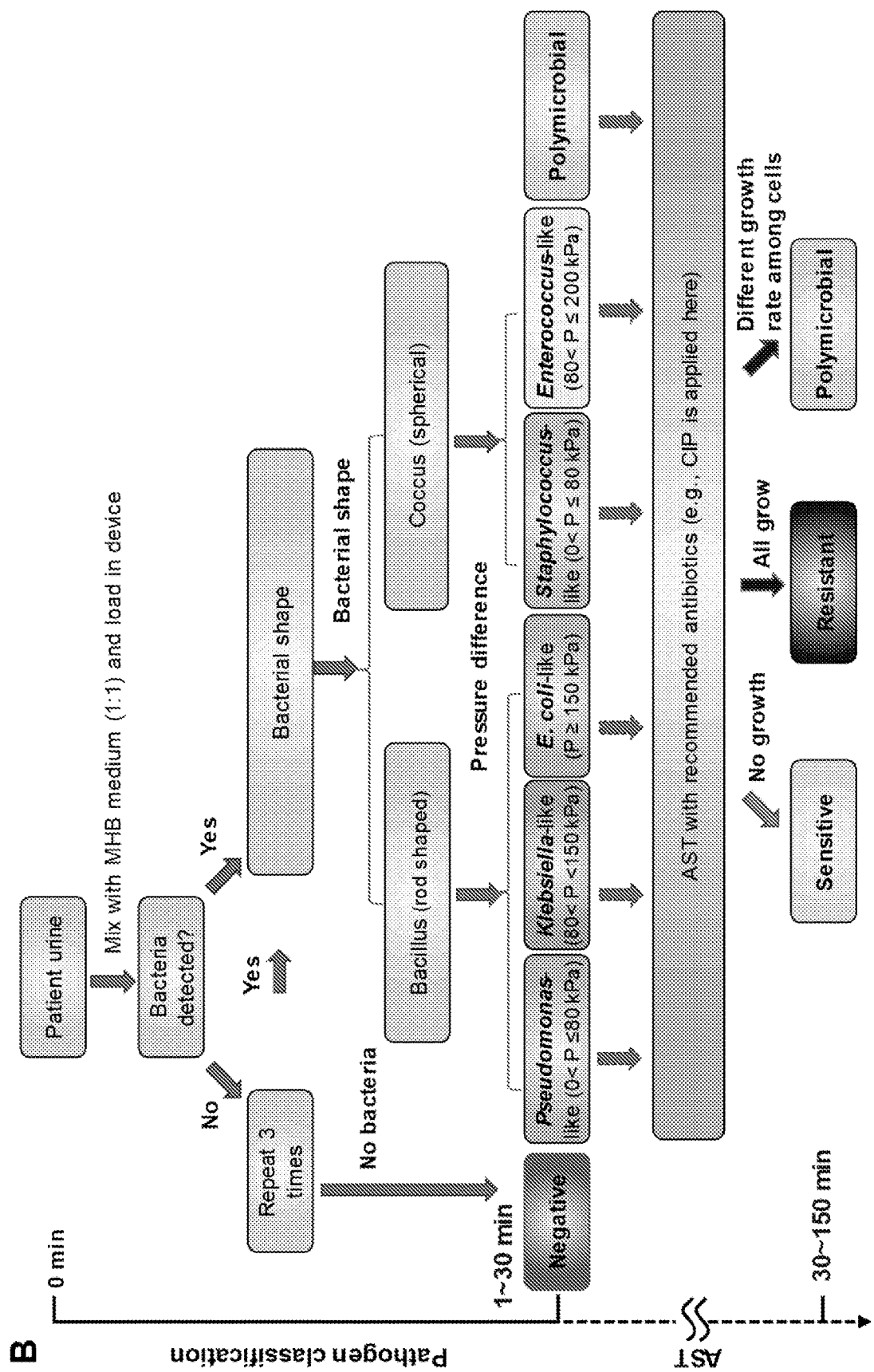
Figure 5:
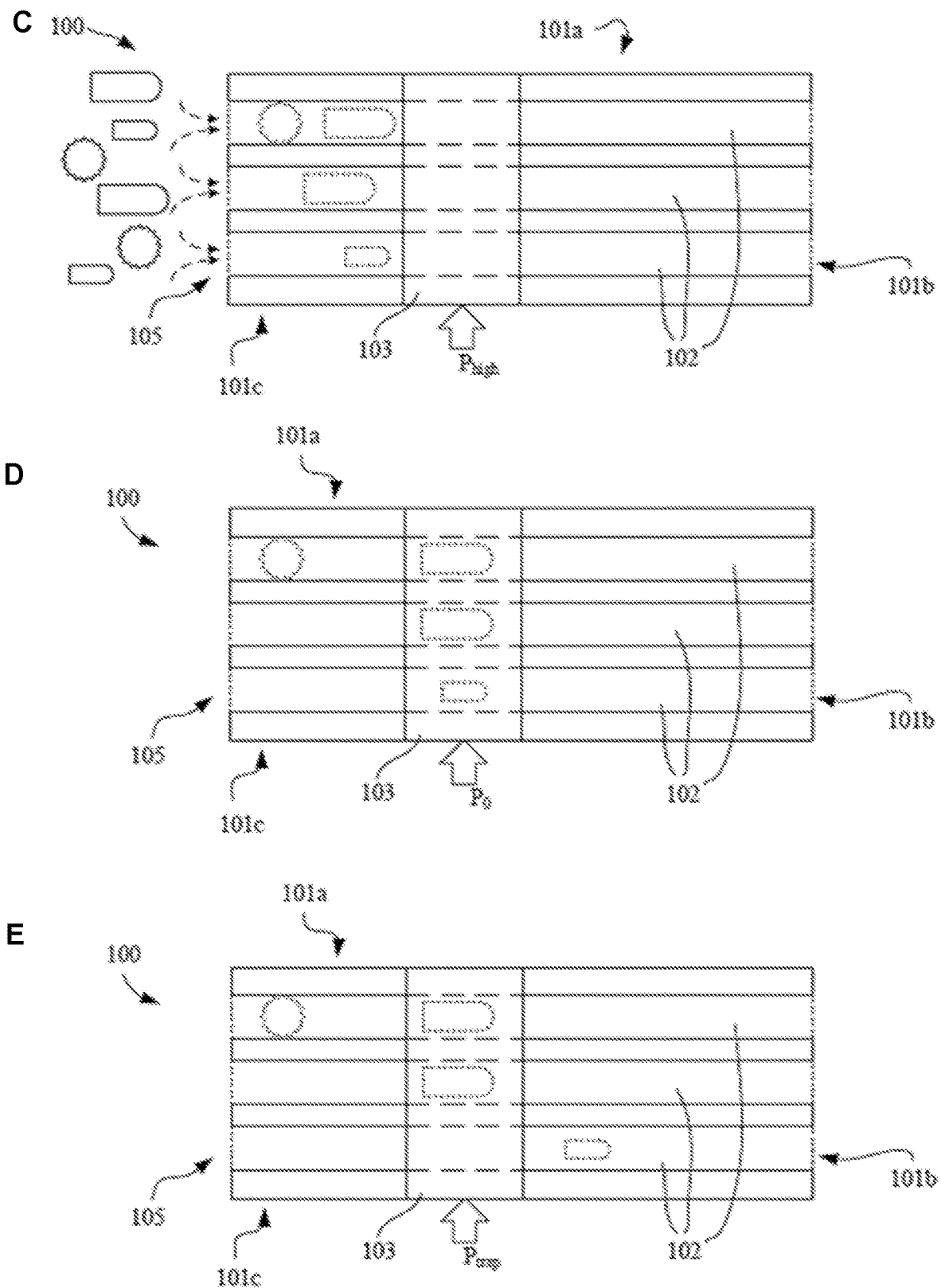

It will be recognized from the foregoing that Part I of this disclosure provides a demonstration of an adaptable microfluidic system for rapid pathogen classification and AST at the single cell level. Unlike colony morphology and Gram stain, the pathogen classification approach is based on microfluidic separation and microscopic inspection. The variability in the dimensions of individual bacteria is captured either by the spatial distribution with multiple pressure regions (i.e. regions of multiple microchannel heights; FIG. 1) or adjusting the pressure dynamically (i.e. changing the microchannel heights over time; FIG. 5). The microfluidic approach separates bacteria according to size and shape, and identifies samples with multiple pathogens for polymicrobial infection detection. Compared to other AST approaches, it allows both pathogen classification and AST in the same device. The microfluidic system is capable of handling clinical samples, such as human urine and blood cultures. The assay times for pathogen classification and AST can be as short as 30 min for E. coli and 60 min for S. aureus, which are the approximate doubling times of the bacteria in our experimental condition.

An element of the adaptable microfluidic system is the sample loading process. In particular, the bacteria are driven into the channels by capillary flow, which can be implemented relatively easily and does not require supporting equipment, such as a pump or a pressure source, or electrokinetic loading. In embodiments, the device is free of any type of electrophoresis, such as dielectrophoresis. In embodiments, the bacteria trapping channels do not include microelectrodes, and no electric current is introduced into the trapping channels. The microfluidic channel also serves as a physical filter to selectively load bacterial pathogens into the observation area and facilitate single cell analysis. In embodiments, the loading process handles a relatively small volume (~20 µl) and the loading time depends on the bacterial concentration. For instance, it takes less than three minute for samples with $10^7$ and almost 30 min for sample with a low concentration (e.g., $10^3$-$10^4$ cfu/mL). Using the current design protocol as a non-limiting example, we have demonstrated trapping of samples with bacteria from $5 \times 10^3$ to $10^8$ cfu/ml. This range covers the concentration relevant for urinary tract infection (UTI) diagnostics. To provide accurate quantitation for samples with a large range of concentrations and identify flora contamination, the number of channels can be increased to handle numerous bacteria with a larger volume of sample. Furthermore, sample interfaces, integrated microfluidic concentrator, and real-time imaging analysis techniques can be incorporated into the microfluidic system to automate the sample loading process and improve the quantification accuracy.

We demonstrate the adaptable microfluidic system for single cell pathogen classification and AST using blinded clinical urine samples. Urine is the most common specimen sent to a clinical microbiology laboratory, yet up to 75% of these specimens are negative. In embodiments, the disclosure facilitates rapidly determining the presence of bacteria and classifying them according to their shape and size. A rapid, urine test capable of ruling out or confirming the presence of bacteria at a clinically relevant concentration is expected to improve patient care and clinical lab workflow. The classification scheme in this disclosure (i.e., *Staphylococcus*-like, *Enterococcus*-like, *Pseudomonas*-like, *Klebsiella*-like, and *E. coli*-like) is in non-limiting embodiments tailored to identify the most common pathogens of UTI. In particular, *E. coli* is the cause of most community-acquired and healthcare-associated UTIs. Basic classification of the predominant pathogen in a sample can assist in the selection of appropriate antibiotics for susceptibility testing or treatment and/or of a panel of molecular probes (e.g., PCR primers or hybridization probes) for more precise speciation. Of significance for therapeutic intervention is that AST of the bacteria can be determined in as little as 30 minutes using the adaptable microfluidic system. Classification of other rod-shaped bacteria (*bacillus*), such as *K. pneumoniae* and *P. aeruginosa*, are critical for UTI diagnostics, since these bacteria maybe treated with different antibiotics compared to *E. coli* due to their high rates of antimicrobial resistance. Identifying *Staphylococcus* spp. and *Enterococcus* spp. will also provide clinically useful information, since these Gram-positive bacteria are common causes of UTI and require different treatment options.

The following Materials and Methods were used to obtain the results discussed above for Part I of this disclosure.

Materials and Methods

This disclosure relates to an adaptable microfluidic system for rapid pathogen classification and AST at the single cell level. Pathogen classification is achieved by a tunable microfluidic channel for size-based separation and phenotypic AST is performed in the same channel. We studied four features of this platform. Firstly, we calibrated this device's ability to separate bacteria of different sizes, including two ATCC strains and one uropathogenic clinical isolate. Secondly, we demonstrated polymicrobial infection detection and studied the resistance profile for each strain independently. This feature has been tested using two sets of spiked samples. One set contains two different bacterial species (*E. coli* and *S. epidermidis*) and the other set contains two different strains of *E. coli* (EC137 and EC136). Thirdly, we tested the performance of the platform with different *E. coli*-positive clinical samples, including 10 human blood cultures and 6 urine samples. Furthermore, we used 25 clinical urine samples. The pathogens were detected and classified in the channels and the ciprofloxacin resistance profiles were revealed subsequently.

Bacterial Strains

There are four bacterial strains included in this disclosure. The *S. epidermidis* (ATCC 12228) and *M. bacteremicum* (ATCC 25791) are from American Type Culture Collection (ATCC). Uropathogenic *E. coli* (EC137 and EC136) were isolated from patient urine samples.

Clinical Samples

Clinical samples were obtained from the clinical microbiology laboratory of the Penn State Milton S. Hershey Medical Center. The procedure was approved by the Pennsylvania State University Institutional Review Board. *E. coli*-positive blood cultures (n=10) and urine samples (n=6) were mixed with MH broth at ratio of 1:10 with and without ciprofloxacin (4 µg/mL). 25 clinical urine samples with blinded pathogens were examined using CHROMagar and the microfluidic system. The results were compared with clinical microbiology culture results. These samples were mixed with MH broth at a ratio of 1:1 with and without ciprofloxacin (4 µg/mL). Some samples were stored with glycerol (25% v/v) at −80° C. and were pre-incubated for 30 min at 37° C. before use. The bacterial morphology was visually examined with optical microscopy (20× or 40× objective).

Reagents

Three different antibiotics, including ciprofloxacin (CIP), ampicillin (AMP), and oxacillin (OXA), were employed in this disclosure. The antibiotics were obtained from Sigma-Aldrich. Human whole blood samples were obtained from the Valley Biomedical Product & Service, Inc. Na Heparin was applied as the anticoagulant. Fluorescent dyes, SYTO 9, SYTO 85, and Hoechst 33342, were applied for bacterial staining to calibrate the spatial distributions of different bacteria. The dyes were obtained from Thermo Fisher Scientific. Triton X-100 and IGEPAL CA-630 (Sigma-Aldrich) were applied for blood cell lysis. PDMS (Sylgard 184) for channel fabrication was obtained from Dow Corning.

Microfluidic Device

A multilayer microfluidic device with tunable channels was developed for rapid pathogen classification and AST as a non-limiting demonstration. The device was fabricated by bonding two PDMS layers (FIG. 7). The top layer serves as a pneumatic control channel and the channels in the bottom layer trap bacteria for phenotypic culture. The mold for the top layer was fabricated by patterning a SU-8 layer on silicon wafer. The channel width is 100 and the channel interval is 100 PDMS (at ratio of 5:1 between pre-polymer and cross-linker) was poured on the mold and cured for 1 hr at 80° C. The bottom microchannel mold was fabricated on a silicon wafer using a reactive-ion etching (ME) process with a patterned photoresist layer. The width of the microchannels is 2.0 µm and the height of the microchannels is 1.32 PDMS (at ratio of 20:1 between pre-polymer and cross-linker) was spin-coated on the mold for 5 min at 3000 rpm and cured for 3 hr at 65° C. The top control channel layer was peeled off and bonded with the bottom microchannel layer after 5 min air plasma treatment (PDC-001, Harrick Plasma). The device was incubated for 30 min at 65° C. In addition, the device was bonded with a glass slide after a second air plasma treatment step. Finally, the device was incubated at 80° C. for 5 min. The microfluidic device was loaded on a microscope (Leica DMI4000B) with a thermal stage for real-time monitoring of the bacterial growth. The bacteria in the adaptable microfluidic system was captured by a CCD camera (SensiCam QE, PCO) and the growth of the bacteria was measured using ImageJ. Imaging was performed from the bottom of the device, but could also be performed from the top.

Single Cell Antimicrobial Susceptibility Testing

E. coli, S. epidermidis, and M. bacteremicum were cultured in Mueller Hinton broth, Nutrient broth, and ATCC medium 1395, respectively. The bacteria were cultured to an optical density at 600 nm ($OD_{600}$) around 0.2 (measured with Nanodrop 2000, Thermo Scientific) and diluted to $5 \times 10^5$ cfu/mL following the CLSI guideline. The concentrations of ciprofloxacin for E. coli and M. bacteremicum were 4 µg/mL and 2 µg/mL, respectively. The concentration of oxacillin for S. epidermidis was 4 µg/mL. A 20 µl sample was loaded into the inlet of the microchannel. Culture medium was applied to immerse the whole device. The device was then loaded on a microscope (Leica DMI4000B) thermal stage for real-time monitoring (SensiCam QE, PCO) of the bacterial growth. The length of the bacteria occupying the microchannel was measured in ImageJ (imagej.nih.gov/ij/). To model the polymicrobial infection with different species, E. coli (EC137) and S. epidermidis were cultured to $OD_{600}$ around 0.2, mixed at ratio of 1:1, and diluted to a final concentration of $1 \times 10^6$ cfu/mL with and without ampicillin (8 µg/mL). To mimic the polymicrobial infection with different strains, E. coli (EC137 and EC136) were mixed at a ratio of 10:1 and diluted to a final concentration of $5 \times 10^6$ cfu/mL with and without ampicillin. In this embodiment, the antibiotic resistance was determined as 50% reduction in the growth rate (or two-fold difference in growth rate) in the antibiotic group based on the distribution of the growth rate of single cells. In particular, we define the threshold value based on the standard derivation of single cell growth and t-statistics (two-tailed, unpaired). In our calibration tests, the standard deviations of the growth rate were below 25% of the mean (in the worst case scenario). In the calculation, the degree of freedom was 8, since at least 5 bacteria were used in each group. A 50% reduction in growth rate is equivalent to a p-value of approximately 0.022.

Bacteria Detection in Human Whole Blood

To detect bacteria in whole blood, E. coli (EC137) was spiked into human whole blood. The bacteria were cultured to $OD_{600}$ around 0.2, stained with SYTO 9, washed 3 times, and spiked into 1 mL human whole blood. The final concentration of the bacteria ranged from $8 \times 10^3$ to $8 \times 10^6$ cfu/mL. The sample was centrifuged for 3 min at 200 g to remove the majority of the blood cells. The plasma (~400 µL) was transferred to another tube and 1 mL Triton X-100 (1% in MH broth medium) was added to lyse the remaining blood cells and debris. The sample was incubated for 2 min at 37° C. and then centrifuged for 3 min at 1000 g. The supernatant was removed and 1.5 mL IGEPAL CA-630 (1% in MR broth medium) was added. The sample was incubated for 2 min at 37° C. and then centrifuged for 3 min at 1000 g. The supernatant was carefully removed and the twenty micro liter sample was loaded into the channel.

Part I References. The Part I and Part II Reference Listings Provided with this Application are not an Indication that any Reference is Material to Patentability.

1. H. M. Zowawi, P. N. A. Harris, M. J. Roberts, P. A. Tambyah, M. A. Schembri, M. D. Pezzani, D. A. Williamson, D. L. Paterson, The emerging threat of multidrug-resistant Gram-negative bacteria in urology. *Nat Rev Urol* 12, 570-584 (2015).
2. *"Global antimicrobial resistance surveillance system—Manual for early implementation,"* (World Health Organization, 2015).
3. *"Antibiotic resistance threats in the United States,"* (Centers for Disease Control and Prevention, 2013).
4. I. Brook, H. M. Wexler, E. J. C. Goldstein, Antianaerobic Antimicrobials: Spectrum and Susceptibility Testing. *Clinical Microbiology Reviews* 26, 526-546 (2013).
5. M. R. Pulido, M. Garcia-Quintanilla, R. Martin-Pena, J. M. Cisneros, M. J. McConnell, Progress on the development of rapid methods for antimicrobial susceptibility testing. *Journal of Antimicrobial Chemotherapy* 68, 2710-2717 (2013).
6. L. B. Reller, M. Weinstein, J. H. Jorgensen, M. J. Ferraro, Antimicrobial Susceptibility Testing: A Review of General Principles and Contemporary Practices. *Clinical Infectious Diseases* 49, 1749-1755 (2009).
7. M. Davenport, K. E. Mach, L. M. D. Shortliffe, N. Banaei, T. H. Wang, J. C. Liao, New and developing diagnostic technologies for urinary tract infections. *Nat Rev Urol* 14, 296-310 (2017).
8. K. E. Mach, P. K. Wong, J. C. Liao, Biosensor diagnosis of urinary tract infections: a path to better treatment? *Trends in pharmacological sciences* 32, 330-336 (2011).
9. J. M. A. Blair, M. A. Webber, A. J. Baylay, D. O. Ogbolu, L. J. V. Piddock, Molecular mechanisms of antibiotic resistance. *Nat Rev Micro* 13, 42-51 (2015).
10. Y. Li, X. Yang, W. Zhao, Emerging Microtechnologies and Automated Systems for Rapid Bacterial Identification and Antibiotic Susceptibility Testing. *SLAS TECHNOLOGY: Translating Life Sciences Innovation* 0, 2472630317727519 (2017).
11. M. L. Y. Sin, K. E. Mach, P. K. Wong, J. C. Liao, Advances and challenges in biosensor-based diagnosis of infectious diseases. *Expert Review of Molecular Diagnostics* 14, 225-244 (2014).
12. K. A. Bauer, K. K. Perez, G. N. Forrest, D. A. Goff, Review of Rapid Diagnostic Tests Used by Antimicrobial Stewardship Programs. *Clinical Infectious Diseases* 59, S134-S145 (2014).
13. G. Czilwik, T. Messinger, O. Strohmeier, S. Wadle, F. von Steffen, N. Paust, G. Roth, R. Zengerle, P. Saarinen, J. Niittymaki, K. McAllister, O. Sheils, J. O'Leary, D. Mark, Rapid and fully automated bacterial pathogen detection on a centrifugal-microfluidic LabDisk using highly sensitive nested PCR with integrated sample preparation. *Lab on a Chip* 15, 3749-3759 (2015).
14. K. S. Park, C.-H. Huang, K. Lee, Y.-E. Yoo, C. M. Castro, R. Weissleder, H. Lee, Rapid identification of health care—associated infections with an integrated fluorescence anisotropy system. *Science Advances* 2, (2016).
15. Y. Zhu, L. Qiao, M. Prudent, A. Bondarenko, N. Gasilova, S. B. Moller, N. Lion, H. Pick, T. Gong, Z. Chen, P. Yang, L. T. Lovey, H. H. Girault, Sensitive and fast identification of bacteria in blood samples by immunoaffinity mass spectrometry for quick BSI diagnosis. *Chemical Science* 7, 2987-2995 (2016).
16. A. Machen, T. Drake, Y. F. Wang, Same Day Identification and Full Panel Antimicrobial Susceptibility Testing of Bacteria from Positive Blood Culture Bottles Made Possible by a Combined Lysis-Filtration Method with MALDI-TOF VITEK Mass Spectrometry and the VITEK2 System. *PLOS ONE* 9, e87870 (2014).
17. C. H. Chen, Y. Lu, M. L. Y. Sin, K. E. Mach, D. D. Zhang, V. Gau, J. C. Liao, P. K. Wong, Rapid Antimicrobial Susceptibility Testing Using High Surface-to-Volume Ratio Microchannels. *Analytical chemistry* 82, 1012 (2010).
18. N. J. Cira, J. Y. Ho, M. E. Dueck, D. B. Weibel, A self-loading microfluidic device for determining the minimum inhibitory concentration of antibiotics. *Lab on a Chip* 12, 1052-1059 (2012).
19. K. P. Kim, Y.-G. Kim, C.-H. Choi, H.-E. Kim, S.-H. Lee, W.-S. Chang, C.-S. Lee, In situ monitoring of antibiotic susceptibility of bacterial biofilms in a microfluidic device. *Lab on a Chip* 10, 3296-3299 (2010).
20. C.-Y. Jiang, L. Dong, J.-K. Zhao, X. Hu, C. Shen, Y. Qiao, X. Zhang, Y. Wang, R. F. Ismagilov, S.-J. Liu, W. Du, High-Throughput Single-Cell Cultivation on Microfluidic Streak Plates. *Applied and Environmental Microbiology* 82, 2210-2218 (2016).
21. M. W. Kadlec, D. You, J. C. Liao, P. K. Wong, A Cell Phone-Based Microphotometric System for Rapid Antimicrobial Susceptibility Testing. *J Lab Autom* 19, 258-266 (2014).
22. J. Avesar, D. Rosenfeld, M. Truman-Rosentsvit, T. Ben-Arye, Y. Geffen, M. Bercovici, S. Levenberg, Rapid phenotypic antimicrobial susceptibility testing using nanoliter arrays. *Proceedings of the National Academy of Sciences* 114, E5787-E5795 (2017).
23. J. D. Besant, E. H. Sargent, S. O. Kelley, Rapid electrochemical phenotypic profiling of antibiotic-resistant bacteria. *Lab on a Chip* 15, 2799-2807 (2015).
24. C. Zhu, Q. Yang, L. Liu, S. Wang, Rapid, Simple, and High-Throughput Antimicrobial Susceptibility Testing and Antibiotics Screening. *Angewandte Chemie International Edition* 50, 9607-9610 (2011).
25. J. R. Carey, K. S. Suslick, K. I. Hulkower, J. A. Imlay, K. R. C. Imlay, C. K. Ingison, J. B. Ponder, A. Sen, A. E. Wittrig, Rapid Identification of Bacteria with a Disposable Colorimetric Sensing Array. *Journal of the American Chemical Society* 133, 7571-7576 (2011).
26. T. Liu, Y. Lu, V. Gau, J. C. Liao, P. K. Wong, Rapid antimicrobial susceptibility testing with electrokinetics enhanced biosensors for diagnosis of acute bacterial infections. *Annals of biomedical engineering* 42, 2314-2321 (2014).
27. K. E. Mach, R. Mohan, E. J. Baron, M. C. Shih, V. Gau, P. K. Wong, J. C. Liao, A biosensor platform for rapid antimicrobial susceptibility testing directly from clinical samples. *The Journal of urology* 185, 148-153 (2011).
28. N. G. Schoepp, T. S. Schlappi, M. S. Curtis, S. S. Butkovich, S. Miller, R. M. Humphries, R. F. Ismagilov, Rapid pathogen-specific phenotypic antibiotic susceptibility testing using digital LAMP quantification in clinical samples. *Science translational medicine* 9, eaal3693 (2017).
29. M. Dou, D. C. Dominguez, X. Li, J. Sanchez, G. Scott, A Versatile PDMS/Paper Hybrid Microfluidic Platform for Sensitive Infectious Disease Diagnosis. *Analytical Chemistry* 86, 7978-7986 (2014).
30. K. Syal, R. Iriya, Y. Yang, H. Yu, S. Wang, S. E. Haydel, H. Y. Chen, N. Tao, Antimicrobial Susceptibility Test with Plasmonic Imaging and Tracking of Single Bacterial Motions on Nanometer Scale. *Acs Nano* 10, 845-852 (2016).
31. LongoG, L. Alonso Sarduy, L. M. Rio, BizziniA, TrampuzA, NotzJ, DietlerG, KasasS, '. *Nat Nano* 8, 522-526 (2013).
32. Y. Tang, L. Zhen, J. Liu, J. Wu, Rapid Antibiotic Susceptibility Testing in a Microfluidic pH Sensor. *Analytical Chemistry* 85, 2787-2794 (2013).
33. A. M. Kaushik, K. Hsieh, L. Chen, D. J. Shin, J. C. Liao, T.-H. Wang, Accelerating bacterial growth detection and antimicrobial susceptibility assessment in integrated picoliter droplet platform. *Biosensors and Bioelectronics* 97, 260-266 (2017).
34. J. Q. Boedicker, L. Li, T. R. Kline, R. F. Ismagilov, Detecting bacteria and determining their susceptibility to antibiotics by stochastic confinement in nanoliter droplets using plug-based microfluidics. *Lab Chip* 8, 1265-1272 (2008).
35. J. Choi, Y. G. Jung, J. Kim, S. Kim, Y. Jung, H. Na, S. Kwon, Rapid antibiotic susceptibility testing by tracking single cell growth in a microfluidic agarose channel system. *Lab Chip* 13, 280-287 (2013).
36. J. Choi, J. Yoo, M. Lee, E.-G. Kim, J. S. Lee, S. Lee, S. Joo, S. H. Song, E.-C. Kim, J. C. Lee, H. C. Kim, Y.-G. Jung, S. Kwon, A rapid antimicrobial susceptibility test based on single-cell morphological analysis. *Science Translational Medicine* 6, 267ra174-267ra174 (2014).
37. I. Peitz, R. van Leeuwen, Single-cell bacteria growth monitoring by automated DEP-facilitated image analysis. *Lab on a Chip* 10, 2944-2951 (2010).
38. C.-Y. Chung, J.-C. Wang, H.-S. Chuang, Rapid Bead-Based Antimicrobial Susceptibility Testing by Optical Diffusometry. *PLOS ONE* 11, e0148864 (2016).
39. Y. Lu, J. Gao, D. D. Zhang, V. Gau, J. C. Liao, P. K. Wong, Single Cell Antimicrobial Susceptibility Testing by Confined Microchannels and Electrokinetic Loading. *Analytical chemistry*, (2013).
40. O. Baltekin, A. Boucharin, E. Tano, D. I. Andersson, J. Elf, Antibiotic susceptibility testing in less than 30 min using direct single-cell imaging. *Proc Natl Acad Sci USA* 114, 9170-9175 (2017).
41. K. Dupnik, Queuing up for resistance testing. *Science Translational Medicine* 9, (2017).
42. "Methods for Dilution Antimicrobial Susceptibility Tests for Bacteria That Grow Aerobically; Approved Standard-Ninth Edition, CLSI M07-A9," (Clinical and Laboratory Standards Institute (CLSI), 2012).
43. S. A. Golchin, J. Stratford, R. J. Curry, J. McFadden, A microfluidic system for long-term time-lapse microscopy studies of mycobacteria. *Tuberculosis* 92, 489-496 (2012).
44. "Performance standards for antimicrobial susceptibility testing; Twenty-fifth informational supplement. CLSI M100-S25," (Clinical and Laboratory Standards Institute (CLSI), 2015).
45. J. Li, T. Ding, X. Liao, S. Chen, X. Ye, D. Liu, Synergetic effects of ultrasound and slightly acidic electrolyzed water against *Staphylococcus aureus* evaluated by flow cytometry and electron microscopy. *Ultrasonics Sonochemistry* 38, 711-719 (2017).
46. J. M. Monteiro, P. B. Fernandes, F. Vaz, A. R. Pereira, A. C. Tavares, M. T. Ferreira, P. M. Pereira, H. Veiga, E. Kuru, M. S. VanNieuwenhze, Y. V. Brun, S. R. Filipe, M.

G. Pinho, Cell shape dynamics during the staphylococcal cell cycle. *Nature Communications* 6, 8055 (2015).
47. H. van der Weide, J. Brunetti, A. Pini, L. Bracci, C. Ambrosini, P. Lupetti, E. Paccagnini, M. Gentile, A. Bernini, N. Niccolai, D. V.-d. Jongh, I. A. J. M. Bakker-Woudenberg, W. H. F. Goessens, J. P. Hays, C. Falciani, Investigations into the killing activity of an antimicrobial peptide active against extensively antibiotic-resistant *K. pneumoniae* and *P. aeruginosa*. *Biochimica et Biophysica Acta (BBA)—Biomembranes* 1859, 1796-1804 (2017).
48. D.-K. Kim, C. Rathnasingh, H. Song, H. J. Lee, D. Seung, Y. K. Chang, Metabolic engineering of a novel *Klebsiella oxytoca* strain for enhanced 2,3-butanediol production. *Journal of Bioscience and Bioengineering* 116, 186-192 (2013).
49. M. Diaz, V. Ladero, B. del Rio, B. Redruello, M. Fernández, M. C. Martin, M. A. Alvarez, Biofilm-Forming Capacity in Biogenic Amine-Producing Bacteria Isolated from Dairy Products. *Frontiers in Microbiology* 7, (2016).
50. L. Moghadas, M. Shahmoradi, T. Narimani, Antimicrobial activity of a new nanobased endodontic irrigation solution: In vitro study. *Dental Hypotheses* 3, 142 (2012).
51. A. M. Guzmán Prieto, J. Wijngaarden, J. C. Braat, M. R. C. Rogers, E. Majoor, E. C. Brouwer, X. Zhang, J. R. Bayjanov, M. J. M. Bonten, R. J. L. Willems, W. van Schaik, The Two-Component System ChtRS Contributes to Chlorhexidine Tolerance in *Enterococcus faecium*. *Antimicrobial Agents and Chemotherapy* 61, (2017).
52. A. Limayem, R. S. Donofrio, C. Zhang, E. Haller, M. G. Johnson, Studies on the drug resistance profile of *Enterococcus faecium* distributed from poultry retailers to hospitals. *Journal of Environmental Science and Health, Part B* 50, 827-832 (2015).
53. A. Wang, Q. Wang, T. Kudinha, S. Xiao, C. Zhuo, Effects of Fluoroquinolones and Azithromycin on Biofilm Formation of *Stenotrophomonas maltophilia*. *Scientific Reports* 6, 29701 (2016).
54. A. Pompilio, C. Catavitello, C. Picciani, P. Confalone, R. Piccolomini, V. Savini, E. Fiscarelli, apos, D. Antonio, G. Di Bonaventura, Subinhibitory concentrations of moxifloxacin decrease adhesion and biofilm formation of *Stenotrophomonas maltophilia* from cystic fibrosis. *Journal of Medical Microbiology* 59, 76-81 (2010).

Part II

This Part II of this disclosure relates to improved approaches to introducing probes into, and detecting bacteria. It is useful at least because the emergence of multidrug-resistant pathogens is a major healthcare threat and the annual associated healthcare cost is over $20 billion[1]. For example, several Gram-negative pathogens, including *E. coli*, *P. aeruginosa* and *K. pneumoniae*, are common causes of healthcare-associated and community-acquired infections (e.g., pneumonia, urinary tract infection and bloodstream infections). Increasingly, these bacteria are also found to be resistant to first-line and second-line antibiotics. The conventional culture-based assays in clinical microbiology require at least 2-3 days and can be even longer for slow-growing bacteria. This significant delay in microbiological analysis leads to empiric broad-spectrum antibiotic usage by healthcare providers resulting in unnecessary treatment, ineffective antibiotic selection, and the potential for poor clinical outcome. Furthermore, the very use of these drugs creates a selective pressure that leads to the emergence of multidrug-resistant pathogens. For these reasons, novel technologies for rapidly identifying bacterial pathogens and their antibiotic resistance profiles will have a significant impact on patient care and antimicrobial stewardship[2]. Part II of this disclosure addresses this need.

In more detail, in a typical clinical microbiology workflow, the first step involves receipt and processing of a specimen for culture. Culture based methods, which can include colony morphology (form, elevation, and appearance), Gram stain, and biochemical or mass spectrometry phenotyping, take days to finalize the identification of the bacteria. The culture procedure represents a major time limiting step for the microbiology workflow. To perform antimicrobial susceptibility testing (AST), additional broth microdilution cultures phenotypically determine the growth of the culture isolate in the presence of serial dilutions of antibiotics. These AST procedures typically require an additional 1-2 days and a laboratory setting. Molecular approaches, such as multiplex PCR, can either be performed directly from specimens or bacterial isolates. Compared with culture-based methods, molecular analysis is capable of identifying pathogens rapidly because the target gene can be amplified much faster than natural bacterial growth. However, amplification techniques typically do not quantify a clinically relevant concentration of viable bacteria or provide robust AST results. They also require moderate to high complexity testing. These issues limit their practicality in point-of-care diagnostic applications. Recently, molecular probes, droplet microfluidics, digital LAMP quantification, and electrochemical biosensors have enabled culture-free detection of bacteria in physiological samples with minimal processing[3-9]. Integrated pathogen identification and AST systems have also been demonstrated by high-resolution melt-curve analysis and electrochemical biosensors[10, 11]. Nevertheless, the cost, complex procedures, bulky instrumentation and the intensive labor requirements present challenges for rapid microbiological analysis. A broad-based technique for comprehensive microbiological analysis in resource-limited settings remains an elusive goal[2, 12].

In this Part II of this disclosure, an approach for single cell pathogen identification by transforming (i.e., delivering) molecular biosensors into viable bacteria using a nanotube assisted microwave electroporation (NAME) technique (FIG. 20A) is provided. The carbon nanotube serves as an antenna for coupling microwave energy to generate a highly localized electric field for microwave electroporation[3-15]. Single cell pathogen identification is achieved by intracellular delivery of double-stranded nucleic acid probes that target species-specific regions of the bacterial 16S rRNA (FIG. 20B)[3, 16, 17]. In this homogeneous sensing scheme, hybridization with the target 16S rRNA displaces the quencher probe from the donor probe allowing the fluorophore to fluoresce. Fluorescence is detected only when the specific probe is hybridized to the target in the bacterium (FIG. 20C). In particular, we investigate the NAME technique for identifying bacterial pathogens at the single cell level. We evaluate the NAME protocol for detecting bacterial pathogens isolated from clinical urine and blood culture. We also demonstrate direct detection of bacteria in patients' urine samples. Furthermore, we apply NAME for single cell pathogen identification and AST by incorporating a microfluidic single cell trapping device.

In embodiments, the disclosure thus provides for use of detectably labeled probes that are introduced into bacteria using the nanotube assisted microwave electroporation. In embodiments, the probes are double-stranded probes. The length of the probes is not particularly limited, provided at least one strand has sufficient complementarity to bind to its target, which in certain embodiments comprises bacterial rRNA. In embodiments, one strand of a double-stranded probe is labeled with a detectable label, and the other strand is conjugated to a moiety that quenches a detectable signal from the detectable label. Thus, when the labeled strand hybridizes to its target, the detectable label is no longer quenched, and a signal from it can be detected using any suitable approach. In embodiments, a fluorophore is conjugated to 5' or 3' end of one strand, and a quencher molecule is conjugated to the complementary strand to the 5' or 3' end of the quencher strand. In embodiments, the double stranded probes are configured so that the quencher and detectable label are at 5' and 3' ends, respectively, or vice versa, provided the detectable label and quencher are in sufficient proximity such that the signal is quenched when the probe is in its double stranded configuration. Thus, alleviation of quencher-mediated suppression of the fluorescence is achieved.

In embodiments, the labeled strand and the quencher strand comprise uneven lengths. In embodiments, either strand comprises from 10-100 nucleotides. In embodiments, the labeled strand comprises 15-30 nucleotides, inclusive, and including all integers there between, and all ranges there between. In embodiments, the labeled strand comprises 22-24 nucleotides, and is complementary to the target of interest, including but not necessarily limited to rRNA. In embodiments, the quencher stand is shorter than the detectable labeled strand. In embodiments, a quencher strand is 5-14 nucleotides long, inclusive, including all integers and ranges of integers there between. In embodiments, the quencher strand is 11-12 nucleotides in length. In embodiments, a universal (UNI) probe that targets a conserved region of the bacterial 16S rRNA can be used for detecting all bacteria. Thus, this aspect of the disclosure is suitable for determining whether any particular sample contains any bacteria, whereby the presence of bacteria is indicated by a signal from the labeled probe that is hybridized to the 16S rRNA, or another suitable nucleic acid target that is specific for bacteria generally, or specific for only certain types of bacteria.

In embodiments, any detectable label can be used, non-limiting examples of which include fluorophores, metals or chemiluminescent moieties, fluorescent particles, quantum dots, etc., provided the detectable label can be quenched, or its intensity shifted to a different wavelength in a fluorescence resonance energy transfer (FRET) process by a suitable quencher moiety conjugated to the quencher strand. In embodiments, one or both strands of the double stranded probes comprise one or more modifications, such as modified phosphodiester linkages, or synthetic inter-nucleoside linkages, such as phosphorothiols, methylphosphonates, phosphoramidites, or morpholinos, or are locked nucleic acids, or peptide nucleic acid conjugates.

In embodiments, any suitable carbon nanotube is used, some examples of which are described in, for example, J. A. Rojas-Chapana, et al. *Nano letters* 4, 985-988 (2004), and J. Rojas-Chapana et al., *Lab Chip* 5, 536-539 (2005), from which the description of carbon nanotubes is incorporated herein by reference. In embodiments, commercially available carbon nanotubes can be used, such as from NANO-LAB, Inc., provided they are modified to be functionalized, such as with a carboxyl group, and filtered with a suitable microfilter, such as a 1 μm microfilter. For example, in one embodiment, a nanotube solution (30 mg/ml) is filtered with a 1 μm microfilter. In embodiments, a suitable microfilter is made of nylon.

In embodiments, the nanotubes are multiwall nanotubes, and have a diameter of 15-45 nm, inclusive, and including all numbers and ranges of numbers there between, and a length from 1 μm to 5 μm, inclusive, and including all numbers and ranges of numbers there between. In embodiments, at least some nanotubes are in physical contact with bacteria during performance of a method of the disclosure. In embodiments, the nanotubes are hollow.

In embodiments, the disclosure comprises subjecting a population of bacteria to microwave energy in the presence of carbon nanotubes as described herein, and the double stranded probes. Mixtures of distinct combinations of labeled and quencher probes are provided for use in, for example, multiplexed detection of distinct types of bacteria in the sample. The sample can be any sample that contains, or is suspected of containing bacteria. In embodiments, microwave energy is applied for a period of from 1-10 seconds, inclusive, and including all ranges of time there between. In embodiments, microwave energy is provided at a range from 300 MHz (100 cm) and 300 GHz (0.1 cm). In a non-limiting embodiment, about 2.45 GHz is used.

The following examples illustrate but are not intended to limit Part II of this disclosure.

Nanotube Assisted Microwave Electroporation

As discussed above, the present disclosure provides a microwave electroporation approach for transforming molecular probes into viable bacteria for intracellular sensing and pathogen identification (FIG. 24). Multiwall carbon nanotubes, which couple and localize the microwave energy, can enhance the electric field in a manner similar to a lightning rod for microwave electroporation with a minimal effect on the cell viability[14, 15]. To evaluate the feasibility of multiplex single cell pathogen identification using NAME, two molecular probes targeting the species-specific regions of bacterial 16S rRNA of *E. coli* (EC probe) and *P. aeruginosa* (PA probe) were designed and transformed into the bacteria (Tables 4-5). The performance of the double-stranded nucleic acid probe was first calibrated for use in homogeneous sensing (FIG. 25). For multiplex detection, the PA probe was labeled with 6-carboxyfluorescein (6-FAM) and the EC probe was labeled with 6-carboxytetramethylrhodamine (6-TAMRA). Uropathogenic *E. coli* and *P. aeruginosa* were transformed with both probes for pathogen identification (FIG. 20D). For samples with *E. coli* only, the fluorescence signal from the EC probe (red) was clearly observed in the bacteria while emission from the PA probe (green) was not observable. In contrast, *P. aeruginosa* displayed a high fluorescence signal from the PA probe (green) but not from the EC probe (red). Multiplex detection of both *E. coli* and *P. aeruginosa* was demonstrated by mixing the bacteria together. These results demonstrate the feasibility of NAME for multiplex pathogen identification.

Optimization of NAME Transformation for Pathogen Identification

A high transformation efficiency (i.e., percentage of bacteria that are transformed with probes) for single cell pathogen identification using intracellular probes facilitates quantification of the bacteria concentration, which is important for detecting flora contaminations and polymicrobial infections[19]. To analyze the influence of nanotubes on the transformation efficiency, the microwave electroporation procedure was performed with and without multiwall carbon nanotubes (FIG. 21A). Fluorescence intensity from bacteria was only observed in samples with nanotubes, supporting nanotubes enhancing the performance of microwave electroporation. The effect of the duration of microwave treatment on the transformation efficiency was investigated by counting the portion of bacteria with an observable fluorescence intensity (FIG. 21B). Examining the results revealed that the transformation efficiency gradually increased with time and reached a high transformation efficiency (>90%) at 10 seconds. Further increases in the microwave duration did not improve the transformation efficiency. Thus, in embodiments, microwaves are used for a period of about 1 second to about 10 seconds. In embodiments, microwaves are not used for more than 10 seconds.

We also analyzed the influence of the transformation solution (buffer and nanotube concentration) on the transformation efficiency and measured the ability of the bacteria to grow by agar plate culture after undergoing the NAME procedure (FIG. 21C and Table 6). We observed a low transformation efficiency (4.35±2.5%) of NAME with Mueller Hinton broth and a high efficiency with deionized water (89.3±16.2%). Nevertheless, NAME treatment in deionized water inhibited the growth of the bacteria in agar plates, despite the bacteria remaining motile in culture media. PBS 1× also exhibited a low transformation efficiency. Diluting PBS to 0.5× allowed a high transformation efficiency (~80-90%) while maintaining the bacteria growth to 49.48±5.49%. Thus, in embodiments, the disclosure includes use of a buffer, such as PBS, to enhance transformation efficiency, relative to transformation efficiency using a reference buffer. In embodiments, the buffer is less concentrated than PBS 1×. In embodiments, the buffer is PBS at a concentration of about 0.5×.

Similarly, a high nanotube concentration enhanced the transformation efficiency and reduced the bacteria growth. We also observed that the incubation time (incubation after microwave treatment) had a significant effect on the transformation efficiency (FIG. 21D). Each of these parameters (nanotube concentrations, microwave times, buffer concentrations, and incubation times) are encompassed by the disclosure. Fluorescence intensity in bacteria could be observed in as little as one minute (with a transformation efficiency of 4.4%). The transformation efficiency gradually increased with the incubation time to as high as 99.3%. Unless otherwise specified, 10 seconds of microwave treatment in 0.5×PBS with an incubation time of 30 minutes was applied for the rest of the disclosure. In embodiments, carbon nanotube percentages are from about 50% to about 100%, inclusive, and including a numbers and ranges of numbers there between.

Single Cell Pathogen Identification of Clinical Specimens

To further evaluate the applicability of NAME for pathogen identification, we applied NAME to identify bacteria isolated from clinical blood and urine samples. EC and PA probes were used in this approach. In addition, a universal (UNI) probe that targets the conserved region of the bacterial 16S rRNA was designed for detecting all bacteria (FIG. 26). The performance of these probes was evaluated with a panel of Gram-negative bacteria (E. coli, K. pneumoniae, and P. aeruginosa), which are common causes of bacterial infections (FIG. 22A)[20]. E. coli and P. aeruginosa were specifically identified at the single cell level with the EC and PA probes, respectively. The universal probes detected all three species successfully. In addition to clinical isolates, we also evaluated the ability of NAME to detect bacteria from clinical samples directly. FIG. 22B shows culture-free identification of bacteria from a patient's urine sample. FIG. 22 also shows multiplex detection of E. coli and P. aeruginosa with EC, PA and universal probes. These results collectively suggested that NAME is capable of rapid diagnosis of bacterial infections.

Single Cell Pathogen Identification and AST

The viability of the bacteria was preserved after NAME pathogen identification, which allows phenotypic AST in the same assay. We integrated pathogen identification and single cell AST by applying a microfluidic confinement technique (FIG. 23A) (18, from which the description of the microfluidic device and technique is incorporated herein by reference). It will be recognized that this approach can also be used with the device described in Part I of this disclosure. In this integrated identification and AST assay, the bacteria were transformed, loaded into the microchannels via capillary flow, and trapped in the channels for phenotypic AST. Pathogen identification with subsequent growth monitoring was demonstrated based on the fluorescence and bright-field images (FIG. 23B). A delay in the bacteria growth was observed after microwave electroporation compared to the untreated control. After a recovery time of 1.5 hours, the growth of transformed bacteria could be observed. AST was implemented by monitoring the bacterial growth in the channels with and without the presence of antibiotics. Uropathogenic E. coli, EC137 and EC132, which are susceptible and resistant to ciprofloxacin respectively, were

TABLE 6

Transformation efficiency and ability to grow after NAME

| Microwave | Carbon nanotube (%) | | | | | |
|---|---|---|---|---|---|---|
| time (s) | Efficiency (%) | Grow (%) | Efficiency (%) | Grow (%) | Efficiency (%) | Grow (%) |
| MHB | 100 | | 50 | | 10 | |
| 10 | 4.35 ± 2.50 | 89.32 ± 16.20 | 0 | 68.06 ± 6.96 | 0 | 89.43 ± 14.37 |
| 8 | 0 | 67.84 ± 13.71 | 0 | 77.19 ± 19.94 | 0 | 73.66 ± 11.96 |
| 6 | 0 | 84.46 ± 13.62 | 0 | 93.34 ± 14.69 | 0 | 106.41 ± 17.90 |
| DI water | 100 | | 50 | | 10 | |
| 10 | 91.99 ± 2.69 | 0 | 85.55 ± 3.84 | 0 | 3.33 ± 5.77 | 5.88 ± 10.19 |
| 8 | 86.02 ± 6.83 | 0 | 87.33 ± 3.79 | 0 | 0 | 23.52 ± 10.78 |
| 6 | 69.03 ± 14.39 | 0 | 76.82 ± 3.02 | 0 | 0 | 76.47 ± 24.79 |
| PBS, 1X | 100 | | 50 | | 10 | |
| 10 | 0 | 5.44 ± 4.25 | 0 | 61.90 ± 11.96 | 0 | 64.62 ± 22.39 |
| 8 | 0 | 2.72 ± 1.18 | 0 | 57.82 ± 12.47 | 0 | 59.18 ± 8.16 |
| 6 | 0 | 2.72 ± 3.12 | 0 | 48.29 ± 11.60 | 0 | 59.18 ± 5.40 |
| PBS, 0.5X | 100 | | 50 | | | |
| 10 | 90.87 ± 8.73 | 28.64 ± 3.85 | 81.58 ± 3.48 | 49.48 ± 5.49 | | | tested to evaluate the integrated assay (FIG. 23C and FIG. 27). The growth of EC137 was inhibited in the presence of ciprofloxacin (FIG. 23D). The bacteria did not display any observable growth in the channels. On the other hand, EC132 grew at a rate similar to the control group under the same condition (FIG. 23E). These data suggested that EC137 was susceptible to ciprofloxacin and EC132 was resistant to ciprofloxacin. The results were consistent with clinical microbiology, broth dilution, and agar pad data (FIG. 28). These data collectively demonstrate the feasibility of performing pathogen identification and AST in a single assay with a total assay time of approximately 3 hours, compared to days in standard approaches.

It will be recognized from the foregoing that in this Part II of this disclosure, we demonstrate intracellular delivery of molecular biosensors for identifying bacterial pathogens at the single cell level. Conventional transformation methods are often limited to competent cells and have a low efficiency and cell viability[21, 22]. We address these issues by performing microwave electroporation enhanced by multi-wall carbon nanotubes. Without intending to be constrained by any particular theory, it is considered that the nanotube-based delivery can be understood by the lightning rod effect, which creates a strong, localized field enhancement to induce temporary membrane disruptions to increase permeability[14, 15]. In this disclosure, we perform pathogen identification by transforming molecular biosensors into clinically relevant bacterial pathogens in as little as 30 minutes. This method allows culture-free, amplification-free pathogen identification at the single cell level. Unlike typical molecular biosensors that lyse the bacteria and dilute the intracellular content, our approach detects species-specific regions of the 16S rRNA inside the cells. Thus, in embodiments, cells analyzed by the NAME approach are not killed. The small volume of a bacterium (~femtoliter) leads to a high target concentration for single cell detection. The DNA probes were stable in the bacteria during the measurement timeframe (within one hour). Delivery of single-stranded DNA probes (without the quencher probe) resulted in rapid degradation of non-specific probes, suggesting the hybridization of the probe with the 16S rRNA stabilizes the probes and further enhances the specificity of the assay. For applications that require intracellular detection for an extended period of time, modified nucleic acids, such as locked nucleic acids and peptide nucleic acids, can be incorporated into the design of the molecular biosensors[23]. These characteristics of NAME collectively enable specific pathogen identification at the single cell level.

An aspect of the single cell analysis approach is the ability to quantify the bacteria, even in clinical samples containing multiple types of bacteria. This quantification capability facilitates distinguishing commensal flora from pathogens and identifying polymicrobial infections. Unlike normally sterile biological fluids (e.g., blood), microbiological analysis of urine, stool and respiratory secretions can often be complicated by the presence of commensal flora. Quantitative bacterial culture for urine and bronchoscopic samples determines the clinical significance of pathogenic and commensal bacteria isolated from these samples. Unlike molecular amplification approaches (e.g., PCR), NAME can estimate the bacterial concentration by counting from microscopic images. The disclosure includes miniaturized imaging systems and automated imaging analysis incorporated into the present platform for simplifying the imaging procedure[24, 25]. The NAME technique can be expected to eliminate the long time delay in conventional culture-based approaches and avoid the uncertainty in the enumeration of viable bacteria in amplification-based approaches.

Intracellular detection of bacterial 16S rRNA in viable cells facilitates subsequent AST in the same assay. The data presented in this Part II of the disclosure demonstrate the feasibility of integrated identification-AST to improve the microbiology workflow using a microfluidic single cell confinement device, which completes AST in a time scale comparable to the doubling time of the bacteria[18]. Despite the recovery time (~1.5 hours), which are also reported in other transformation techniques[26], integration of the microfluidic device and the NAME technique allows comprehensive microbiological analysis in approximately 3 hours. This capability can potentially support antimicrobial stewardship and will improve clinical management of bacterial infections by reducing unnecessary treatment, accelerating de-escalation to narrow-spectrum antibiotics, and avoiding undertreatment of multidrug-resistant bacteria. Compared to other diagnostic platforms that perform both pathogen identification and AST[10, 11], the present approach is rapid, cost-effective, and requires only a small amount of patient sample and a small number of bacteria.

Materials and Methods for Part II
Molecular Probe Design and Preparation

Four double-stranded probes were used in this disclosure (Table 4). Each probe contained two DNA strands. The donor strands were 22-24 nucleotides long and complementary to the target RNA of interest[27, 28]. The fluorophores, 6-FAM (Fluorescein) or 6-TAMRA (NHS Ester), were labeled at the 3' end of the donor strands. The quencher strands were 11-12 nucleotides in length. The dark quenchers, Iowa Black FQ for 6-FAM or Iowa Black RQ for 6-TAMRA, were labeled at the 5' end of the quencher strands immediately adjacent to the fluorophores on the donor strands. The probes were synthesized by Integrated DNA Technologies (Coralville, IA). Other reagents were purchased from Sigma Inc. (St. Louis, MO) unless otherwise specified. To conduct the assay, the probes were made by mixing the fluorophore and quencher strands in the buffer solution, which contains 10 mM Tris-EDTA with 100 mM NaCl at a 1:3 molar ratio, at 95° C. for 5 minutes. The mixtures were then allowed to cool down to room temperature slowly. The final concentration of the probes in the transformation test was $1.5 \times 10^3$ nM.

TABLE 4

Probe sequences and synthetic targets

| Probe Name[a] | Label, Modification | Sequence (5' to 3') | SEQ ID NO | Length (Position)[b] | ΔG (kcal/mole) |
|---|---|---|---|---|---|
| EC probe (Green) | | | | | |
| Donor | 3' 6-FAM | GGTATTAACTTTACTCCCTTCCTC | 1 | 24 (447) | |
| Quencher | 5' Iowa Black FQ™ | GAGGAAGGGAGT | 2 | 12 | −22.01 |

TABLE 4-continued

Probe sequences and synthetic targets

| Probe Name[a] | Label, Modification | Sequence (5' to 3') | SEQ ID NO | Length (Position)[b] | ΔG (kcal/mole) |
|---|---|---|---|---|---|
| EC probe (Red) | | | | | |
| Donor | 3' 6-TAMTSp | GGTATTAACTTTACTCCCTTCCTC | 3 | 24 (447) | |
| Quencher | 5' Iowa Black RQ™ | GAGGAAGGGAGT | 4 | 12 | -22.01 |
| EC target | Unlabeled | GAGGAAGGGAGTAAAGTTAATACC | 5 | 24 | -41.5 |
| PA probe | | | | | |
| Donor | 3' 6-FAM | GCT GAA CCA CCT ACG CGC GCT TT | 6 | 23 (570) | |
| Quencher | 5' Iowa Black FQ™ | AAA GCG CGC GTA | 7 | 12 | -28.04 |
| PA target | Unlabeled | AAA GCG CGC GTA GGT GGT TCA GC | 8 | 23 | -50.63 |
| UNI probe | | | | | |
| Donor | 3' 6-FAM | GGGTATCTAATCCTGTTTGCTC | 9 | 22 (776) | |
| Quencher | 5' Iowa Black FQ™ | GAGCAAACAGG | 10 | 11 | -20.12 |
| UNI target | Unlabeled | GAGCAAACAGGATTAGATACCC | 11 | 22 | -39.16 |

[a]Unless otherwise stated, the donor probes were modified with 3'Fluorescein, EC-TAMRA was modified with 3'TAMRA(NHS Easter)
[b]Position of the 5'nucleotide of donor probes in alignment with the bacterial 16S rRNA.

Clinical Samples

Positive urine samples and clinical isolates including three *Escherichia coli* (urine), *Escherichia coli* (blood culture), *Pseudomonas aeruginosa* (urine), and *Klebsiella pneumoniae* (urine) were obtained from the clinical microbiology laboratory at the Veterans Affairs Palo Alto Health Care System (VAPAHCS) or the clinical microbiology laboratory at the Penn State Hershey Medical Center (Table 5). The procedure was approved by the Penn State University Institutional Review Board.

5 minutes and then put into a microwave oven (700 W, 2.45 GHz) for 10 seconds. The microwave treated bacteria was incubated at room temperature for 30 minutes and washed 3 times with PBS (1×) to remove the extra probes and resuspended in PBS for imaging.

Counting and AST Testing on Microfluidic Device

The bacteria suspension (1 µl) was loaded onto a microscope slide and covered with a cover glass for imaging and counting using a fluorescence microscope (Leica DMI 4000B, objective 40×). The transformation efficiency was

TABLE 5

Clinical samples and sources of bacteria

| Pathogen | Source |
|---|---|
| (1) *E. coli* (EC/37) | Clinical isolates of uropathogenic *E. coli* and *P. aeruginosa* were |
| (2) *E. coli* (EC/32) | obtained from the clinical microbiology laboratory at the Veterans |
| (3) *P. aeruginosa* (Urine) | Affairs Palo Alto Health Care System (VAPAHCS). |
| (4) *E. coli* (Urine) | Positive urine samples with *E. coli* and *K. pneumoniae* were obtained from the |
| (5) *K. pneumoniae* (Urine) | clinical microbiology laboratory at the Penn State Hershey Medical Center. |
| (6) *E. coli* (Blood) | Positive blood culture bottles with *E. coli* were obtained from the clinical microbiology laboratory at the Penn State Hershey Medical Center. |

Bacterial Transformation by NAME

Bacteria were grown in Mueller Hinton Broth. To transform the double-stranded probe into bacteria, 100 µl of bacterial sample was centrifuged at 4500 rpm for 5 minutes and washed twice with phosphate buffer (PBS 1×). The multiwall carbon nanotubes that are functionalized with a carboxyl group (COOH) have a diameter of 30±15 nm and a length from 1 to 5 µm (NanoLab, Inc.). The nanotube solution (30 mg/ml) was filtered with a 1 µm microfilter. The pellet was resuspended into 100 µl filtered nanotube solution and incubated for 10 minutes at room temperature. Then, 10 µl molecular probe was added and incubated at room temperature for 10 minutes. The sample was incubated in ice for estimated by the number of bacteria with an observable fluorescence intensity over the total number of bacteria (bright-field). To conduct AST, the transformed bacteria were loaded onto the microfluidic device by capillary force. The microfluidic device was mounted onto a heated stage for microscopic observation.

1. Statistical Analysis

Statistical analyses were performed with GraphPad Prism 5 software. The data were analyzed using one-way analysis of variance and Tukey's post-hoc test. Data represent mean±s.e.m.

References for Part II, this Reference Listing is not an Indication that any Reference is Material to Patentability.

1. K. Bush et al., Tackling antibiotic resistance. *Nature reviews. Microbiology* 9, 894-896 (2011).
2. M. Davenport et al., New and developing diagnostic technologies for urinary tract infections. *Nat Rev Urol* 14, 296-310 (2017).
3. R. Riahi, K. E. Mach, R. Mohan, J. C. Liao, P. K. Wong, Molecular detection of bacterial pathogens using microparticle enhanced double-stranded DNA probes. *Analytical chemistry* 83, 6349-6354 (2011).
4. D. K. Kang et al., Rapid detection of single bacteria in unprocessed blood using Integrated Comprehensive Droplet Digital Detection. *Nature communications* 5, 5427 (2014).
5. A. M. Kaushik et al., Accelerating bacterial growth detection and antimicrobial susceptibility assessment in integrated picoliter droplet platform. *Biosensors & bioelectronics* 97, 260-266 (2017).
6. N. G. Schoepp et al., Rapid pathogen-specific phenotypic antibiotic susceptibility testing using digital LAMP quantification in clinical samples. *Science translational medicine* 9, (2017).
7. E. P. Magennis et al., Bacteria-instructed synthesis of polymers for self-selective microbial binding and labelling. *Nat Mater* 13, 748-755 (2014).
8. X. Ning et al., Maltodextrin-based imaging probes detect bacteria in vivo with high sensitivity and specificity. *Nat Mater* 10, 602-607 (2011).
9. K. E. Mach et al., Multiplex pathogen identification for polymicrobial urinary tract infections using biosensor technology: a prospective clinical study. *The Journal of urology* 182, 2735-2741 (2009).
10. E. Altobelli et al., Integrated Biosensor Assay for Rapid Uropathogen Identification and Phenotypic Antimicrobial Susceptibility Testing. *Eur Urol Focus* 3, 293-299 (2017).
11. P. Athamanolap, K. Hsieh, L. Chen, S. Yang, T. H. Wang, Integrated Bacterial Identification and Antimicrobial Susceptibility Testing Using PCR and High-Resolution Melt. *Analytical chemistry* 89, 11529-11536 (2017).
12. K. E. Mach, P. K. Wong, J. C. Liao, Biosensor diagnosis of urinary tract infections: a path to better treatment? *Trends in pharmacological sciences* 32, 330-336 (2011).
13. E. Vazquez, M. Prato, Carbon nanotubes and microwaves: interactions, responses, and applications. *Acs Nano* 3, 3819-3824 (2009).
14. J. A. Rojas-Chapana, M. A. Correa-Duarte, Z. F. Ren, K. Kempa, M. Giersig, Enhanced introduction of gold nanoparticles into vital *Acidothiobacillus ferrooxidans* by carbon nanotube-based microwave electroporation. *Nano letters* 4, 985-988 (2004).
15. J. Rojas-Chapana, J. Troszczynska, I. Firkowska, C. Morsczeck, M. Giersig, Multi-walled carbon nanotubes for plasmid delivery into *Escherichia coli* cells. *Lab Chip* 5, 536-539 (2005).
16. D. Meserve, Z. Wang, D. D. Zhang, P. K. Wong, A double-stranded molecular probe for homogeneous nucleic acid analysis. *Analyst* 133, 1013-1019 (2008).
17. V. Gidwani, R. Riahi, D D Zhang, P. K. Wong, Hybridization kinetics of double-stranded DNA probes for rapid molecular analysis. *Analyst* 134, 1675-1681 (2009).
18. Y. Lu et al., Single Cell Antimicrobial Susceptibility Testing by Confined Microchannels and Electrokinetic Loading. *Analytical chemistry*, (2013).
19. M. B. Kirkpatrick, J. B. Bass, Jr., Quantitative bacterial cultures of bronchoalveolar lavage fluids and protected brush catheter specimens from normal subjects. *Am Rev Respir Dis* 139, 546-548 (1989).
20. G. B. Nair, M. S. Niederman, Ventilator-associated pneumonia: present understanding and ongoing debates. *Intensive Care Med* 41, 34-48 (2015).
21. M. Mandel, A. Higa, Calcium-dependent bacteriophage DNA infection. *J Mol Biol* 53, 159-162 (1970).
22. R. Fregel, V. Rodriguez, V. M. Cabrera, Microwave improved *Escherichia coli* transformation. *Lett Appl Microbiol* 46, 498-499 (2008).
23. V. V. Demidov, PNA and LNA throw light on DNA. *Trends in biotechnology* 21, 4-7 (2003).
24. M. W. Kadlec, D. You, J. C. Liao, P. K. Wong, A Cell Phone-Based Microphotometric System for Rapid Antimicrobial Susceptibility Testing. *J Lab Autom* 19, 258-266 (2014).
25. Q. Wei et al., Fluorescent imaging of single nanoparticles and viruses on a smart phone. *Acs Nano* 7, 9147-9155 (2013).
26. S. Fiedler, R. Wirth, Transformation of bacteria with plasmid DNA by electroporation. *Analytical biochemistry* 170, 38-44 (1988).
27. S. Wang, Y. Xiao, D. D. Zhang, P. K. Wong, A gapmer aptamer nanobiosensor for real-time monitoring of transcription and translation in single cells. *Biomaterials* 156, 56-64 (2018).
28. Z. S. Dean, R. Riahi, P K Wong, Spatiotemporal dynamics of microRNA during epithelial collective cell migration. *Biomaterials* 37, 156-163 (2015).

What is claimed is:

1. A method for identifying bacteria comprising:
contacting a sample comprising bacteria with a carbon nanotube and microwave energy such that a probe is introduced into the bacteria, wherein the probe comprises a double strand polynucleotide probe, wherein a first strand of the double stranded probe comprises a detectable label, and a second strand of the double stranded probe comprises a quencher moiety that quenches a signal from the detectable label when the probe is double stranded,
allowing hybridization between only the labeled strand with a polynucleotide in the bacteria if bacteria are present,
and if bacteria are present, detecting a signal from the labeled strand that is hybridized to a polynucleotide in the bacteria to thereby identify the presence of, and/or the type of bacteria in the sample, and if the bacteria are not present, determining a lack of a signal from the labeled strand, and wherein a signal from the labeled strand if present is detected in a microfluidic device, and wherein the microfluidic device comprises: i) one or more bacteria trapping channels, and ii) one or more pneumatic channels in contact with the bacteria trapping channels, wherein the one or more pneumatic channels are configured to reduce the height of the one or more bacteria trapping channels to thereby trap only a single bacterium in the one or more bacteria trapping channels if said bacteria are present in a liquid biological sample that is introduced into the microfluidic device, thereby providing at least one trapped bacterium in at least one of the bacteria trapping channels.

2. The method of claim 1, wherein the polynucleotide in the bacteria comprises RNA.

3. The method of claim 2, wherein the RNA is ribosomal RNA (rRNA).

4. The method of claim 3, wherein the labeled strand comprises a sequence that is complementary to rRNA from a plurality of distinct bacteria species.

5. The method claim 3, wherein at least two double stranded probes are introduced into the bacteria, and wherein the two double stranded probes each comprise distinctly labeled first strands that have distinct sequences relative to each other, and wherein the two double stranded probes each comprise a second strand comprising a quencher moiety that quenches a signal from the detectable label when the probe is double stranded.

6. The method of claim 1, comprising determining the presence of the at least one trapped bacterium, and determining antimicrobial susceptibility (AST) for the at least one trapped bacterium by introducing an antimicrobial agent into the one or more bacteria trapping channels wherein the at least one bacterium is trapped, and subsequently determining viability of the at least one trapped bacterium, wherein a lack of lethality of the antimicrobial agent indicates resistance to the antimicrobial agent, and wherein lethality indicates susceptibility to the antimicrobial agent.

* * * * *